(12) United States Patent
Chai et al.

(10) Patent No.: US 11,078,488 B2
(45) Date of Patent: *Aug. 3, 2021

(54) FIBROTIC TREATMENT

(71) Applicant: Monash University, Clayton (AU)

(72) Inventors: Siew Yeen Chai, Clayton (AU); Robert Widdop, Clayton (AU); Tracey Gaspari, Clayton (AU); Huey Wen Lee, Clayton (AU)

(73) Assignee: MONASH UNIVERSITY, Clayton (AU)

(*) Notice: Subject to any disclaimer, the term of this patent is extended or adjusted under 35 U.S.C. 154(b) by 0 days.

This patent is subject to a terminal disclaimer.

(21) Appl. No.: 16/984,996

(22) Filed: Aug. 4, 2020

(65) Prior Publication Data

US 2020/0362354 A1   Nov. 19, 2020

Related U.S. Application Data

(63) Continuation of application No. 16/123,898, filed on Sep. 6, 2018, now Pat. No. 10,787,668, which is a continuation of application No. 15/747,697, filed as application No. PCT/AU2016/050681 on Jul. 29, 2016, now Pat. No. 10,100,311.

(30) Foreign Application Priority Data

Jul. 30, 2015 (AU) ............................... 2015903035

(51) Int. Cl.
| | |
|---|---|
| A61K 31/395 | (2006.01) |
| A61K 31/351 | (2006.01) |
| A61K 31/4433 | (2006.01) |
| C12N 15/113 | (2010.01) |
| A61K 31/4709 | (2006.01) |
| A61K 31/55 | (2006.01) |
| A61P 1/16 | (2006.01) |
| A61P 9/00 | (2006.01) |
| A61P 13/12 | (2006.01) |

(52) U.S. Cl.
CPC ........ *C12N 15/1137* (2013.01); *A61K 31/351* (2013.01); *A61K 31/395* (2013.01); *A61K 31/4433* (2013.01); *A61K 31/4709* (2013.01); *A61K 31/55* (2013.01); *A61P 1/16* (2018.01); *A61P 9/00* (2018.01); *A61P 13/12* (2018.01); *C12N 2310/14* (2013.01)

(58) Field of Classification Search
CPC . A61K 31/395; A61K 31/351; A61K 31/4433
USPC ................... 514/299, 277, 415, 619
See application file for complete search history.

(56) References Cited

U.S. PATENT DOCUMENTS

| | | | |
|---|---|---|---|
| 10,100,311 B2 | 10/2018 | Chai et al. | |
| 10,787,668 B2* | 9/2020 | Chai | A61K 31/351 |

FOREIGN PATENT DOCUMENTS

| | | |
|---|---|---|
| JP | 2015209483 | 3/2015 |
| WO | WO 2006/026832 | 3/2006 |
| WO | WO 2007/024946 | 3/2007 |
| WO | WO 2009/065169 | 5/2009 |
| WO | WO 2013/090833 | 6/2013 |
| WO | WO 2013/117503 | 8/2013 |
| WO | WO 2016/179645 | 11/2016 |

OTHER PUBLICATIONS

Albiston et al., "Identification and development of specific inhibitors for insulin-regulated aminopeptidase as a new class of cognitive enhancers", British Journal of Pharmacology, 2011, 164: 37-47.
Ma et al., "Role of Angiotensin II in Glomerular Injury", Seminars in Nephrology, 2001, 21(6): 544-553.
Lee et al., "Structure-Activity Study of LVV-Hemorphin-7: Angiotensin AT4 Receptor Ligand and Inhibitor of Insulin-Regulated Aminopeptidase", The Journal of Pharmacology and Experimental Therapeutics, 2003, 305(1): 205-211.
Sanderson et al., "Modulation of peripheral inflammation by locally administered hemorphin-7", Inflammation Research, 1998, 47(2): 49-55.
The extended European search report issued for European Application No. 16829507.9, dated Feb. 5, 2019.
Gasoari et al., "Insulin Regulated Aminopeptidase/AT₄ Receptor Deficiency is Both Cardio- and Vaso-Protective in Angiotensin II-Infused Mice", Abstract From the 33rd Annual Scientific Meeting of the HBPRCA, Hypertension, 2012, 60(2).
Lee et al., "AT4 Receptor/Insulin Regulated Aminopeptidase Inhibition Protects Against Angiotensin II-Induced Cardiac Fibrosis and Vascular Dysfunction", Journal of Hypertension, 2014, vol. 32, e-Supplement 1, e551-e552.
Yang et al., "Organotin(IV) complexes derived from Schiff base N'-[(1E)-(2-hydroxy-3-methoxyphenyl)methylidene] pyridine-3-carbohydrazone: Synthesis, in vitro cytotoxicities and DNA/BSA interaction", Journal of Organometallic Chemistry, 2016, 804: 48-58.
Yang et al., "Angiotensin IV protects against angiotensin II-induced cardiac injury via AT4 receptor", Peptides, 2011, 32: 2108-2115.
Di Sario et al., The anti-fibrotic effect of pirfenidone in rat liver fibrosis is mediated by downregulation of procollagen α1(I), TIMP-1 and MMP-2, Digestive and Liver Disease, 2004, 36: 744-751.
Garcia et al., "Pirfenidone effectively reverses experimental liver fibrosis", Journal of Hepatology, 2002, 37: 797-805.
Herrmann et al., "Olodaterol shows anti-fibrotic efficacy in in vitro and in vivo models of pulmonary fibrosis", British Journal of Pharmacology, 2017, 174: 3848-3864.

(Continued)

*Primary Examiner* — Raymond J Henley, III
(74) *Attorney, Agent, or Firm* — James S. Keddie; Bozicevic, Field & Francis LLP

(57) ABSTRACT

The present invention relates to compositions, methods and kits for the treatment of fibrosis. In particular, the compositions, methods and kits are particularly useful, but not limited to, the treatment of cardiac fibrosis. The invention provides a method of treating fibrosis in an individual comprising administering an inhibitor of insulin-regulated aminopeptidase (IRAP), thereby treating fibrosis.

18 Claims, 38 Drawing Sheets

Specification includes a Sequence Listing.

(56) References Cited

OTHER PUBLICATIONS

Iyer et al., "Lung Fibrosis is Ameliorated by Pirfenidone Fed in Diet After the Second Dose in a Three-Dose Bleomycin-Hamster Model", Experimental Lung Research, 1998, 24: 119-133.

Iyer et al., "Effects of Pirfenidone on Procollagen Gene Expression at the Transcriptional Level in Bleomycin Hamster Model of Lung Fibrosis", The Journal of Pharmacology and Experimental Therapeutics, 1999, 289(1): 211-218.

Rago et al., "Effect of preventive or therapeutic treatment with angiotensin 1-7 in a model of bleomycin-induced lung fibrosis in mice", Journal of Leukocyte Biology, 2019, 1-10.

Rosshart et al., "Laboratory mice born to wild mice have natural microbiota and model human immune responses", Science, 2019, 365: 461.

Salazar-Montes et al., "Potent antioxidant role of Pirfenidone in experimental cirrhosis", European Journal of Pharmacology, 2008, 595: 69-77.

Shimizu et al., "Pirfenidone improves renal function and fibrosis in the postobstructed kidney", Kidney International, 1998, 54: 99-109.

Szeto et al., "YAP/TAZ Are Mechanoregulators of TGF-β-Smad Signaling and Renal Fibrogenesis", J Am Soc Nephrol., 2016, 27(10): 3117-3128.

Tada et al., "Pirfenidone Inhibits Dimethylnitrosamine-Induced Hepatic Fibrosis in Rats", Clinical and Experimental Pharmacology and Physiology, 2001, 28: 522-527.

Tajima et al., "Metformin prevents liver tumorigenesis induced by high-fat diet in C57Bl/6 mice", Am J Physiol Endocrinol Metab, 2013, 305: E987-E998.

Wollin et al., "Antifibrotic and Anti-inflammatory Activity of the Tyrosine Kinase Inhibitor Nintedanib in Experimental Models of Lung Fibrosis", J Pharmacol Exp Ther, 2014, 349: 209-220.

Andersson et al., "Disulfide Cyclized Tripeptide Analogues of Angiotensin IV as Potent and Selective Inhibitors of Insulin-Regulated Aminopeptidase (IRAP)", Journal of Medicinal Chemistry, 2010, 53: 8059-8071.

* cited by examiner

A)

IRAP Expression

B)

C)

A)

B)

D)

E)

F)

A)

B)

A)

B)

(**p<0.01, 1-way ANOVA; n=3)

SEQUENCE LISTING

```
<160> NUMBER OF SEQ ID NOS: 9

<210> SEQ ID NO 1
<211> LENGTH: 9
<212> TYPE: PRT
<213> ORGANISM: Artificial sequence
<220> FEATURE:
<223> OTHER INFORMATION: synthetic sequence

<400> SEQUENCE: 1

Cys Tyr Phe Gln Asn Cys Pro Arg Gly
1               5

<210> SEQ ID NO 2
<211> LENGTH: 5
<212> TYPE: PRT
<213> ORGANISM: Artificial sequence
<220> FEATURE:
<223> OTHER INFORMATION: synthetic sequence

<400> SEQUENCE: 2

Tyr Gly Gly Phe Leu
1               5

<210> SEQ ID NO 3
<211> LENGTH: 6
<212> TYPE: PRT
<213> ORGANISM: Artificial sequence
<220> FEATURE:
<223> OTHER INFORMATION: synthetic sequence

<400> SEQUENCE: 3

Val Tyr Ile His Pro Phe
1               5

<210> SEQ ID NO 4
<211> LENGTH: 6
<212> TYPE: PRT
<213> ORGANISM: Artificial sequence
<220> FEATURE:
<223> OTHER INFORMATION: synthetic sequence

<400> SEQUENCE: 4

Cys Tyr Cys His Pro Phe
1               5

<210> SEQ ID NO 5
<211> LENGTH: 6
```

```
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (1)..(1)
<223> OTHER INFORMATION: Xaa at position 1 is homocysteine.
<220> FEATURE:
<221> NAME/KEY: MISC_FEATURE
<222> LOCATION: (3)..(3)
<223> OTHER INFORMATION: Xaa at position 3 is homocysteine.

<400> SEQUENCE: 5

Xaa Tyr Xaa His Pro Phe
1               5

<210> SEQ ID NO 6
<211> LENGTH: 9
<212> TYPE: PRT
<213> ORGANISM: Artificial sequence
<220> FEATURE:
<223> OTHER INFORMATION: synthetic sequence

<400> SEQUENCE: 6

Cys Tyr Ile Gln Asn Cys Pro Leu Gly
1               5

<210> SEQ ID NO 7
<211> LENGTH: 19
<212> TYPE: DNA
<213> ORGANISM: Artificial sequence
<220> FEATURE:
<223> OTHER INFORMATION: synthetic sequence

<400> SEQUENCE: 7
gataagatag tagggggaga                                              19

<210> SEQ ID NO 8
<211> LENGTH: 20
<212> TYPE: DNA
<213> ORGANISM: Artificial sequence
<220> FEATURE:
<223> OTHER INFORMATION: synthetic sequence

<400> SEQUENCE: 8
caatagaggt acagtcacca                                              20

<210> SEQ ID NO 9
<211> LENGTH: 22
<212> TYPE: DNA
<213> ORGANISM: Artificial sequence
<220> FEATURE:
<223> OTHER INFORMATION: synthetic sequence

<400> SEQUENCE: 9
ggagaataag ggctgtgaga ga                                           22
```

FIBROTIC TREATMENT

CROSS REFERENCE(S) TO RELATED APPLICATIONS

This application is a continuation of Ser. No. 16/123,898, filed on Sep. 6, 2018, and now U.S. Pat. No. 10,787,668, which is a continuation of Ser. No. 15/747,697, filed on Jan. 25, 2018, and now U.S. Pat. No. 10,100,311, which is a § 371 national phase of International Application No. PCT/AU2016/050681, filed on Jul. 29, 2016, which claims priority from Australian provisional application no. 2015903035, the entire contents of which applications are incorporated herein by reference.

FIELD OF THE INVENTION

The present invention relates to compositions, methods and kits for the treatment of fibrosis. In particular, the compositions, methods and kits are particularly useful, but not limited to, the treatment of organ fibrosis.

BACKGROUND OF THE INVENTION

Cardiovascular diseases (CVDs) remain the world's leading cause of morbidity and mortality, claiming 17 million deaths annually, accounting for 1 death every 2s worldwide. Importantly, prevalence of major CVDs increases exponentially after the age of 60, with aged patients often suffering from cardiac dysfunction or chronic heart failure (CHF).

CVDs are often initiated upon any cardiac insult or injury, which then triggers the innate defense mechanism and inflammatory response to counter-regulate and repair the injury, in a process known as cardiac remodeling. However, repetitive injury or dysregulated reactive remodeling eventually leads to accumulation of excessive collagens in the heart, driving towards a progressively irreversible fibrotic response, leading to permanent scarring or cardiac fibrosis. Subsequently, blood supply to the heart is impaired, while increased stiffness of the heart further hinders cardiac contractility which predisposes to myocardial infarction (MI), chronic heart failure (CHF) or end organ damage. Such events are more likely to occur in the aging population, thus further increasing the susceptibility towards myocardial infarction or injury, with ageing itself compromised by the inefficient reparative process. Moreover, there are few treatments available which are directed against fibrosis. Of these, angiotensin converting enzyme (ACE) inhibitor or angiotensin receptor blockers (ARBs) only reduced CV mortality rate by ~7%.

Fibrosis can occur in various tissues, such as the heart (as discussed above), lungs, liver, skin, blood vessels and kidneys.

There is a need for therapies for the treatment and/or prevention of fibrosis.

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

SUMMARY OF THE INVENTION

The present invention provides a method of treating fibrosis in an individual comprising administering an inhibitor of insulin-regulated aminopeptidase (IRAP), thereby treating fibrosis. Preferably, the individual is identified as having fibrosis.

In any aspect of the present invention, the method or use reduces progression of at least one clinically or biochemically observable characteristic of fibrosis, thereby treating fibrosis.

In any aspect of the present invention, the method or use reverses at least one clinically or biochemically observable characteristic of fibrosis, thereby treating fibrosis.

The clinically or biochemically observable characteristic may be any one or more of the following organ dysfunction, scarring, alteration of normal extracellular matrix balance, increase in collagen deposition, differentiation of fibroblasts to myofibroblasts, reduction in the level of matrix metalloproteinases and increase in the level of tissue Inhibitors of matrix metalloproteinases. Preferably, collagen is a precursor or mature forms of collagen α1 Type 1.

In any aspect of the invention, the fibrosis may be age-induced, injury-induced or stress-induced. Preferably, the fibrosis is selected from the group consisting of cardiac fibrosis, liver fibrosis, kidney fibrosis, vascular fibrosis, lung fibrosis and dermal fibrosis.

In any method of the invention, the method further comprises the step of identifying an individual having fibrosis.

In any aspect of the invention, the inhibitor of IRAP inhibits IRAP mediated signalling. Typically, the inhibitor of IRAP directly inhibits the enzymatic activity of IRAP. Preferably, the inhibitor binds to the active site of IRAP. More preferably, the inhibitor of IRAP competes with, or prevents the binding of a substrate of IRAP for binding to IRAP.

The inhibitor of IRAP may exhibit a K value of less than 1 mM, preferably less than 100 µM, more preferably less than 10 µM, as determined by an assay as described herein, for example an assay that determines aminopeptidase activity or substrate degradation. Preferably the assay involves human IRAP. Typically, the assay of amino peptidase activity comprises hydrolysis of the synthetic substrate L-Leucine 7-amido-4-methyl coumarin hydrochloride (Leu-MCA) monitored by release of the fluorogenic product MCA by IRAP, preferably human IRAP. The assay of substrate degradation may be degradation of the peptide substrates CYFQNCPRG (SEQ ID NO: 1) or YGGFL (SEQ ID NO: 2).

An inhibitor of IRAP may be selected from the group consisting of a small molecule, an antibody, a peptide or an interfering RNA.

The invention also provides a method of alleviating or ameliorating a symptom of fibrosis in a subject in need thereof, the method comprising administering to the subject in need thereof a therapeutically effective amount of an inhibitor of IRAP, thereby alleviating or ameliorating a symptom of fibrosis in the subject. Preferably, the fibrosis is age-induced, as a result of underlying tissue injury or cardiovascular disease.

The invention also provides use of an inhibitor of IRAP in the manufacture of a medicament for the treatment or prevention of fibrosis in a subject in need thereof.

The present invention provides a method for the treatment of fibrosis in a subject comprising the steps of
    identifying a subject having fibrosis; and
    administering to the subject in need thereof a therapeutically effective amount of an inhibitor of IRAP,
    thereby treating fibrosis in the subject.

The invention has particular application to a subject having organ dysfunction, scarring, alteration of normal extracellular matrix balance, increase in collagen deposition, increased collagen volume fraction, differentiation of fibroblasts to myofibroblasts, reduction in the level of matrix metalloproteinases and increase in the level of tissue Inhibitors of matrix metalloproteinases, increased levels of either N-terminal or C-terminal propeptide of type I procollagen (PINP or PICP), decreased levels of C-terminal telepeptide of Type I collagen (CTP or CITP), increased collagen deposition and impaired cardiac function measured by various non-invasive imagining techniques, and impaired renal function as measured by increased proteinurea and albuminurea, decreased glomerular filtration rate or doubling of creatinine levels.

The present invention provides a method for the treatment of age-induced fibrosis or organ fibrosis related to tissue injury, the method comprising the steps of identifying a subject having age-induced fibrosis or organ fibrosis related to tissue injury; and administering to the subject in need thereof a therapeutically effective amount of an inhibitor of IRAP, thereby treating age-induced fibrosis or organ fibrosis related to tissue injury.

In any aspect or embodiment of the invention, age-induced fibrosis may be reference to age-induced fibrosis of the heart (cardiac), kidney (renal), blood vessels (vascular), liver (hepatic), pancreas and lung (pulmonary).

The present invention provides a method for the treatment or prevention of fibrosis, the method comprising the step of administering a composition to the subject for treatment or prevention, wherein the composition comprises, consists essentially of or consists of an inhibitor of IRAP and a pharmaceutically acceptable diluent, excipient or carrier.

In any method or use of the invention described herein, an inhibitor of IRAP may be administered systemically or directly to the site of disease. The inhibitor of IRAP may be formulated for oral administration.

The invention provides a pharmaceutical composition for treating or preventing fibrosis comprising an inhibitor of IRAP and a pharmaceutically acceptable diluent, excipient or carrier. In one embodiment, the only active ingredient present in the composition is an inhibitor of IRAP.

The invention provides a pharmaceutical composition for treating or preventing fibrosis comprising as an active ingredient an inhibitor of IRAP and a pharmaceutically acceptable diluent, excipient or carrier. In one embodiment, the only active ingredient present in the composition is an inhibitor of IRAP.

The invention provides a pharmaceutical composition for treating or preventing fibrosis comprising as a main ingredient an inhibitor of IRAP and a pharmaceutically acceptable diluent, excipient or carrier. In one embodiment, the only active ingredient present in the composition is an inhibitor of IRAP.

The invention also provides an inhibitor of IRAP for use in the treatment of fibrosis.

The invention also provides a pharmaceutical composition comprising an inhibitor of IRAP and a pharmaceutically acceptable diluent, excipient or carrier for use in the treatment of fibrosis.

In one aspect of the present invention, the inhibitor of IRAP has a structure according to Formula (I):

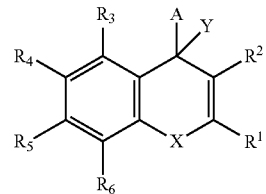

(I)

wherein

A is aryl, heteroaryl carbocyclyl or heterocyclyl, each of which may be optionally substituted, when $R^1$ is $NHCOR_8$; or quinolinyl, isoquinolinyl, cinnolinyl, quinazolinyl, quinoxalinyl, 1,8-naphthyridyl, phthalazinyl or pteridinyl, each of which may be optionally substituted, when $R^1$ is $NR_7R_8$, $NHCOR_8$, $N(COR_8)_2$, $N(COR_7)(COR_8)$, $N=CHOR_8$ or $N=CHR_8$;

X is O, NR' or S, wherein R' is hydrogen, optionally substituted alkyl, optionally substituted alkenyl, optionally substituted alkynyl, optionally substituted aryl, optionally substituted acyl, optionally substituted heteroaryl, optionally substituted carbocyclyl or optionally substituted heterocyclyl;

$R_7$ and $R_8$ are independently selected from hydrogen, optionally substituted alkyl, optionally substituted aryl, or $R_7$ and $R_8$, together with the nitrogen atom to which they are attached form a 3-8-membered ring which may be optionally substituted;

$R^2$ is CN, $CO_2R^9$, $C(O)O(O)R^9$, $C(O)R^9$ or $C(O)NR^9R^{10}$ wherein $R^9$ and $R^{10}$ are independently selected from alkyl, alkenyl, alkynyl, aryl, heteroaryl, carbocyclyl, heterocyclyl, each of which may be optionally substituted, and hydrogen; or $R^9$ and $R^{10}$ together with the nitrogen atom to which they are attached, form a 3-8-membered ring which may be optionally substituted;

$R_3$-$R_6$ are independently selected from hydrogen, halo, nitro, cyano alkyl, alkenyl, alkynyl, aryl, heteroaryl, heterocyclyl, carbocyclyl, hydroxy, alkoxy, alkenyloxy, alkynyloxy, alkynyloxy, aryloxy, heteroaryloxy, heterocyclyloxy, amino, acyl, acyloxy, carboxy, carboxyester, methylenedioxy, amido, thio, alkylthio, alkenylthio, alkynylthio, arylthio, heteroarylthio, heterocyclylthio, carbocyclylthio, acylthio and azido, each of which may be optionally substituted where appropriate, or any two adjacent $R^3$-$R^6$, together with the atoms to which they are attached, form a 3-8-membered ring which may be optionally substituted; and Y is hydrogen or $C_{1-10}$alkyl, or a pharmaceutically acceptable salt or solvate thereof.

In any aspect of the present invention, the inhibitor of IRAP has a structure according to Formula (II):

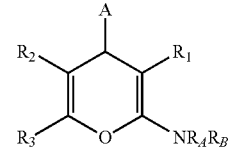

(II)

wherein

A is selected from alkyl, alkenyl, alkynyl, aryl, arylalkyl, heteroaryl, heteroarylalkyl, carbocyclyl, carbocyclylalkyl, each of which may be optionally substituted;

$R_A$ and $R_B$ are independently selected from hydrogen, alkyl and acyl;
$R_1$ is selected from CN or $CO_2R_C$;
$R_2$ is selected from $CO_2R_C$ and acyl;
$R_3$ is selected from alkyl, alkenyl, alkynyl, aryl, arylalkyl, heteroaryl, heteroarylalkyl, carbocyclyl, carbocyclylalkyl, each of which may be optionally substituted; or
$R_2$ and $R_3$ together form a 5-6-membered saturated ketocarbocyclic ring:

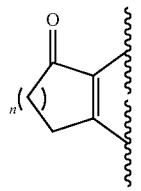

wherein n is 1 or 2;
and which ring may be optionally substituted one or more times by $C_{1-6}$alkyl; or
$R_2$ and $R_3$ together form a 5-membered lactone ring (a) or a 6-membered lactone ring (b)

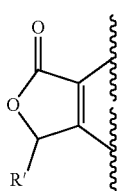
(a)

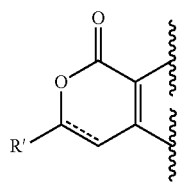
(b)

wherein ═══ is an optional double bond and R' is alkyl.
$R_C$ is selected from alkyl, alkenyl, alkynyl, aryl, arylalkyl, heteroaryl, heteroarylalkyl, carbocyclyl, carbocyclylalkyl, each of which may be optionally substituted;
or a pharmaceutically acceptable salt, solvate or prodrug thereof.

In any aspect of the present invention, the inhibitor of IRAP has a structure according to Formula (III):

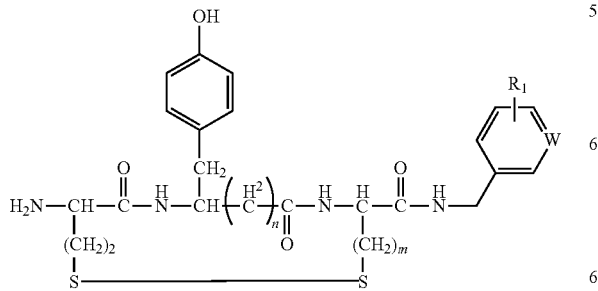
(III)

wherein
$R_1$ is H or $CH_2OOH$; and
n is 0 or 1; and
m is 1 or 2; and
W is CH or N;
or a pharmaceutically acceptable salt, solvate or prodrug thereof.

In one embodiment, the inhibitor has the structure:

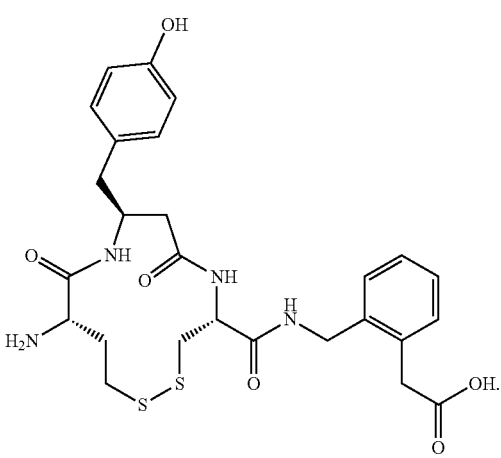 [SMILES: N[C@H]1CCSSC[C@@H](C(=O)NCc2ccccc2CC(=O)O)NC(=O)C[C@H](Cc2ccc(O)cc2)NC1=O]

In another embodiment of the present invention, the inhibitor of IRAP has a structure according to any one of the following sequences:

(SEQ ID NO: 3)
Val-Tyr-Ile-His-Pro-Phe, (SEQ ID NO: 4)
c[Cys-Tyr-Cys]-His-Pro-Phe,
and (SEQ ID NO: 5)
c[Hcy-Tyr-Hcy]-His-Pro-Phe.

In yet another embodiment of the present invention, the inhibitor has a structure according to the compound

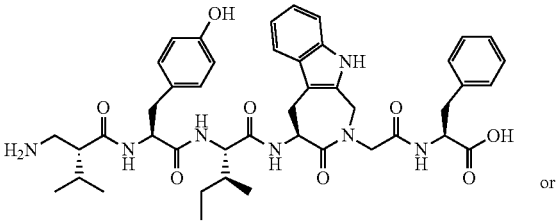
or

-continued

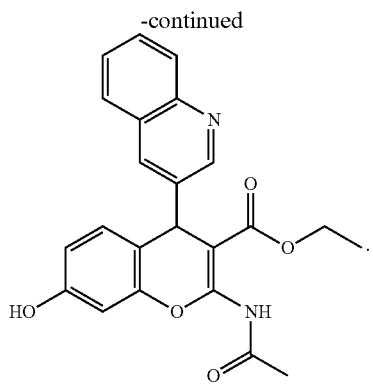

In any aspect of the present invention, the inhibitor of IRAP may be any compound or inhibitor as described herein.

As used herein, except where the context requires otherwise, the term "comprise" and variations of the term, such as "comprising", "comprises" and "comprised", are not intended to exclude further additives, components, integers or steps.

Further aspects of the present invention and further embodiments of the aspects described in the preceding paragraphs will become apparent from the following description, given by way of example and with reference to the accompanying drawings.

Quantification of IRAP in 5 µm thick transverse heart sections from adult (4-6 month old) and aged (18-22 month old) WT and IRAP deficient (IRAP$^{-/-}$) mice (n=5). (c) Quantification of IRAP in 5 µm thick transverse heart sections from aged (18-22 month old) WT mice treated for 4 weeks with vehicle or the IRAP inhibitor, HFI-419 (500 ng/kg/min; s.c.; n=5-8). Quantification of IRAP expressed as percent positive stained tissue area. Data expressed as mean±s.e.m; *P<0.05, **P<0.01, determined by two way analysis of variance (ANOVA) (b) or unpaired t-test (c).

Figure 9:
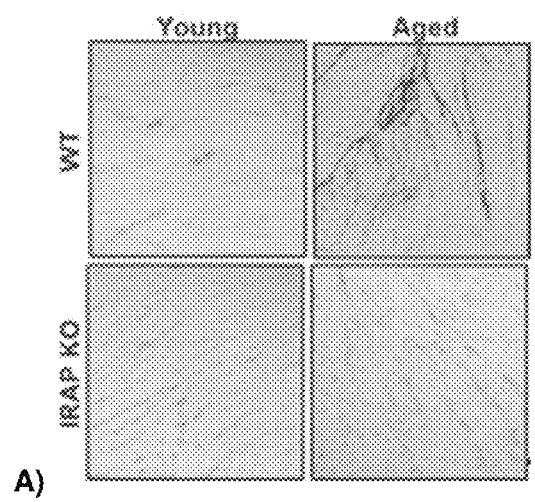
Figure 9:
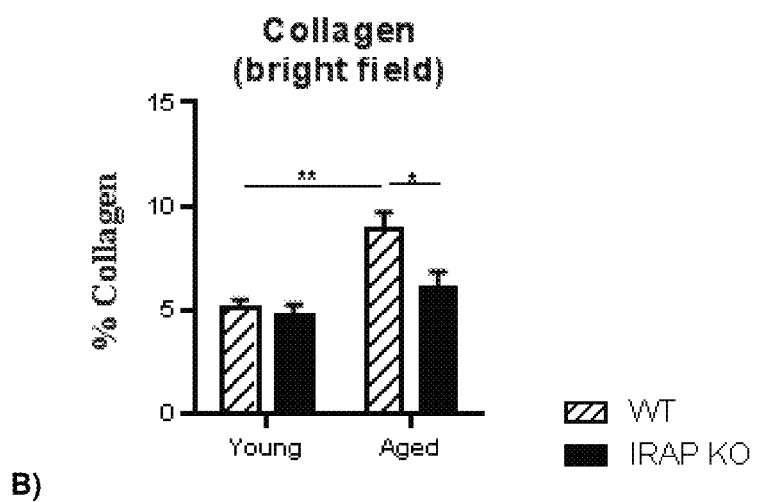

FIG. 9: IRAP deficiency prevents age-induced cardiac fibrosis. (a) Representative images of picrosirius red stained collagen in transverse heart sections of adult (4-6 month old) and aged (18-22 month old) WT and IRAP$^{-/-}$ mice. (b) Quantification of positive stained area for interstitial collagen, under bright field microscopy, expressed as percent positive stained tissue area (n=5-9). Data expressed as mean±s.e.m; *P<0.05, **P<0.01 determined by two way analysis of variance (ANOVA). Analogous data for interstitial and perivascular collagen measured under polarized light microscopy are depicted in FIG. 10a-d.

Figure 2:
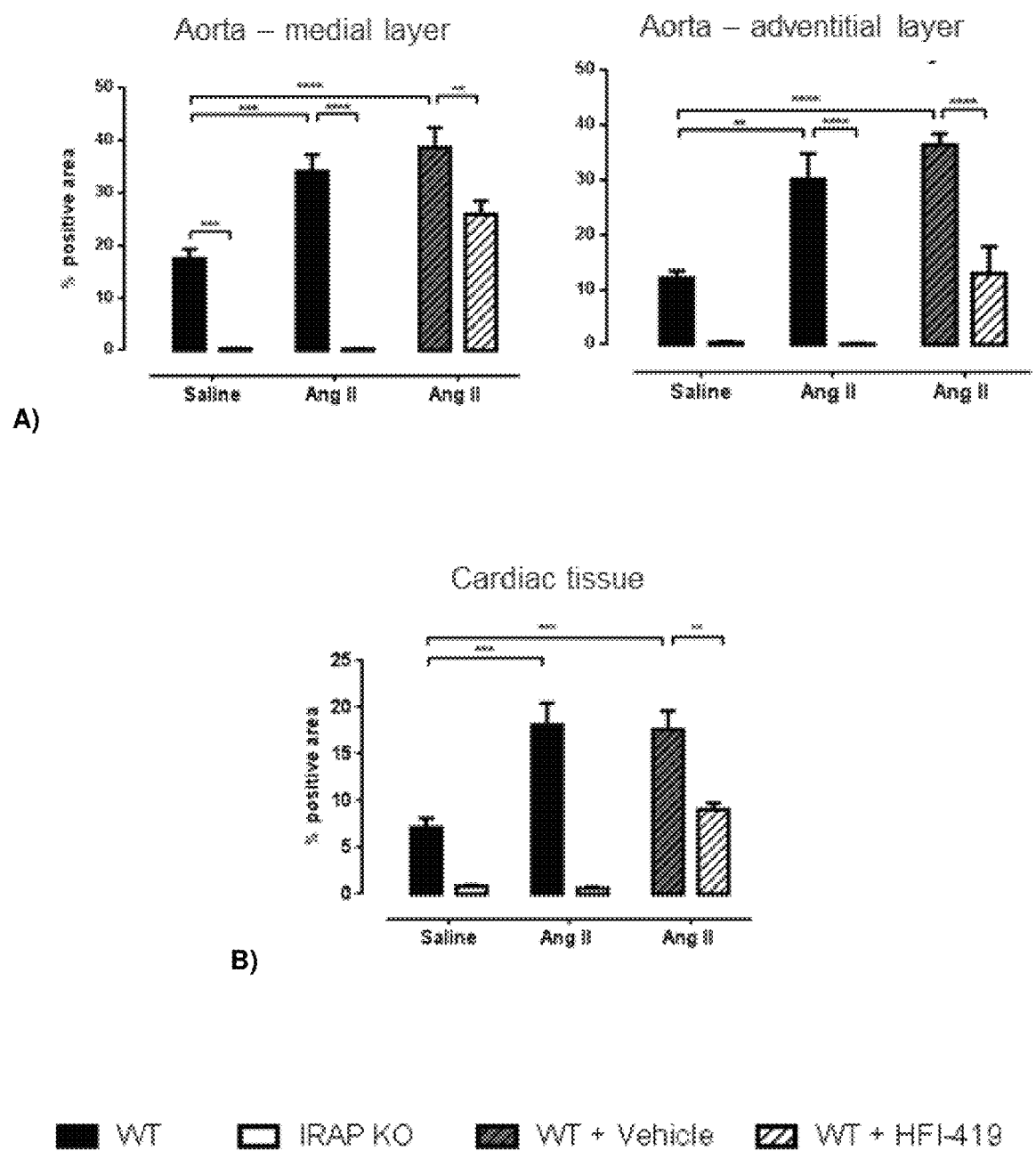
FIG. 2: IRAP expression is increased in aortae and hearts of Angiotensin II-infused WT mice. (a) Quantification of IRAP expression in medial and adventitial regions of 5 μm thick transverse aortic sections from adult (4-6 month old) WT and IRAP$^{-/-}$ mice treated with Ang II±vehicle/HFI-419 (n=5). (b) Quantification of IRAP in 5 μm thick transverse heart sections from adult (4-6 month old) WT and IRAP$^{-/-}$ mice treated with Ang II±vehicle/HF-419 (n=5). Quantification of IRAP expressed as percent positive stained tissue area. Data expressed as mean s.e.m; P<0.01, *P<0.001, ****P<0.0001 determined by two way analysis of variance (ANOVA).
Figure 10:
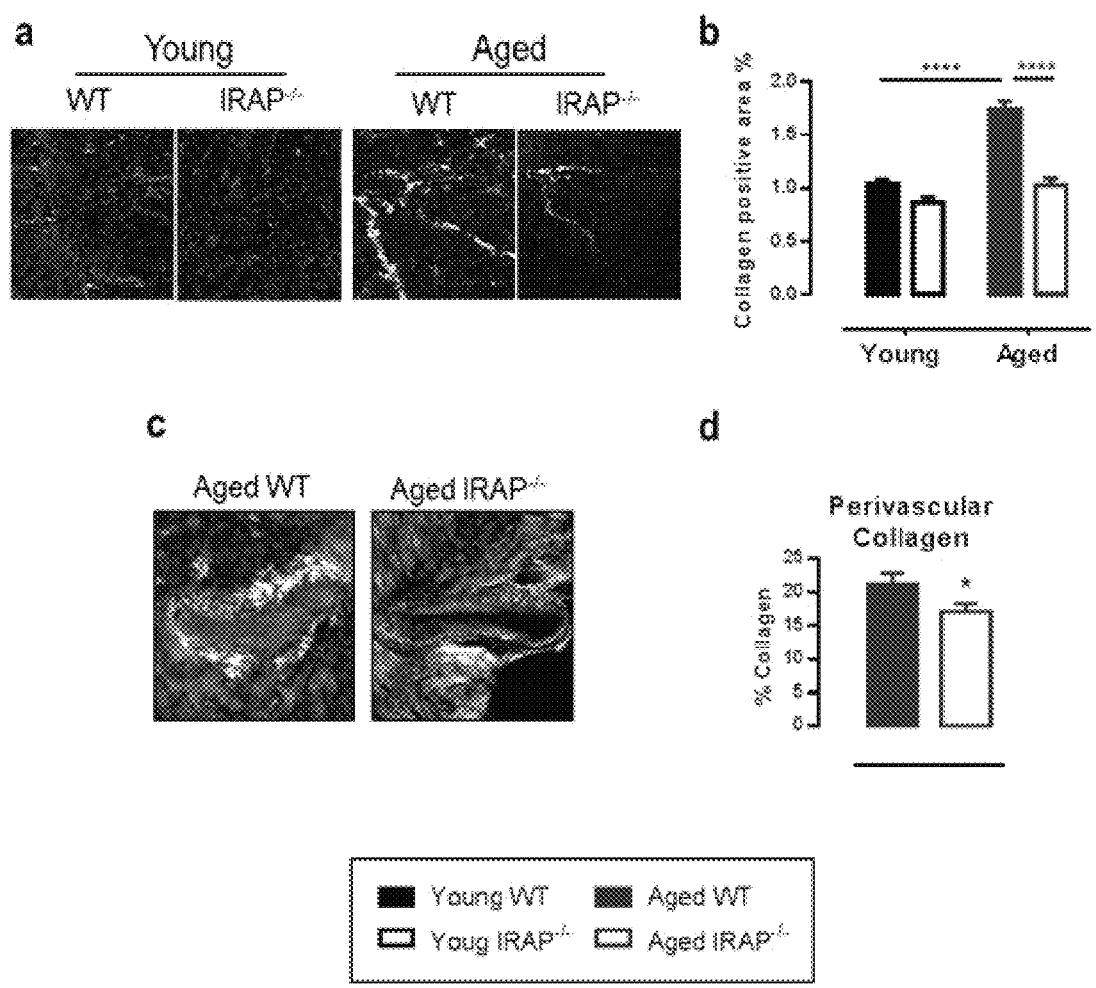

FIG. 10: Aged IRAP deficient mice are protected against age-induced cardiac fibrosis. Interstitial (a, b) and perivascular (c,d) collagen expression was quantified using polarized microscopy in picrosirius red stained heart sections from young and aged WT and IRAP$^{-/-}$ mice. Compared with bright field microscopy (FIG. 2), this analysis revealed the same effect on collagen expression but with an absolute lower level of collagen. Data expressed as mean s.e.m; *P<0.05, ****P<0.0001 determined by two way analysis of variance (ANOVA) for interstitial fibrosis and unpaired t-test for perivascular fibrosis; Young mice: Wt, n=8 and IRAP$^{-/-}$, n=10; Aged mice: WT, n=14 and IRAP$^{-/-}$, n=14).

Figure 11:
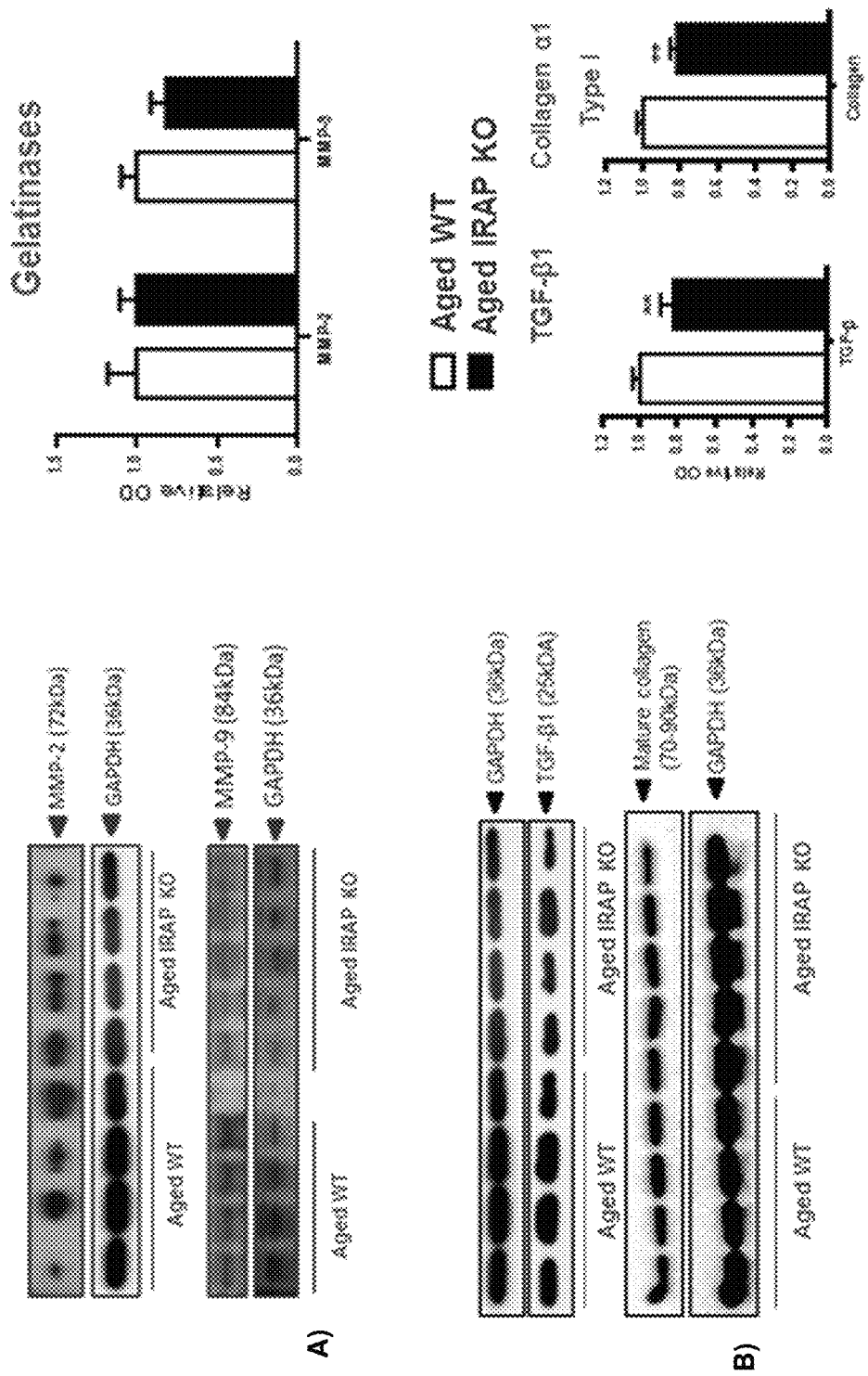
Figure 11:
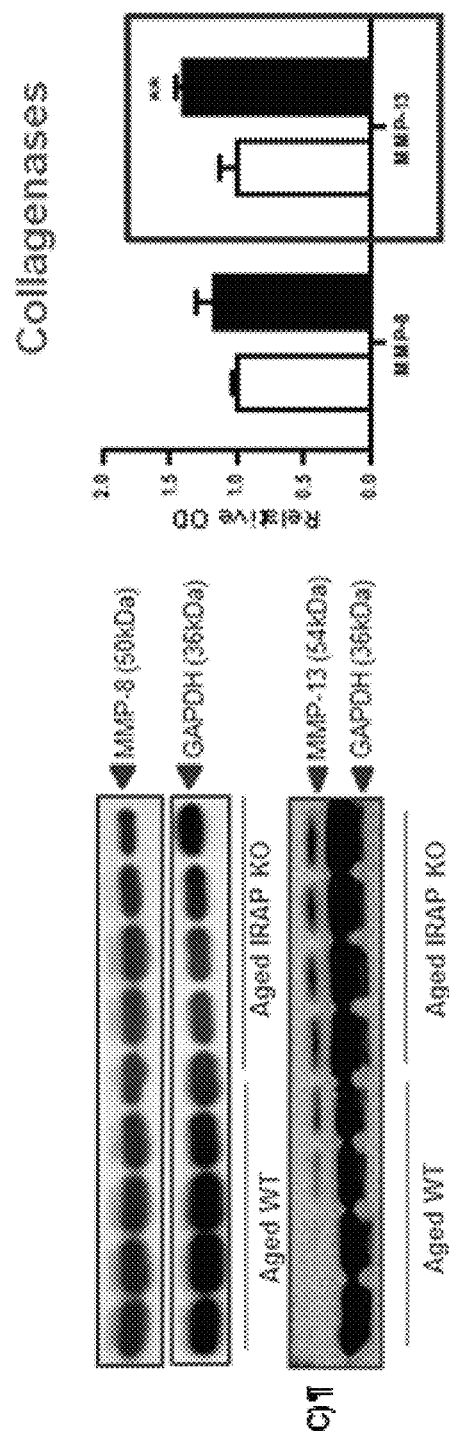

FIG. 11: IRAP deficiency alters age-induced extracellular matrix balance. Western blots and densitometric quantification of protein expression of TGF-$\beta_1$ and collagen α1 Type I (a), matrix metalloproteinase (MMP)-2 and MMP-9 (b), MMP-8 and MMP-13 (c) in cardiac tissue from aged WT and IRAP$^{-/-}$ mice expressed as relative ratio to mean of WT control±s.e.m; (Aged mice: WT, n=4-8 and IRAP$^{-/-}$, n=5-11). **P<0.01, determined by unpaired t-test.

Figure 12:
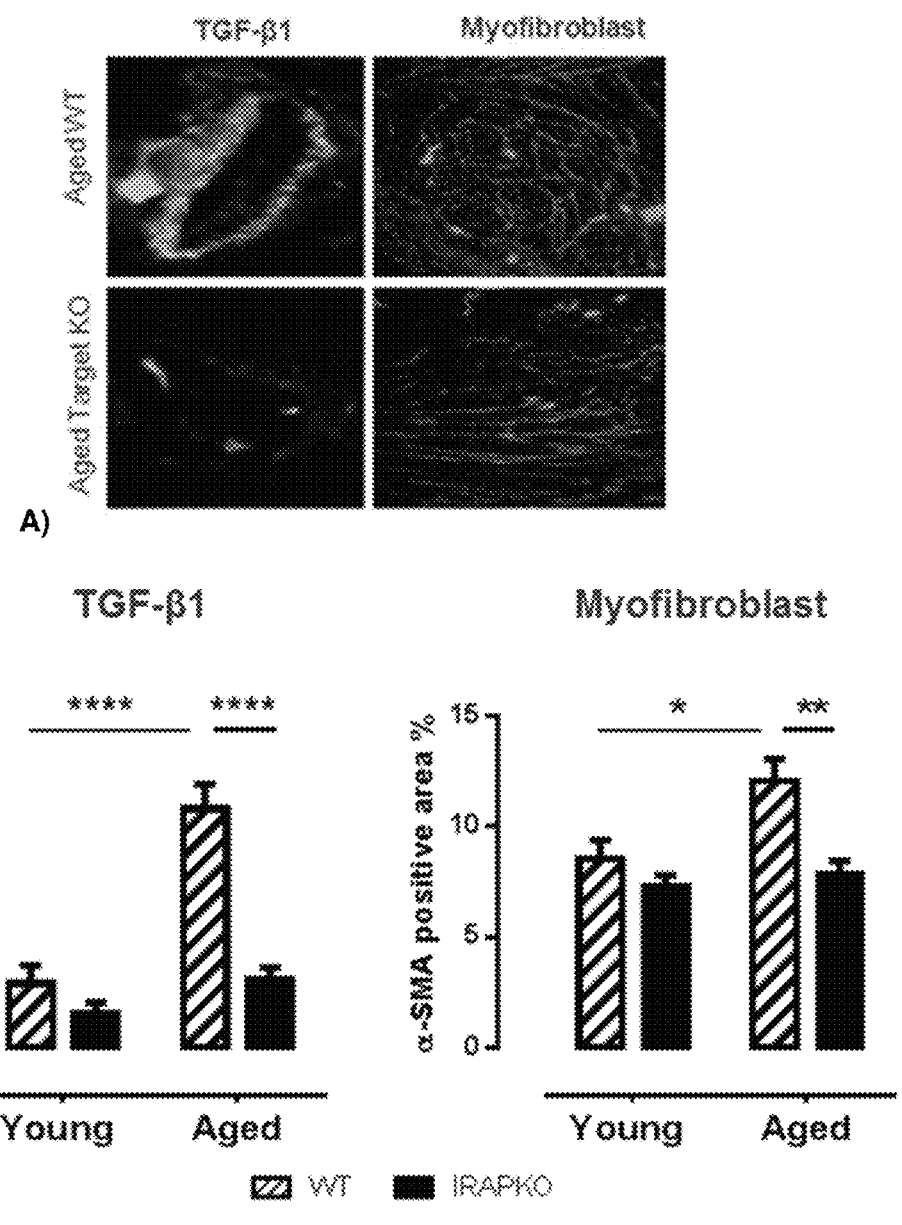

FIG. 12: IRAP$^{-/-}$ mice do not have age-induced increase in TGF-$\beta_1$ and αSMA-expressing myofibroblasts compared to WT mice. (a) Representative images of perivascular expression of TGF-$\beta_1$ and α-SMA-expressing myofibroblasts via immunofluorescence staining of transverse heart sections from aged WT or IRAP$^{-/-}$ mice. (b) Quantification of positive stained area for TGF-$\beta_1$ and α-SMA expressed as percent positive stained tissue area (n=5-9). Data expressed as mean±s.e.m; *P<0.05, P<0.01, **P<0.0001 determined by two way analysis of variance (ANOVA)

Figure 13:
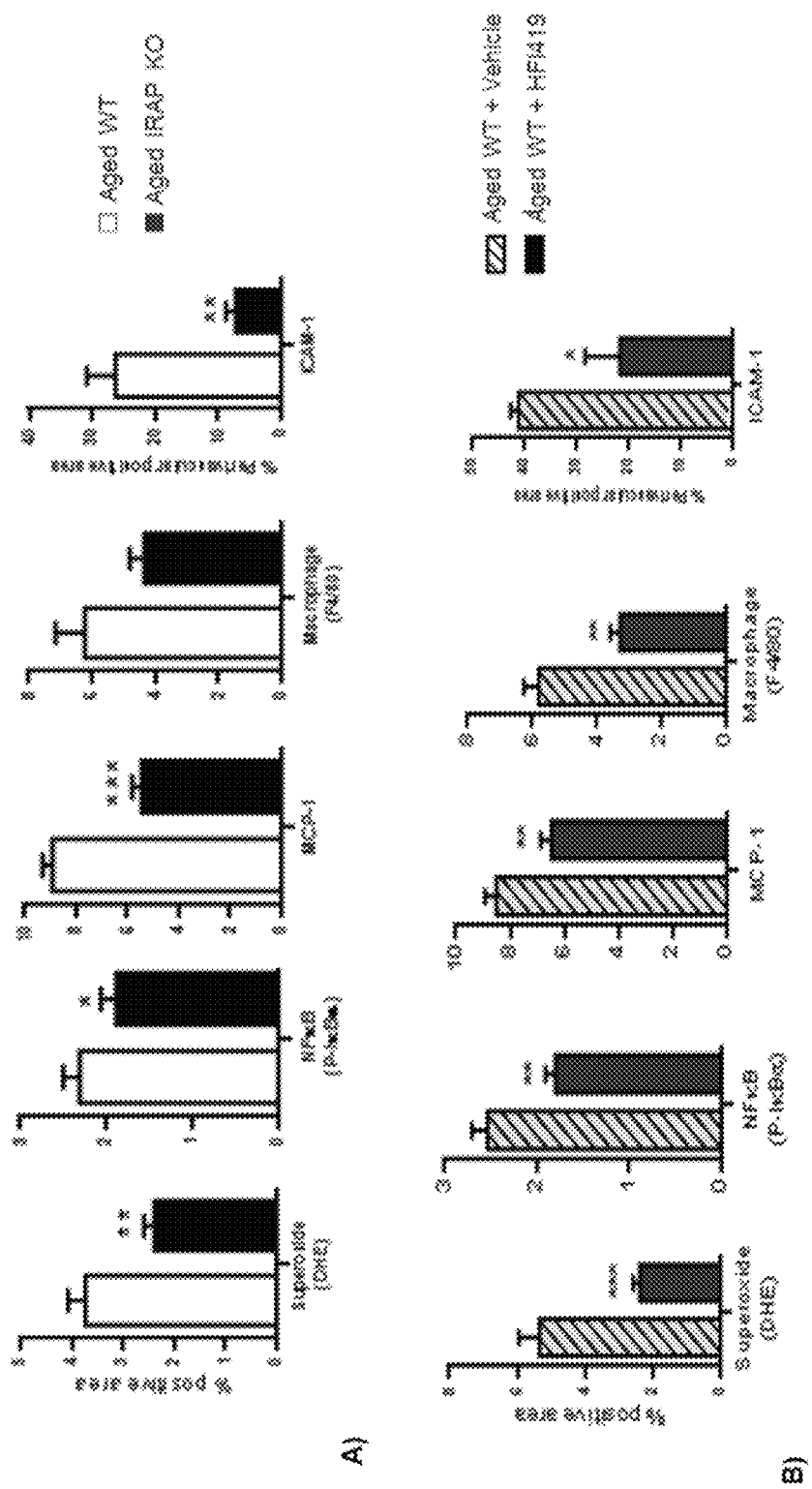

FIG. 13: IRAP deficiency and IRAP inhibitor treatment reduces inflammatory markers in aged mice. (a) Aged IRAP deficient mice demonstrated reduced superoxide expression (using DHE staining), decreased NFκB activation (measured via phospho-IκBα expression using immunofluorescence staining), reduced monocyte chemoattractant protein-1 (MCP-1 via immunofluorescence), reduced macrophage expression (using F4/80 immunofluorescence) and reduced perivascular expression of intercellular adhesion molecule-1 (ICAM-1 via immunofluorescence) in transverse cardiac sections when compared to that seen in cardiac sections taken from aged WT mice (n=6); Data expressed as mean s.e.m; *P<0.05; P<0.01; *P<0.001 determined by unpaired t-test. (b) 4 week chronic IRAP inhibitor treatment of aged (~20 months) WT mice reduced superoxide expression (using DHE staining), decreased NFκB activation (measured via phospho-IκBα expression using immunofluorescence staining), reduced monocyte chemoattractant protein-1 (MCP-1 using immunofluorescence), reduced macrophage expression (using F4/80 immunofluorescence) and reduced perivascular expression of intercellular adhesion molecule-1 (ICAM-1 via immunofluorescence) in transverse cardiac sections when compared to that seen in cardiac sections from aged vehicle-treated WT mice (n=6-8); Data expressed as mean±s.e.m; *P<0.05; P<0.01; *P<0.001 determined by unpaired t-test.

Figure 14:
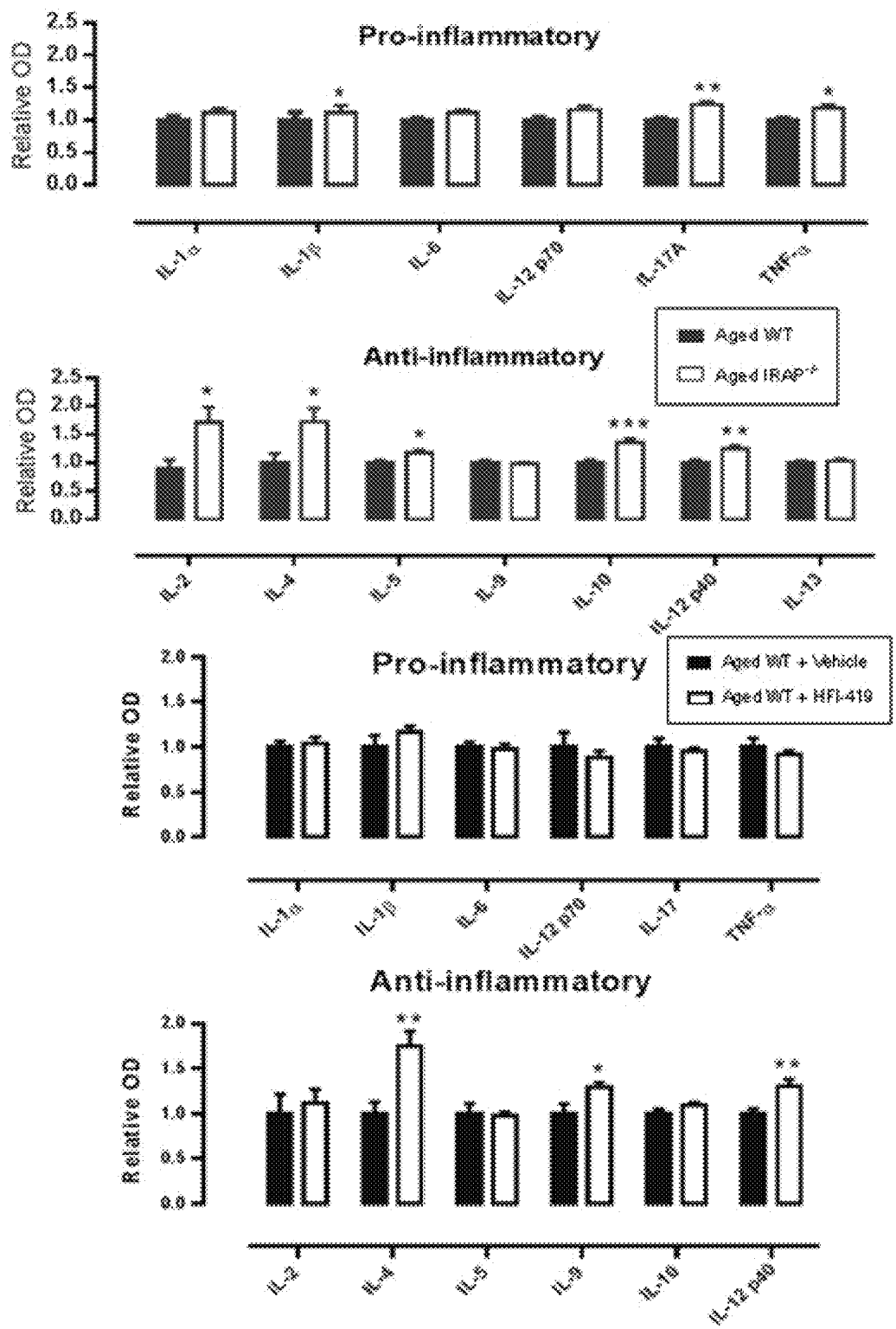

FIG. 14: Cytokine quantification was performed in hearts from aged WT (n=9) and IRAP$^{-/-}$ (n=9) mice (a,b) and from aged vehicle—(n=6) and HFI-419—(n=9) treated mice (c,d) using Bio-Plex multiplex assay. Cytokines are grouped based on pro-inflammatory and anti-inflammatory phenotypes with concentration of cytokines in the heart expressed as relative ratio to aged WT control; exact fold change presented in Table 1. All data expressed as mean s.e.m; *P<0.05; P<0.01; *P<0.001, determined by unpaired t-test.

Figure 15:
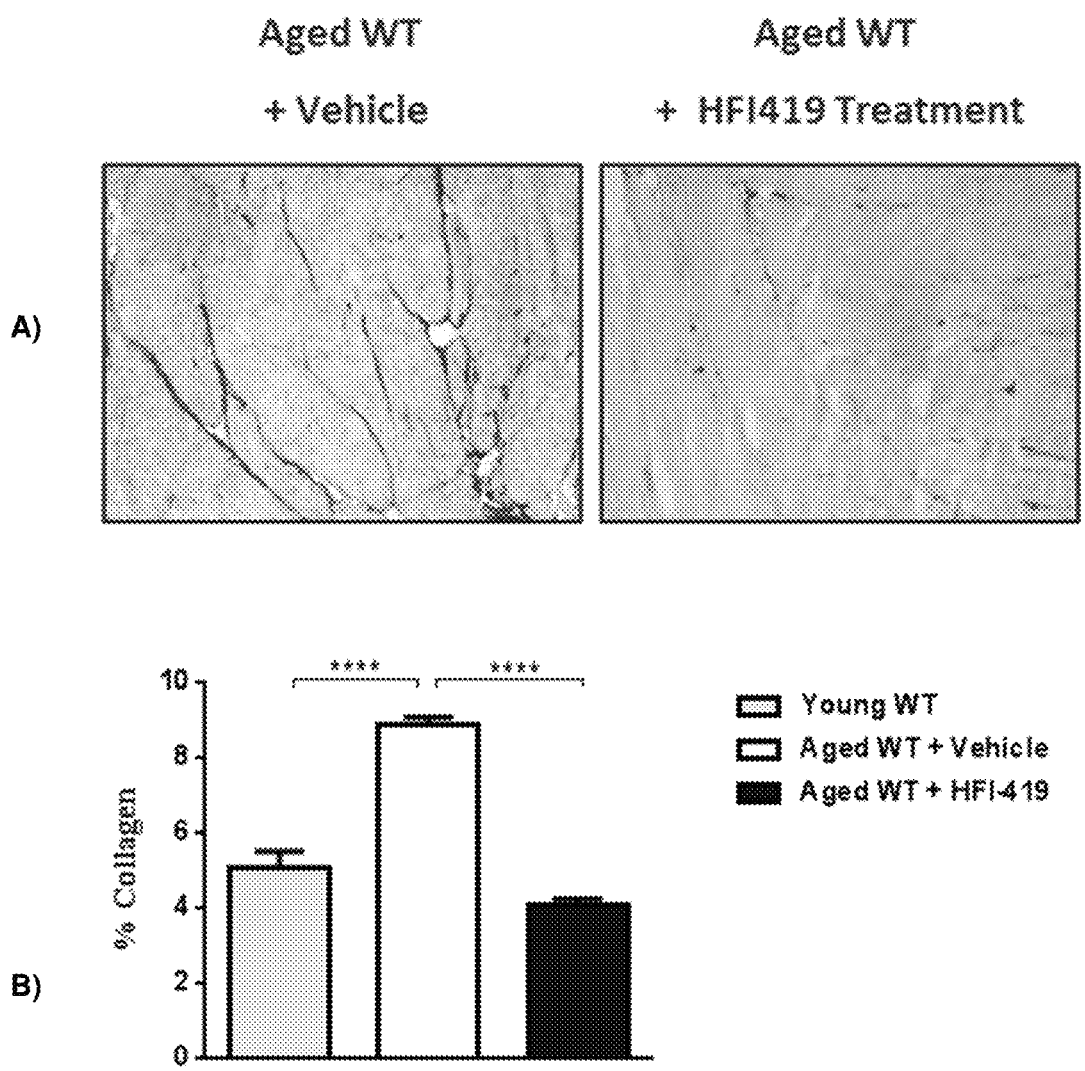

FIG. 15: Chronic IRAP inhibitor treatment completely reverses age-induced cardiac fibrosis. (a) Representative images of picrosirius red stained collagen in transverse heart sections of aged (18-22 month old) WT mice treated with vehicle or HFI-419 (500 ng/kg/min; s.c.). (b) Quantification of positive stained area for interstitial collagen, under bright field microscopy, expressed as percent positive stained tissue area (n=5-8). Data expressed as mean±s.e.m; ****P<0.0001 determined by one way analysis of variance (ANOVA). Analogous data for interstitial collagen measured under polarized light microscopy are depicted in FIG. 16f.

Figure 16:
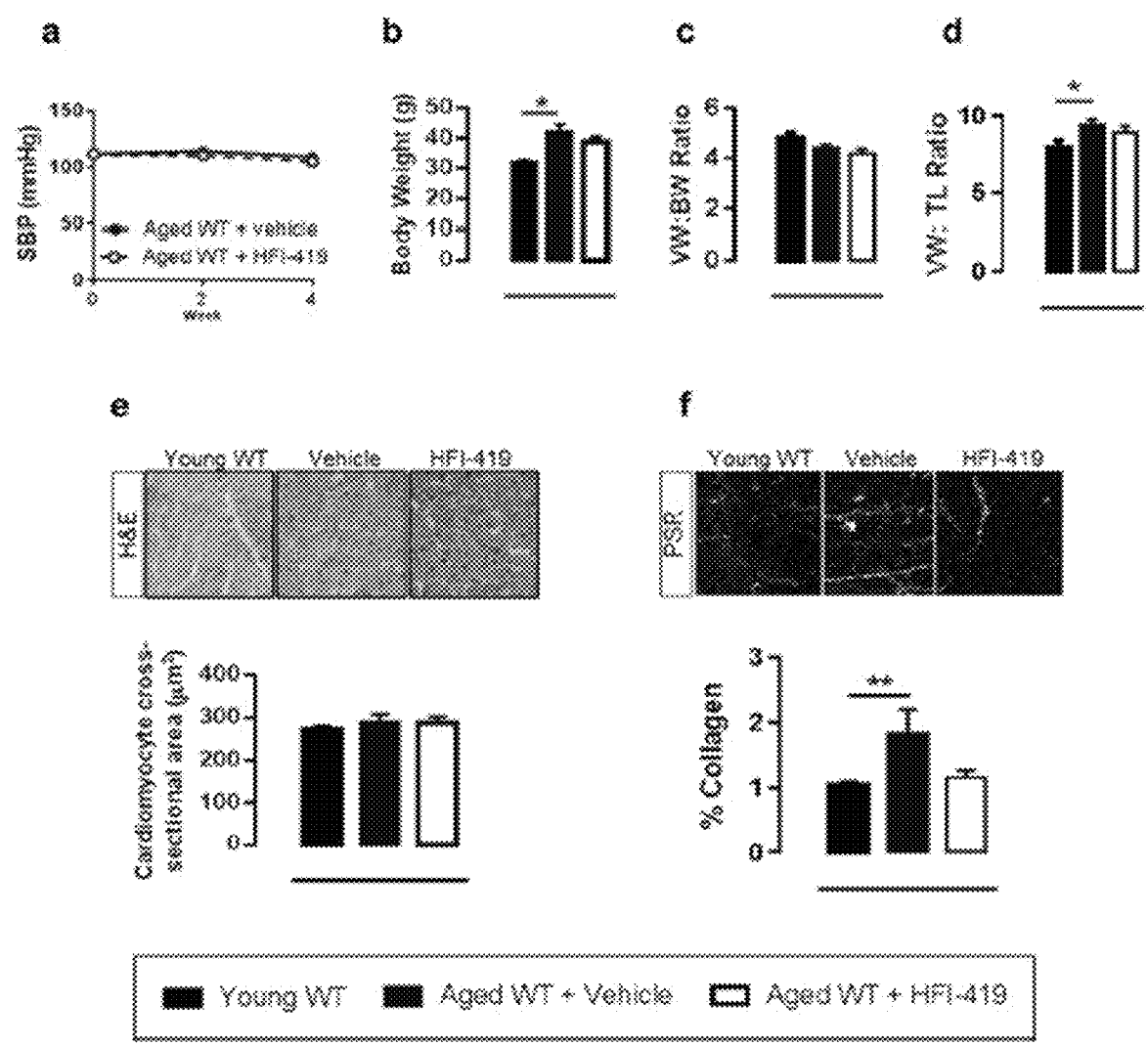

FIG. 16: Effect of chronic (4 week) pharmacological inhibition of IRAP with HF1419 in aged mice. Chronic IRAP inhibition had no significant effect on systolic blood pressure, SBP (a), body weight (b) and gross measures of cardiac hypertrophy assessed using (c) ventricular weight to body weight ratio, VW:BW or (d) ventricular weight to tibial length ratio, VW:TL, although age generally increased these variable compared with young WT mice. IRAP inhibition had no effect on cardiomyocyte cross-sectional area when quantified using H&E stained heart sections (e), while IRAP inhibition significantly decreased interstitial collagen expression to those levels observed in young WT mice (f), determined via polarized microscopy of picrosirius red stained heart cross-sections. Aged vehicle-treated mice: n=10 and aged HFI-419-treated mice, n=10; Data expressed as mean±s.e.m; *P<0.05, **P<0.001, determined by one-way ANOVA.

Figure 17:
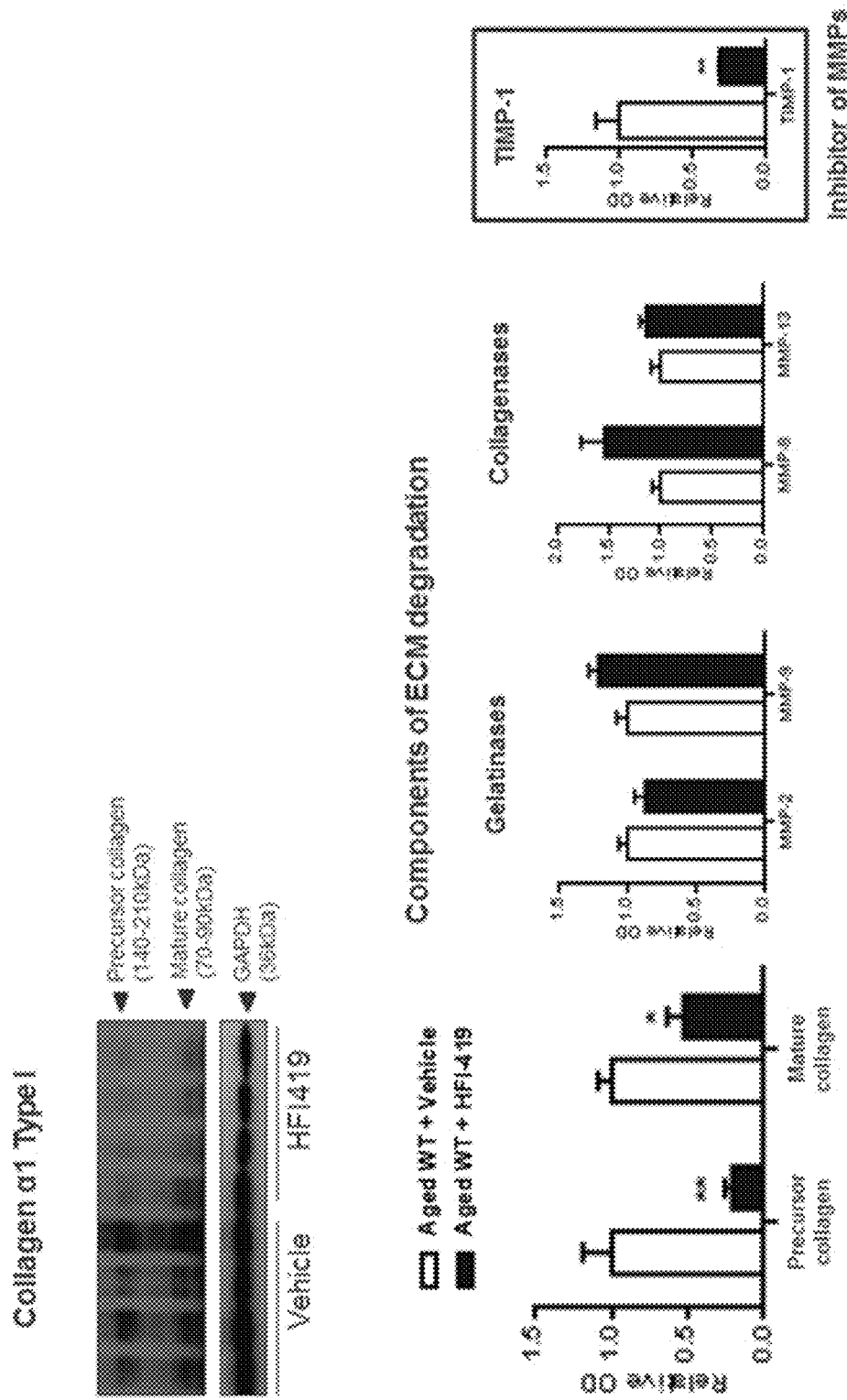

FIG. 17: Chronic IRAP inhibitor treatment alters age-induced extracellular matrix balance. Western blots and densitometric quantification of protein expression of precursor and mature collagen, matrix metalloproteinase (MMP)-2, MMP-8, MMP-9, MMP-13 and TIMP-1 in cardiac tissue from aged vehicle and HFI-419 treated WT mice expressed as relative ratio to mean of vehicle-treated WT control s.e.m; (n=4 in all groups). *P<0.05, **P<0.01, determined by unpaired t-test.

Figure 18:
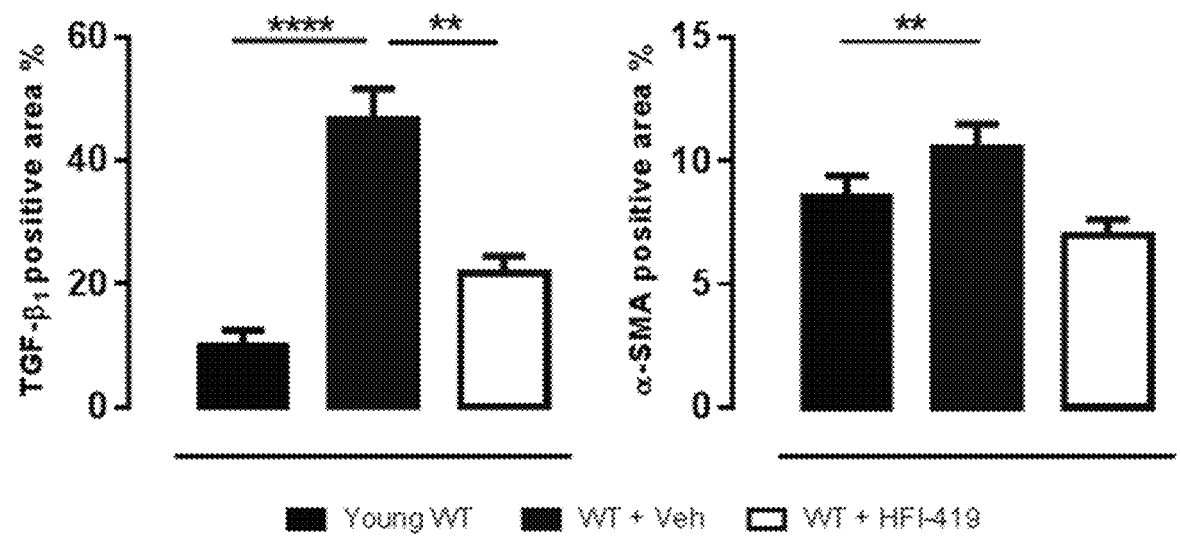

FIG. 18: Chronic IRAP inhibition with HFI-419 in aged WT mice significantly decreased levels of TGF-$\beta_1$ and α-SMA-expressing myofibroblasts compared to vehicle-treated aged WT mice. Quantification of positive stained area for TGF-$\beta_1$ and α-SMA expressed as percent positive stained tissue area (n=5-8). Data expressed as mean s.e.m; P<0.01, **P<0.0001 determined by one way analysis of variance (ANOVA).

Figure 19:
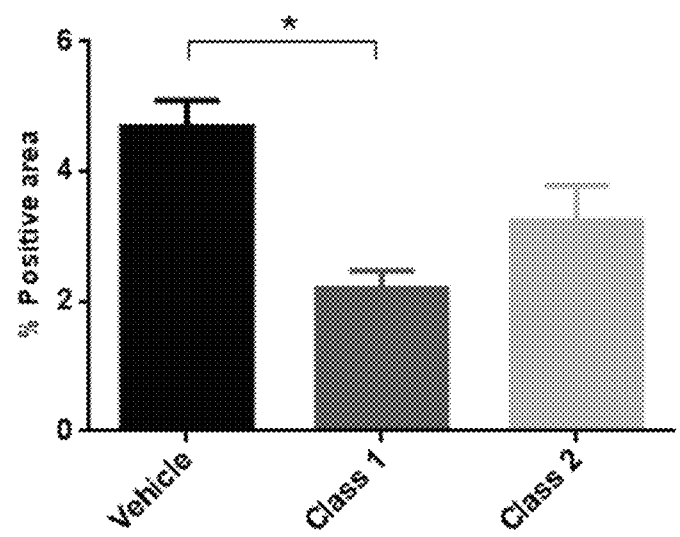

FIG. 19: Effect of two structurally distinct IRAP inhibitors to reverse age-induced cardiac fibrosis. Aged (~20 month old) WT mice were chronically treated with vehicle, compound 1 (denoted as Class 1) or compound 2 (denoted Class 2) for 4 weeks. Picrosirius red staining of transverse heart sections from each of these groups demonstrated clear reversal of age-induced cardiac fibrosis (n=3). Data expressed as mean±s.e.m of percentage positive stained area. *P<0.05; determined by one way ANOVA with Bonferroni correction for multiple comparisons.

Figure 20:
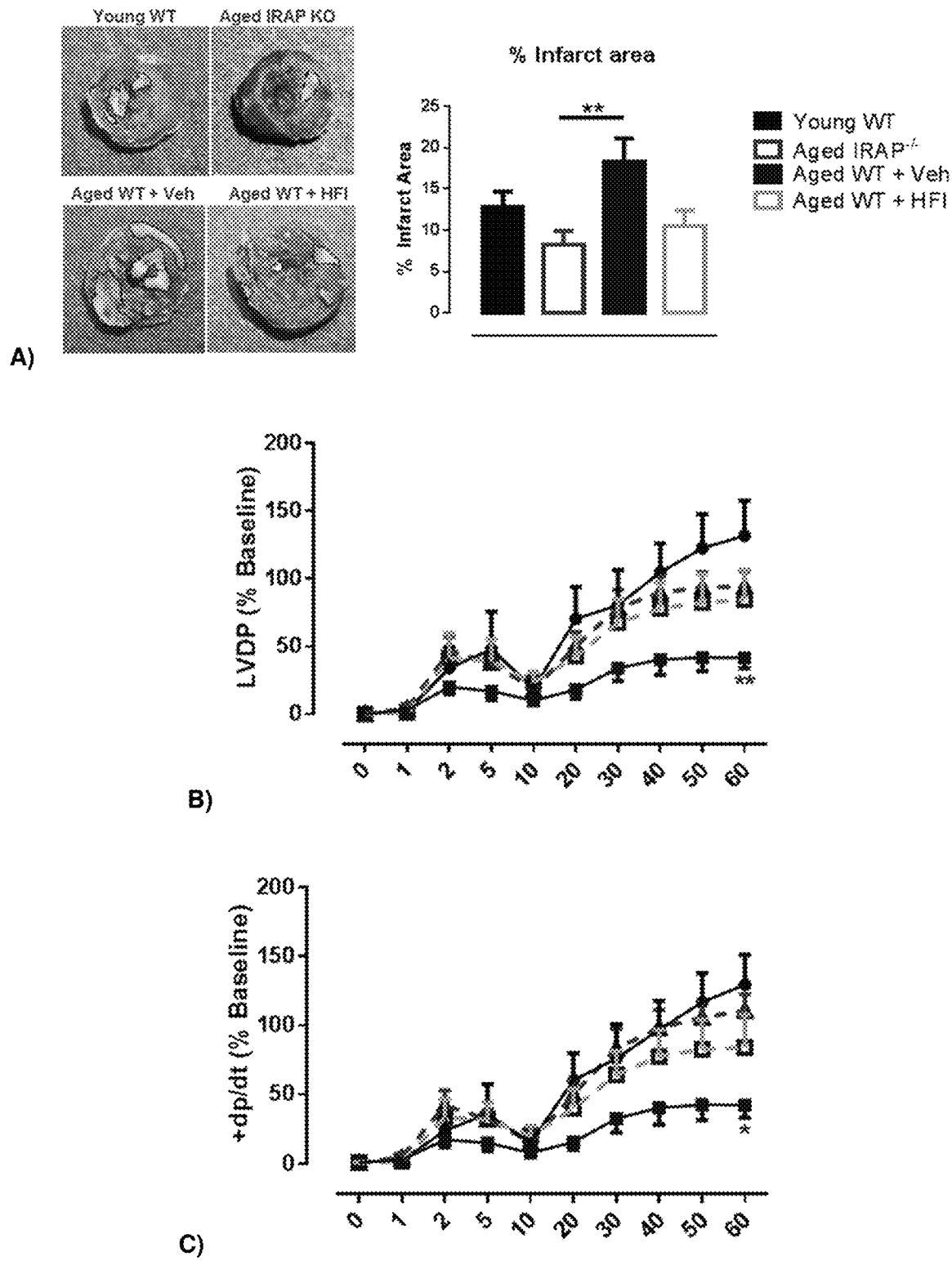
Figure 20:
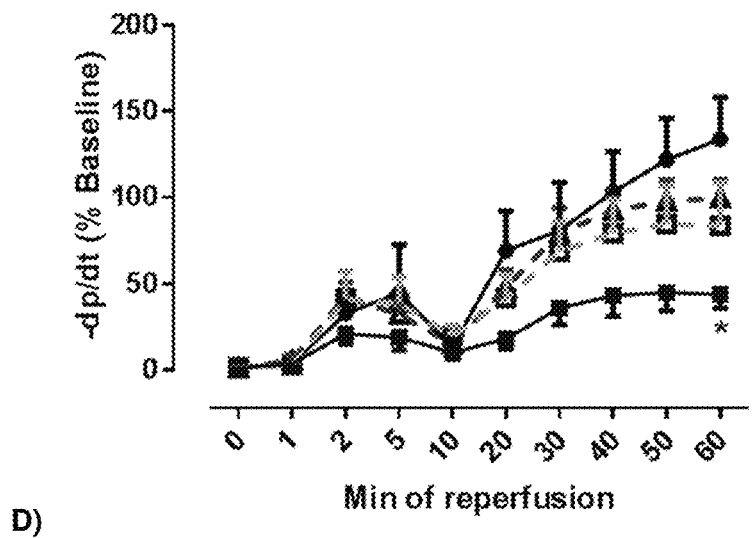
Figure 20:
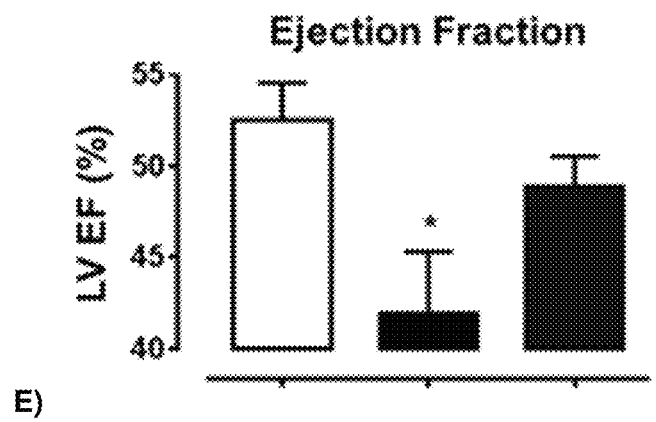
Figure 20:
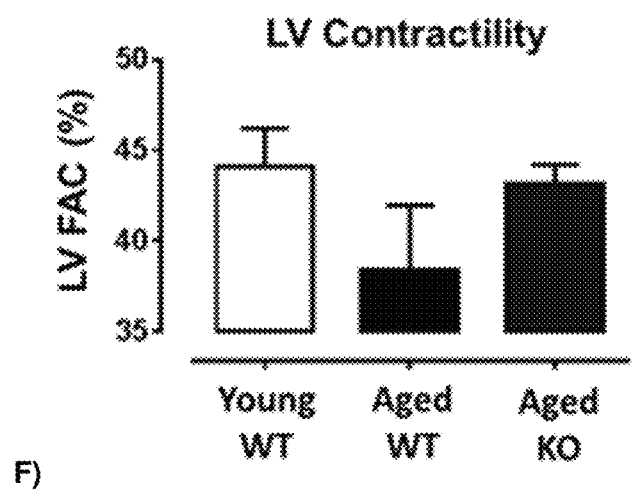

FIG. 20: Genetic deletion and pharmacological inhibition of IRAP improve heart function and decrease infarct area following ischemic-reperfusion (I/R) injury. Heart function measurements were performed using the isolated Langendorff heart preparation with a 40 minute ischaemic/1 hour reperfusion injury (IR, ischaemic reperfusion). Hearts were stopped in diastole by placing in high potassium solution (PSS; 100 mM) for 3 minutes, after which they were sliced and stained with TTZ. Representative images showing infarct area from each group are shown in (a). Infarct area appears white and is outlined within the dotted line region. Infarct area is quantified as percentage stained area across both superior and inferior surfaces of 5-7 heart slices from young WT (n=7), aged IRAP$^{-/-}$ (n=10), aged vehicle-treated (n=8) or HFI-419 treated (n=8) WT mice. Data expressed as mean s.e.m, **P<0.01 determined by one way ANOVA. IRAP deficiency or chronic IRAP inhibition improved recovery of left ventricular developed pressure (LVDP) (b), rate of left ventricular contraction (+dp/dt) (c) and rate of left ventricular relaxation (−dp/dt) (d) following ischemic injury. Data expressed as mean±s.e.m. *P<0.05, P<0.01 was determined using two-way ANOVA with post hoc Bonferroni test on LVDP and ±dp/dt. Echocardiography studies were performed in aged (~22 month old) WT and IRAP−/− mice with cardiac function compared to that of young (3 month old) WT mice. Aged WT mice (n=5) had a significant reduction in left ventricular ejection fraction (LVEF) (e) and a trend towards reduced LV contractility (f) compared to young WT mice (n=5) with aged IRAP−/− mice (n=4) protected against these age-induced changes in cardiac function. Data expressed as mean±s.e.m, P<0.01 determined by one way ANOVA.

Figure 21:
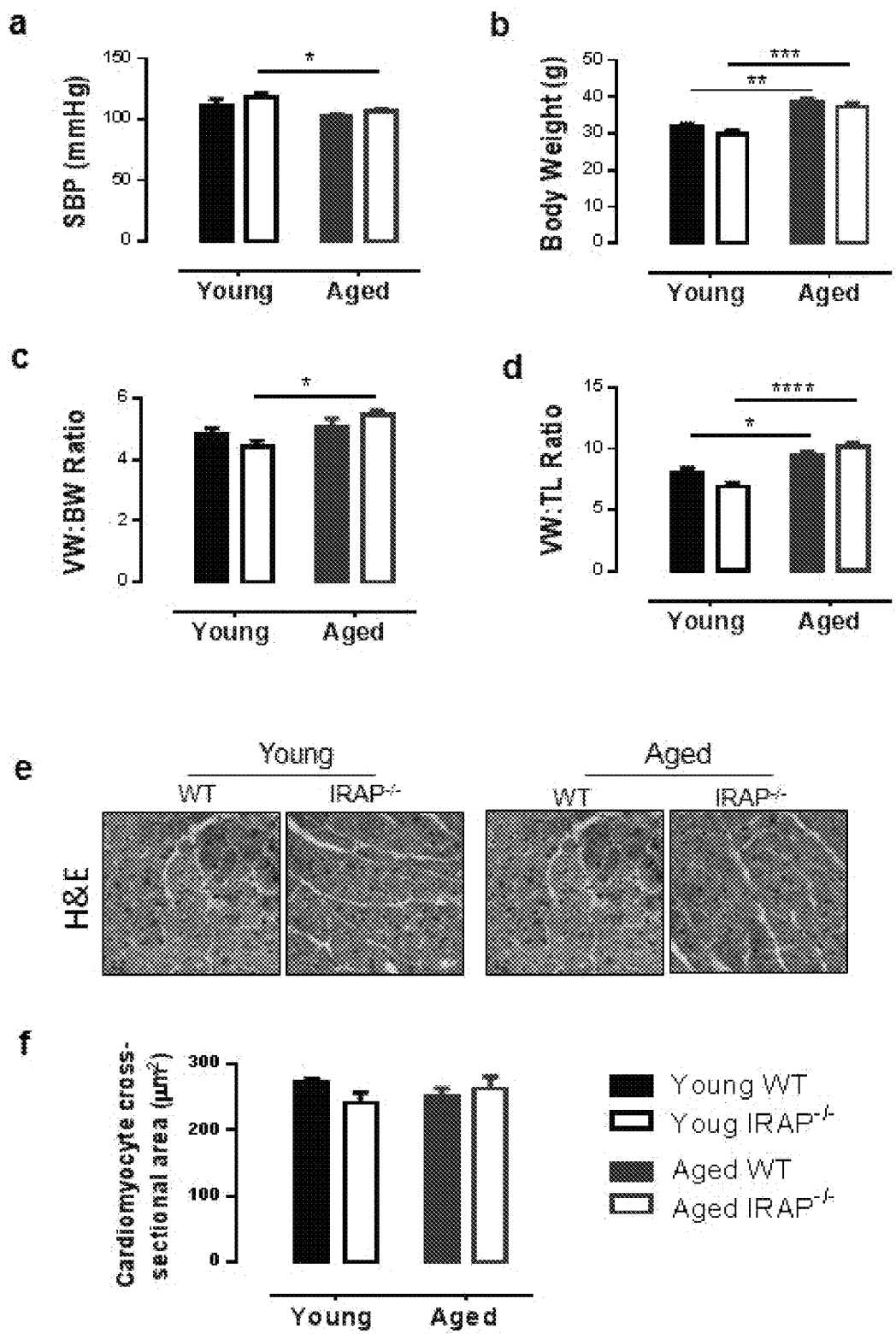

FIG. 21: Phenotypic differences between WT and IRAP deficient mice at 6 months and ~22 months of age. There was minimal effect of age and genotype on systolic blood pressure, SBP when compared at young (~5 months old) and aged (~20 months old) time points (a). As expected, there were increases in body weight of WT and IRAP$^{-/-}$ mice associated with aging (b). Gross measures of cardiac hypertrophy using (c) ventricular weight to body weight ratio, VW:BW or (d) ventricular weight to tibial length ratio, VW:TL, found a significant effect of aging to increase the VW:BW ratio in IRAP$^{-/-}$ mice as well as the VW:TL ratio in both strains that was largely independent of genotype. Cardiac hypertrophy was further assessed using cross-sectional cardiomyocyte area measurement. Representative images of cardiomyocytes in H&E-stained heart sections are shown in (e) with quantification of cardiomyocyte cross-sectional area performed in 6 fields of view per heart section (f). Data are expressed as mean±s.e.m; *P<0.05, P<0.01, *P<0.001, ****P<0.0001 determined by two way analysis of variance (ANOVA) (Young mice: Wt, n=8 and IRAP$^{-/-}$, $^n$=10; Aged mice: WT, n=16 and IRAP$^{-/-}$, n=16).

Figure 22:
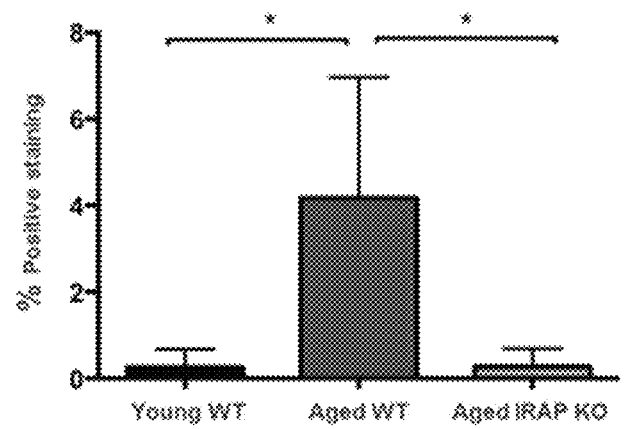
Figure 22:
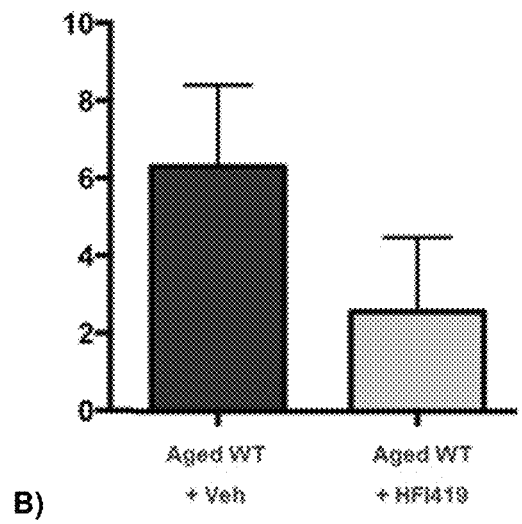

FIG. 22: IRAP expression is increased in kidneys from aged (~20 month old) WT mice and decreased after pharmacological inhibition with an IRAP inhibitor. (a) Quantification of IRAP expression in 5 μm thick coronal kidney sections from adult (4-6 month old) and aged (18-22 month old) WT and IRAP$^{-/-}$ mice (n=4). (b) Quantification of IRAP expression in 5 μm thick coronal kidney sections from aged (18-22 month old) WT mice treated for 4 weeks with vehicle or HFI-419 (500 ng/kg/min; s.c.; n=4). IRAP inhibitor treatment tended to decrease IRAP expression compared to vehicle-treated aged controls. Quantification of IRAP expressed as percent positive stained tissue area. Data expressed as mean±s.e.m; *P<0.05 determined by one way analysis of variance (ANOVA) (a) or unpaired t-test (b).

Figure 23:
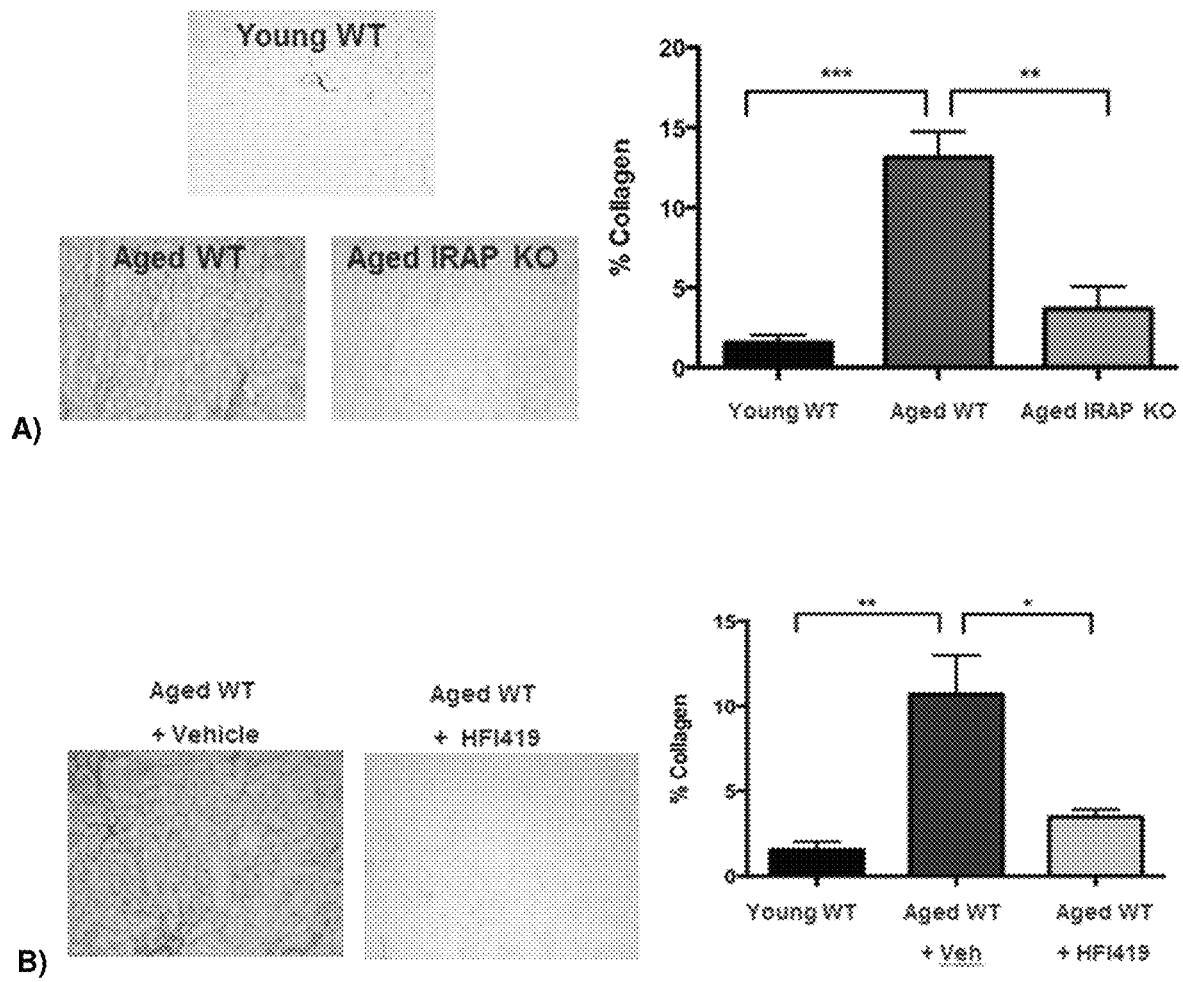

FIG. 23: Effect of IRAP deficiency or IRAP inhibition on development of age-induced kidney fibrosis. (a) Representative images and quantification of picrosirius red stained interstitial collagen in coronal kidney sections of adult (4-6 month old) and aged (18-22 month old) WT and aged IRAP$^{-/-}$ mice demonstrating IRAP deficiency prevents age-induced increase in interstitial kidney fibrosis (n=4). (b) Representative images and quantification of picrosirius red stained interstitial collagen in coronal kidney sections of aged (18-22 month old) vehicle and HFI-419 treated WT mice demonstrating IRAP inhibition reverses age-induced increase in interstitial kidney fibrosis (n=4). Data expressed as percent positive stained tissue area. Data expressed as mean±s.e.m; *P<0.05, P<0.01, *P<0.001 determined by one way analysis of variance (ANOVA) (a) or unpaired t-test (b).

Figure 24:
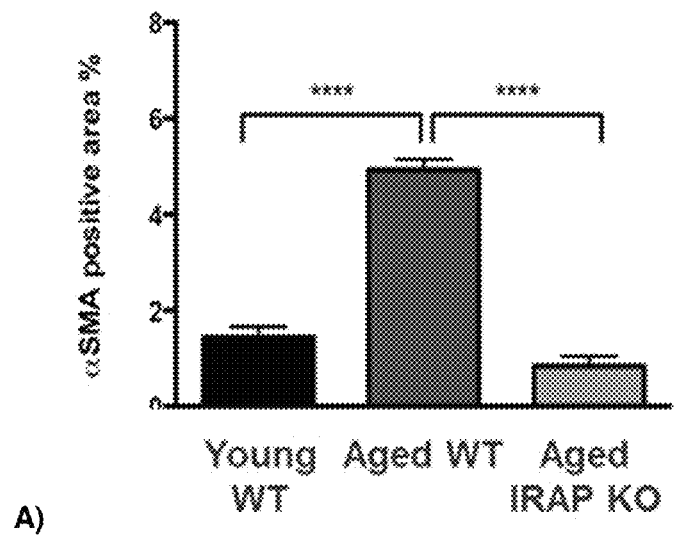
Figure 24:
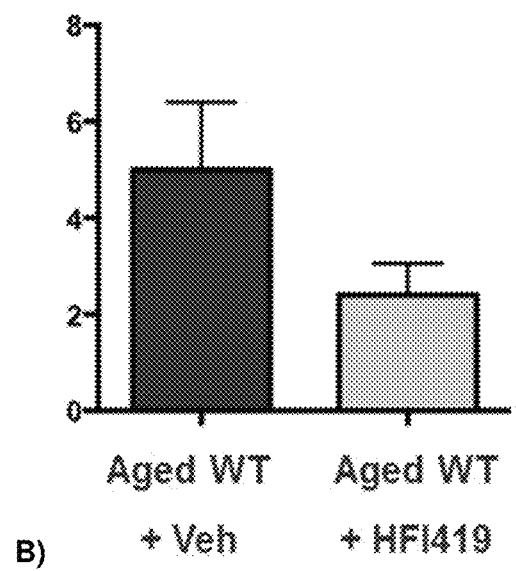

FIG. 24: IRAP deficiency and IRAP inhibition prevent or reverse, respectively, age-induced increase in α-SMA-expressing myofibroblasts compared to age-matched controls. (a) Quantification of positive stained area for α-SMA-expressing myofibroblasts via immunofluorescence staining of coronal kidney sections from adult (4-6 month old) and aged (18-22 month old) WT and aged IRAP$^{-/-}$ mice. α-SMA expressed as percent positive stained tissue area with data expressed as mean±s.e.m (n=4); ****P<0.0001 determined by one way analysis of variance (ANOVA). (b) Quantification of positive stained area for α-SMA-expressing myofibroblasts via immunofluorescence staining of coronal kidney sections from aged (18-22 month old) vehicle and HFI-419 treated WT mice. α-SMA expressed as percent positive stained tissue area with data expressed as mean±s.e.m (n=4).

Figure 25:
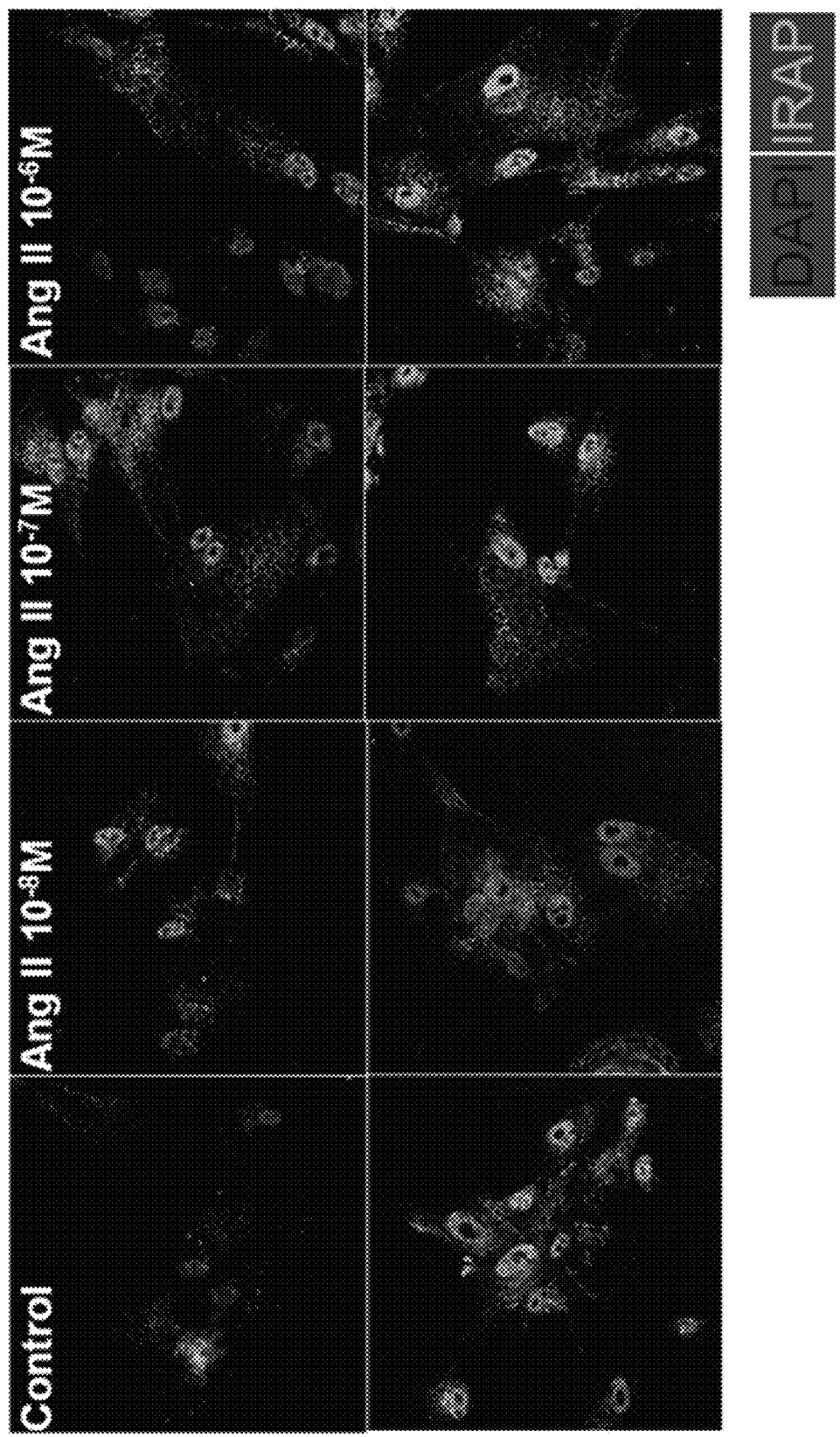

FIG. 25: Increased IRAP expression in human cardiac fibroblasts stimulated with Angiotensin II. Representative images showing primary human cardiac fibroblasts stimulated with increasing concentrations of Ang II induced an increase in expression of IRAP.

Figure 26:
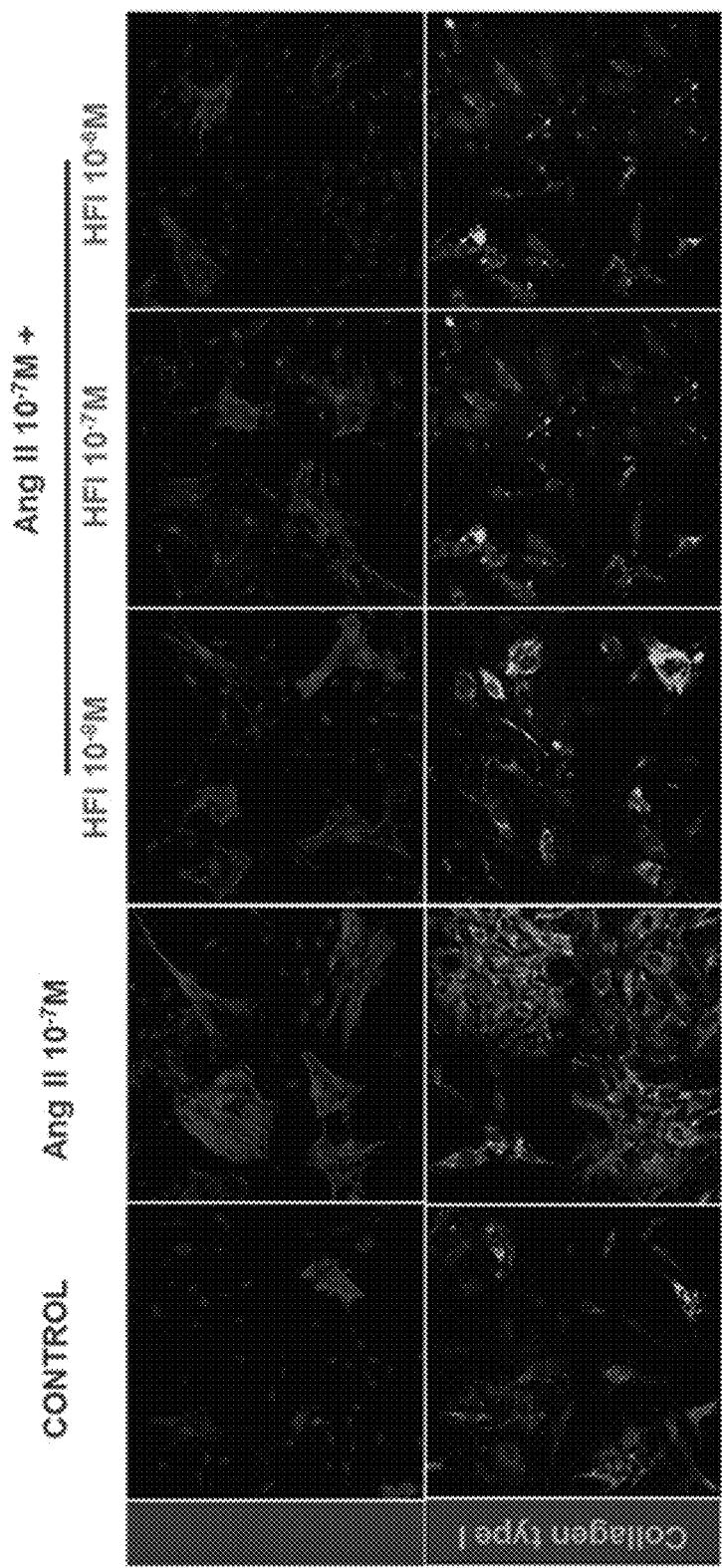
Figure 26:
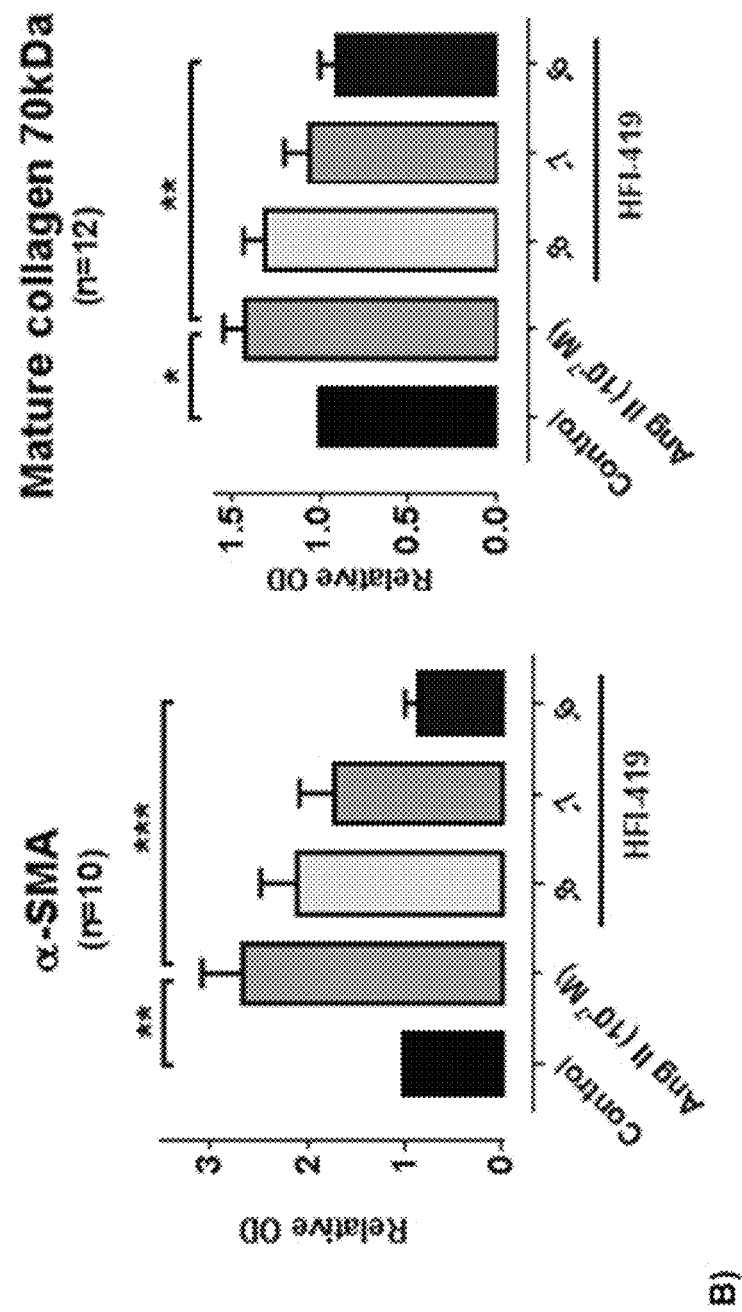

FIG. 26: IRAP inhibitor dose-dependently decreased α-SMA and collagen expression in human cardiac fibroblasts. (a) Representative images showing increased expression of α-SMA (red; marker for myofibroblasts) and collagen (green) when human cardiac fibroblasts (HCFs) were stimulated with Ang II (0.1 μM). Combined Ang II and HFI-419 treatment (0.01 to 1 μM) decreased α-SMA and collagen expression. (b) Quantitative data from western blots confirming dose-dependent decrease in protein expression of α-SMA and collagen when HCFs were co-treated with Ang II+ increasing concentrations of HFI-419 (n=10-12). Data expressed as mean±s.e.m; densitometric analysis of western blots expressed as relative ratio to mean of control cells ±s.e.m; *P<0.05; P<0.01; *P<0.001 determined by one way ANOVA with Bonferroni correction for multiple comparisons.

Figure 27:
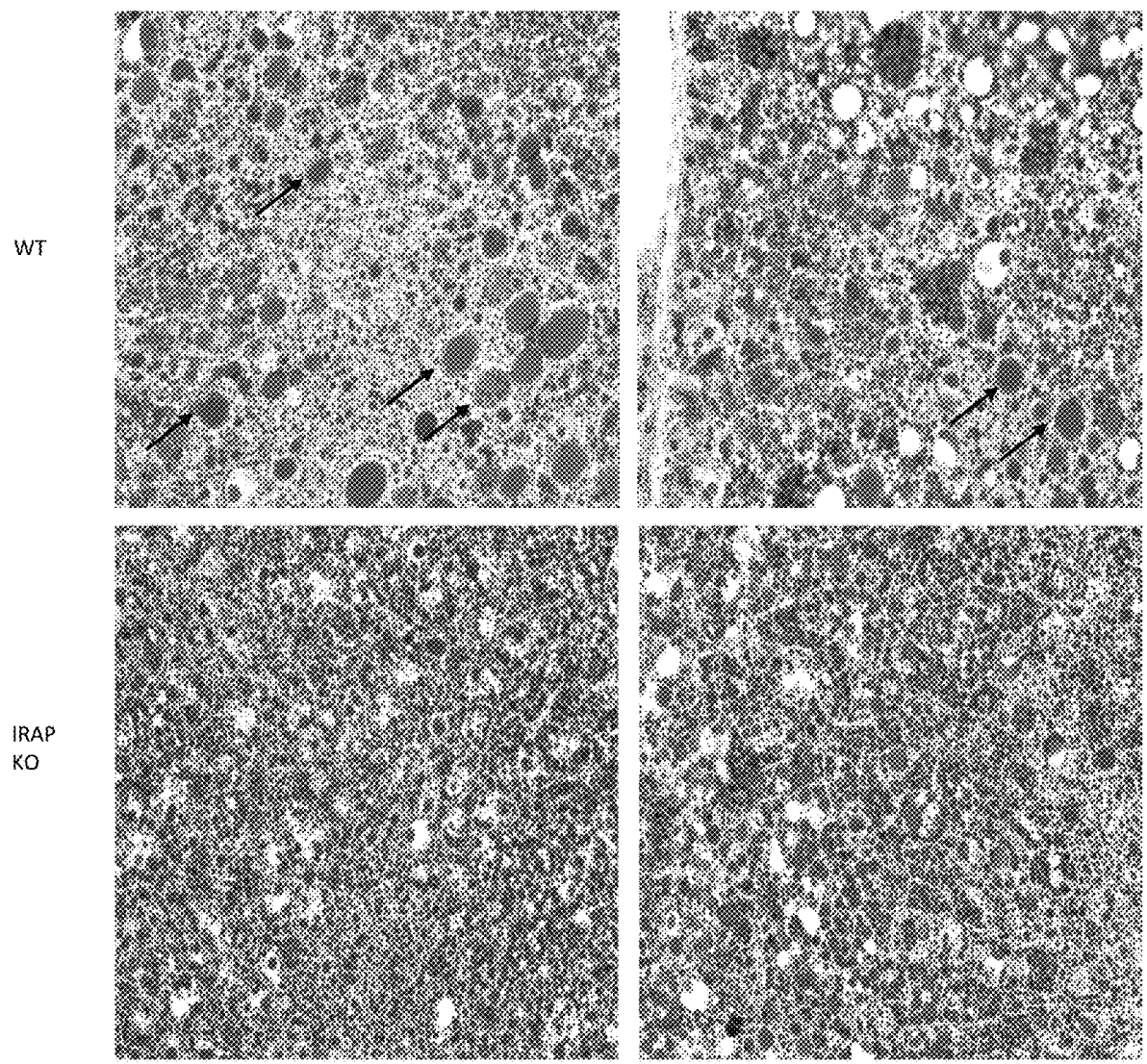

FIG. 27: Liver sections from WT (top panels) and IRAP KO (bottom panels) mice stained with OilRedO to indicate steatosis. The liver sections from WT mice displayed greater macrovesicular steatosis indicated by the arrows.

Figure 28:
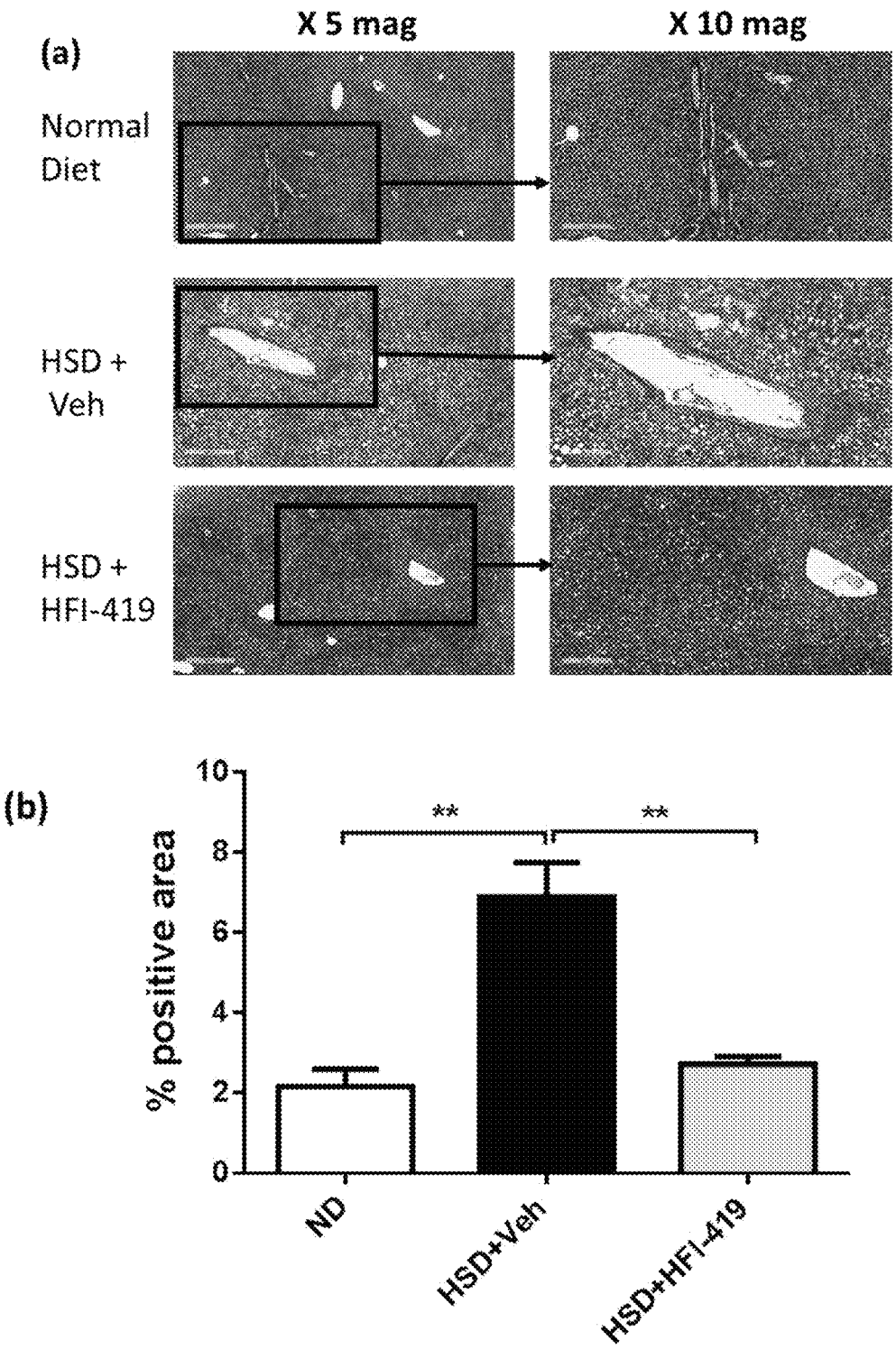

FIG. 28: Chronic IRAP inhibitor treatment reverses HSD-induced liver fibrosis. (a) Representative images of masson trichrome stained collagen in liver sections of WT mice treated normal diet (ND) or high salt diet (HSD)+ vehicle or HFI-419 (500 ng/kg/min; s.c.). (b) Quantification of positive stained area for collagen, under bright field microscopy, expressed as percent positive stained tissue area (n=3). Data expressed as mean±s.e.m; **P<0.01 determined by one way analysis of variance (ANOVA).

DETAILED DESCRIPTION OF THE EMBODIMENTS

It will be understood that the invention disclosed and defined in this specification extends to all alternative combinations of two or more of the individual features mentioned or evident from the text or drawings. All of these different combinations constitute various alternative aspects of the invention.

Reference will now be made in detail to certain embodiments of the invention. While the invention will be described in conjunction with the embodiments, it will be understood that the intention is not to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described. It will be understood that the invention disclosed and defined in this specification extends to all alternative combinations of two or more of the individual features mentioned or evident from the text or drawings. All of these different combinations constitute various alternative aspects of the invention.

All of the patents and publications referred to herein are incorporated by reference in their entirety.

For purposes of interpreting this specification, terms used in the singular will also include the plural and vice versa.

The inventors have identified the enzyme, insulin regulated aminopeptidase (IRAP; also known as the angiotensin subtype 4 receptor—$AT_4R$, placental leucine aminopeptidase or oxytocinase) as a novel target to combat fibrosis. It is proposed that Ang IV binds to IRAP and acts to inhibit the catalytic activity of this enzyme, however as yet there are no chronic studies exploring the potential benefits of IRAP inhibition in the context of cardiovascular disease. The inventors hypothesized that removal or blockade of IRAP activity would protect against age-mediated increases in cardiac fibrosis and inflammation, or other cardiovascular disease-related or tissue injury related organ fibrosis, to improve cardiac and vascular function. The inventors tested this hypothesis in (i) a prevention model of aged male WT and IRAP$^{-/-}$ mice (18-22 month old), (ii) a prevention model using Ang II infusion to induce fibrosis and inflammation in multiple organs, and in (iii) an intervention model by administering a small molecule inhibitor of IRAP to aged WT mice with established cardiovascular pathologies, in order to reverse CVD. The inventors found that IRAP deficiency or pharmacological inhibition of IRAP protected against and, more importantly, reversed age- or injury-induced organ fibrosis (e.g. in heart and kidneys) to the level exhibited in young mice, in part by inhibiting synthesis and enhancing degradation of collagen. In addition, IRAP inhibition decreased cardiac ROS (reactive oxygen species) and inflammatory mediators downstream of NFκB, collectively pushing towards an anti-inflammatory phenotype thus contributing to overall cardiac and vascular improvement in aging. A similar anti-fibrotic and anti-inflammatory phenotype was also shown in IRAP−/− mice and by pharmacological IRAP inhibition in mice treated with Ang II to induce cardiovascular pathologies such as organ fibrosis and inflammation.

The present invention is based on results described herein where inhibition of IRAP was confirmed as having a role in fibrotic disease, particularly age-induced fibrotic disease, using IRAP deficient mice or pharmacological inhibition with an IRAP inhibitor. The inventors demonstrated that IRAP-deficient mice were protected from fibrosis and further, that those mice with experimentally induced or age related fibrosis that were administered an IRAP inhibitor were successfully treated for fibrosis, as demonstrated by a consistent ability of IRAP inhibitors to reduce fibrosis and the expression of fibrogenic mediators.

An advantage of the invention is the surprising finding that treatment with an inhibitor of IRAP at the time of established fibrotic disease leads to a reversal of fibrosis. Pharmacological inhibition of IRAP therefore not only has the effect of halting progression of fibrosis, such as age- or injury-induced fibrosis, but reversing the existing symptoms, such as collagen deposition. The invention therefore finds particular application to subjects that are diagnosed with fibrosis, such as age-induced fibrosis or for cardiovascular diseases that are often associated with organ fibrosis. Further, reversing the hallmarks of age-induced fibrosis indicates that the invention can be applied to subjects with advanced fibrosis.

As used herein, an "IRAP inhibitor" or "inhibitor of IRAP" is any compound that inhibits the activity of IRAP (IRAP; also known as the angiotensin subtype 4 receptor—$AT_4R$, placental leucine aminopeptidase or oxytocinase). Inhibition of activity of IRAP may also include a reduction in the level or amount of IRAP protein, RNA or DNA in a cell. The compound may be a competitive, non-competitive, orthosteric, allosteric, or partial inhibitor. In a preferred form the compound is a molecule that inhibits the enzyme activity of IRAP for example by binding the active site, or competing with the enzyme substrate or co-effector or signalling mechanism. In a preferred form the compound is a molecule that inhibits the activity of IRAP by disrupting the signalasome or any other protein-protein interaction required for the activity of IRAP.

The inhibitor may be specific for IRAP and only have some low level inhibitory activity against other receptors (for example, a Ki of greater than about 50 μM or 100 μM, preferably 1 mM against other receptors as measured using an assay as described herein, or for example a Ki against other receptors at least 10× greater than the Ki against IRAP). Preferably, the inhibitor of IRAP is a substance that limits the activity of IRAP to 10% or less in comparison with control. Control is a solvent, in which the inhibitor is tested, used at the same quantity, however, without the inhibitor. The enzymatic activities of IRAP may be determined by the hydrolysis of the synthetic substrate Leu-MCA (Sigma-Aldrich, Missouri, USA) monitored by the release of a fluorogenic product, MCA, at excitation and emission wavelengths of 380 and 440 nm, respectively according to Albiston et al. 2008 The FASEB Journal 22:4209-4217 or other method described herein. In preferred forms, the inhibitor may be a small molecule chemical compound or interfering RNA (e.g. siRNA). The inhibitor may also be an antibody such as a monoclonal antibody.

Preferably, an antibody inhibitor is a neutralising antibody inhibitor.

The term "small molecule" denotes a generally low molecular weight compound and includes organic and inorganic compounds. In general, a small molecule has a well-defined chemical formula with a single molecular weight. Preferably, a small molecule has a molecular weight of less than 3000 daltons. More preferably, a small molecule has a molecular weight of less than 2000 daltons. In some embodiments of this invention, the small molecule has a molecular weight of less than 1000 daltons. Some non-limiting examples of small molecules include lipids such as fatty acids; saccharides (mono, di or poly); xenobiotics; organometallic compounds and natural products.

The inhibitor of IRAP may exhibit a K value of less than 1 mM, preferably less than 100 μM, more preferably less than 10 μM, as determined by an assay as described herein, for example of aminopeptidase activity or substrate degradation. Typically, the assay of amino peptidase activity comprises hydrolysis of the synthetic substrate L-Leucine 7-amido-4-methyl coumarin hydrochloride (Leu-MCA) monitored by release of the fluorogenic product MCA. The assay of substrate degradation may be degradation of the peptide substrates CYFQNCPRG (SEQ ID NO: 1), CYIQNCPLG—NH2 (SEQ ID NO: 6) or YGGFL (SEQ ID NO: 2).

Inhibitors of IRAP are known in the art. For example, IRAP inhibitors described in Albiston et al. (2008) The FASEB Journal 22:4209-4217; Albiston et al. (2011), British Journal of Pharmacology, 164:37-47, Albiston, et al. J. Biol. Chem. 276, 48263-48266; U.S. Pat. No. 6,066,672; Albiston, et al. Pharmacol. Ther. 116, 417-427; Axen, et al. (2006) J. Pept. Sci. 12, 705-713; Albiston et al. (2010) Molecular Pharmacology, 78(4): 600-607; Mountford, et al. (2014) J Med Chem 57(4): 1368-1377; Andersson et al. J Med Chem (2010) 53, 8059, Andersson et al. (2011) J Med Chem 54(11):3779-3792; WO2009065169; WO2010001079; WO 2000/012544; US 2004/0086510; WO 2003/011304; and WO2006026832, and may be useful in the present invention.

An inhibitor of IRAP as described herein may have a structure according to Formula (I):

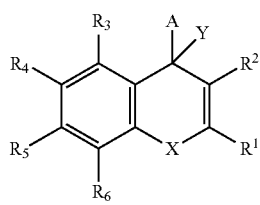

(I)

wherein

A is aryl, heteroaryl carbocyclyl or heterocyclyl, each of which may be optionally substituted, when $R^1$ is $NHCOR_8$;

or quinolinyl, isoquinolinyl, cinnolinyl, quinazolinyl, quinoxalinyl, 1,8-naphthyridyl, phthalazinyl or pteridinyl, each of which may be optionally substituted, when $R^1$ is $NR_7R_8$, $NHCOR_8$, $N(COR_8)_2$, $N(COR_7)(COR_8)$, $N\!\!=\!\!CHOR_8$ or $N\!\!=\!\!CHR_8$;

X is O, NR' or S, wherein R' is hydrogen, optionally substituted alkyl, optionally substituted alkenyl, optionally substituted alkynyl, optionally substituted aryl, optionally substituted acyl, optionally substituted heteroaryl, optionally substituted carbocyclyl or optionally substituted heterocyclyl;

$R_7$ and $R_8$ are independently selected from hydrogen, optionally substituted alkyl, optionally substituted aryl, or $R_7$ and $R_8$, together with the nitrogen atom to which they are attached form a 3-8-membered ring which may be optionally substituted;

$R^2$ is CN, $CO_2R^9$, $C(O)O(O)R^9$, $C(O)R^9$ or $C(O)NR^9R^{10}$ wherein $R^9$ and $R^{10}$ are independently selected from alkyl, alkenyl, alkynyl, aryl, heteroaryl, carbocyclyl, heterocyclyl, each of which may be optionally substituted, and hydrogen; or $R^9$ and $R^{10}$ together with the nitrogen atom to which they are attached, form a 3-8-membered ring which may be optionally substituted;

$R_3$-$R_6$ are independently selected from hydrogen, halo, nitro, cyano alkyl, alkenyl, alkynyl, aryl, heteroaryl, heterocyclyl, carbocyclyl, hydroxy, alkoxy, alkenyloxy, alkynyloxy, alkynyloxy, aryloxy, heteroaryloxy, heterocyclyloxy, amino, acyl, acyloxy, carboxy, carboxyester, methylenedioxy, amido, thio, alkylthio, alkenylthio, alkynylthio, arylthio, heteroarylthio, heterocyclylthio, carbocyclylthio, acylthio and azido, each of which may be optionally substituted where appropriate, or any two adjacent $R^3$-$R^6$, together with the atoms to which they are attached, form a 3-8-membered ring which may be optionally substituted; and Y is hydrogen or $C_{1-10}$alkyl, or a pharmaceutically acceptable salt or solvate thereof.

In one preferred embodiment, A is optionally substituted heteroaryl when $R^1$ is $NHCOR_8$. More preferably, A is pyridinyl.

In another preferred embodiment, X is O.
In yet another preferred embodiment, $R^2$ is $CO_2R^9$.
In one preferred embodiment, $R_5$ is hydroxyl.
In one embodiment, the inhibitor has the structure:

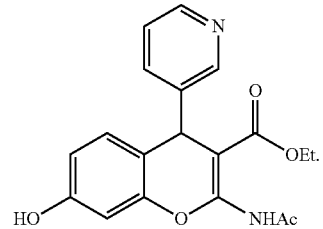 [SMILES: CCOC(=O)C1=C(NC(C)=O)Oc2cc(O)ccc2C1c1cccnc1]

An inhibitor of IRAP as described herein may have a structure according to Formula (II):

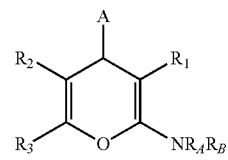

(II)

wherein

A is selected from alkyl, alkenyl, alkynyl, aryl, arylalkyl, heteroaryl, heteroarylalkyl, carbocyclyl, carbocyclylalkyl, each of which may be optionally substituted;

$R_A$ and $R_B$ are independently selected from hydrogen, alkyl and acyl;

$R_1$ is selected from CN or $CO_2R_C$;

$R_2$ is selected from $CO_2R_C$ and acyl;

$R_3$ is selected from alkyl, alkenyl, alkynyl, aryl, arylalkyl, heteroaryl, heteroarylalkyl, carbocyclyl, carbocyclylalkyl, each of which may be optionally substituted; or $R_2$ and $R_3$ together form a 5-6-membered saturated ketocarbocyclic ring:

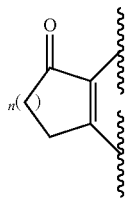

wherein n is 1 or 2;

and which ring may be optionally substituted one or more times by $C_{1-6}$alkyl; or $R_2$ and $R_3$ together form a 5-membered lactone ring (a) or a 6-membered lactone ring (b)

(a)
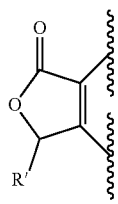

(b)
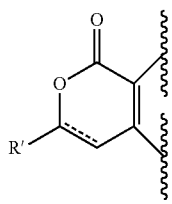

wherein ═ is an optional double bond and R' is alkyl.

$R_C$ is selected from alkyl, alkenyl, alkynyl, aryl, arylalkyl, heteroaryl, heteroarylalkyl, carbocyclyl, carbocyclylalkyl, each of which may be optionally substituted;

or a pharmaceutically acceptable salt, solvate or prodrug thereof.

In a preferred embodiment, A is optionally substituted aryl. More preferably, A is aryl substituted with —CH, or a salt, ester or prodrug thereof. For example, A may be aryl substituted with —$CO_2^-NH_4^+$.

In another preferred embodiment, $R_1$ is CN.

In yet another preferred embodiment, $R_2$ is acyl.

In one embodiment, the inhibitor has the structure:

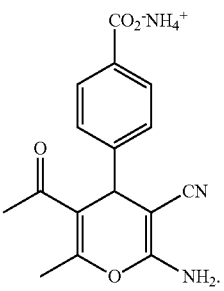

In other embodiments, the inhibitor has a structure selected from the group consisting of:

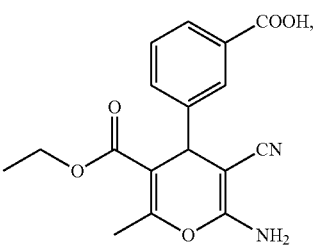

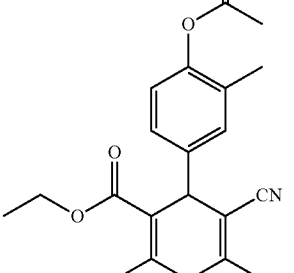

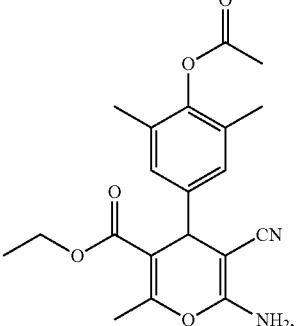

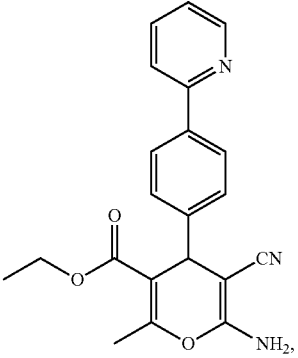

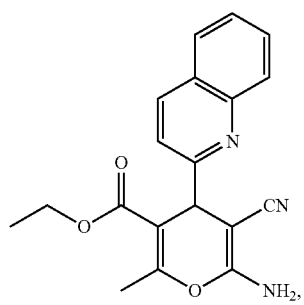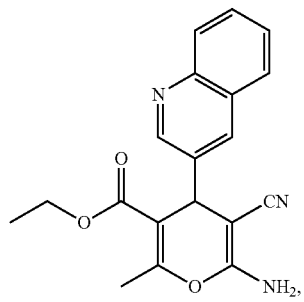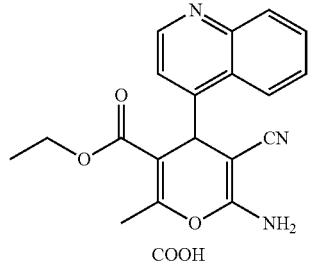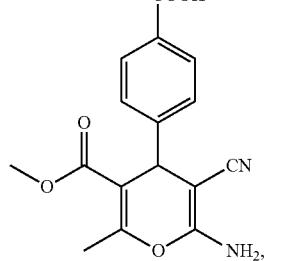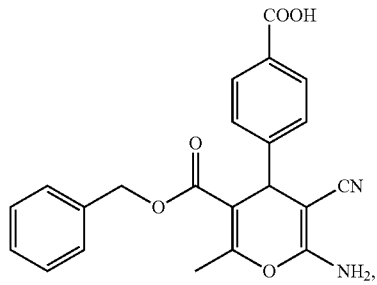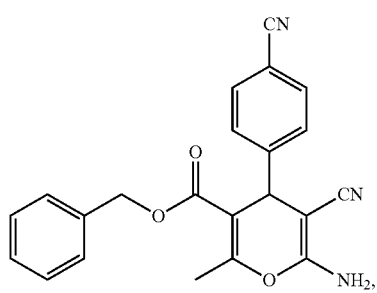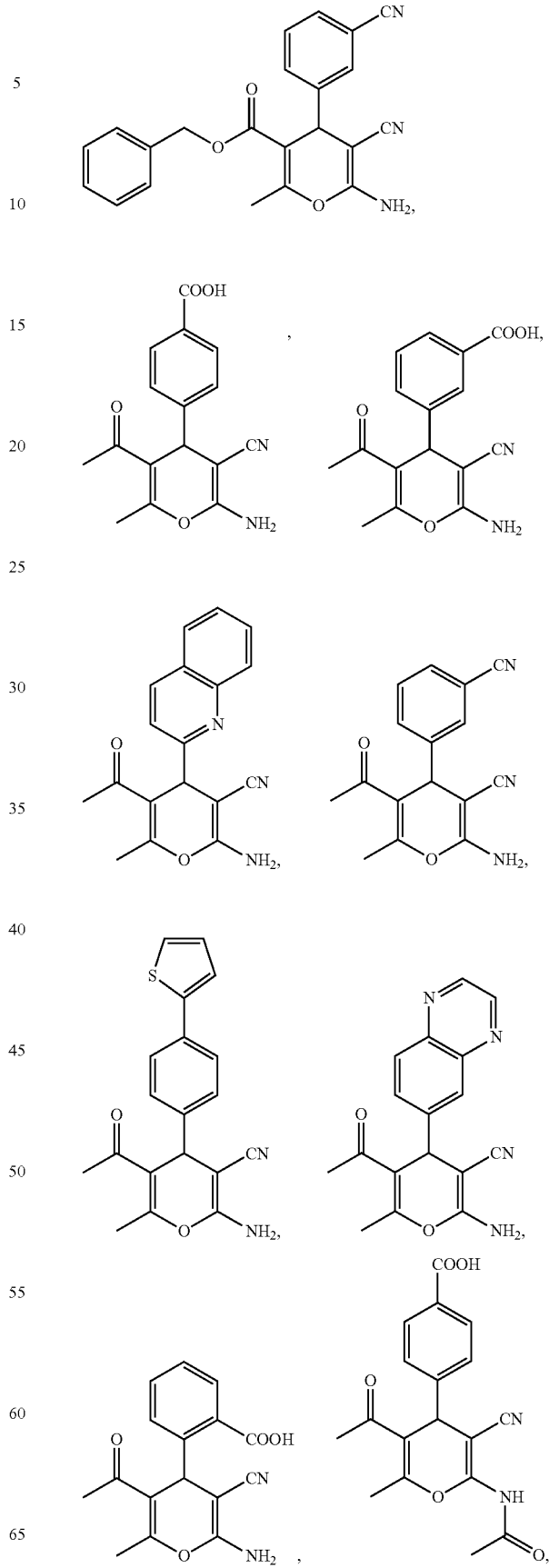

-continued

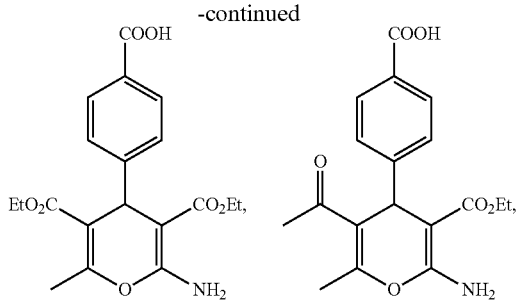

and/or a pharmaceutically acceptable salt, solvate or prodrug thereof.

In another embodiment of the present invention, the inhibitor has a structure according to Formula (III):

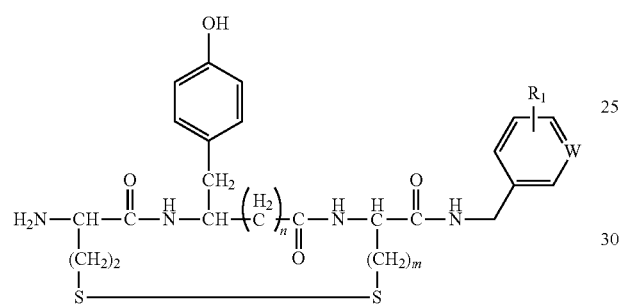

(III)

wherein
R₁ is H or CH₂OOH; and
n is 0 or 1; and
m is 1 or 2; and
W is CH or N;
or a pharmaceutically acceptable salt, solvate or prodrug thereof.

In one embodiment, the inhibitor has the structure:

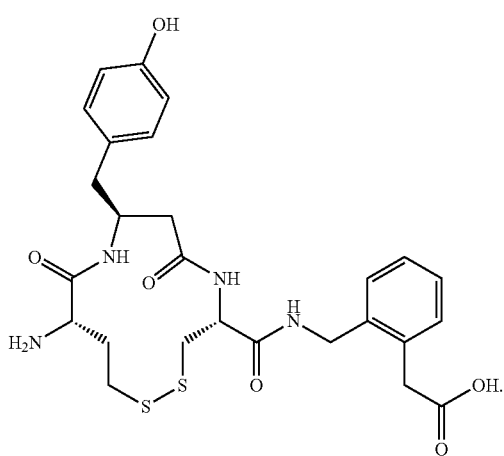 [SMILES: N[C@H]1CCSSC[C@@H](C(=O)NCc2ccccc2CC(=O)O)NC(=O)C[C@H](Cc2ccc(O)cc2)NC1=O]

In another embodiment of the present invention, the inhibitor has a structure according to any one of the following sequences:

Val-Tyr-Ile-His-Pro-Phe, (SEQ ID NO: 3)

c[Cys-Tyr-Cys]-His-Pro-Phe, (SEQ ID NO: 4)
and c[Hcy-Tyr-Hcy]-His-Pro-Phe. (SEQ ID NO: 5)

In yet another embodiment of the present invention, the inhibitor has a structure according to the compound

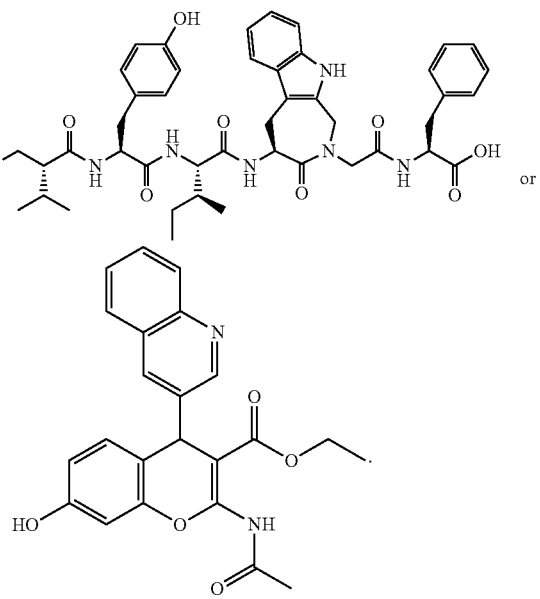

or

As used herein, the term "alkyl" or "alk", used either alone or in compound words denotes straight chain, or branched alkyl, preferably $C_{1-20}$ alkyl, e.g. $C_{1-10}$ or $C_{1-6}$. Examples of straight chain and branched alkyl include methyl, ethyl, n-propyl, isopropyl, n-butyl, sec-butyl, t-butyl, n-pentyl, 1,2-dimethylpropyl, 1,1-dimethyl-propyl, hexyl, 4-methylpentyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2,-trimethylpropyl, 1,1,2-trimethylpropyl, heptyl, 5-methylhexyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethyl-pentyl, 1,2,3-trimethylbutyl, 1,1,2-trimethylbutyl, 1,1,3-trimethylbutyl, octyl, 6-methylheptyl, 1-methylheptyl, 1,1,3,3-tetramethylbutyl, nonyl, 1-, 2-, 3-, 4-, 5-, 6- or 7-methyl-octyl, 1-, 2-, 3-, 4- or 5-ethylheptyl, 1-, 2- or 3-propylhexyl, decyl, 1-, 2-, 3-, 4-, 5-, 6-, 7- and 8-methylnonyl, 1-, 2-, 3-, 4-, 5- or 6-ethyloctyl, 1-, 2-, 3- or 4-propylheptyl, undecyl, 1-, 2-, 3-, 4-, 5-, 6-, 7-, 8- or 9-methyldecyl, 1-, 2-, 3-, 4-, 5-, 6- or 7-ethylnonyl, 1-, 2-, 3-, 4- or 5-propylocytl, 1-, 2- or 3-butylheptyl, 1-pentylhexyl, dodecyl, 1-, 2-, 3-, 4-, 5-, 6-, 7-, 8-, 9- or 10-methylundecyl, 1-, 2-, 3-, 4-, 5-, 6-, 7- or 8-ethyldecyl, 1-, 2-, 3-, 4-, 5- or 6-propylnonyl, 1-, 2-, 3- or 4-butyloctyl, 1-2-pentylheptyl and the like. Where an alkyl group is referred to generally as "propyl", butyl" etc, it will be understood that this can refer to any of straight or branched isomers where appropriate. An alkyl group may be optionally substituted by one or more optional substituents as herein defined.

The term "alkenyl" as used herein denotes groups formed from straight chain or branched hydrocarbon residues containing at least one carbon to carbon double bond including ethylenically mono-, di- or poly-unsaturated alkyl groups as previously defined, preferably $C_{2-20}$ alkenyl (e.g. $C_{2-10}$ or $C_{2-6}$). Examples of alkenyl include vinyl, allyl, 1-methylvinyl, butenyl, iso-butenyl, 3-methyl-2-butenyl, 1-pentenyl, 1-hexenyl, 3-hexenyl, 1-heptenyl, 3-heptenyl, 1-octenyl, 1-nonenyl, 2-nonenyl, 3-nonenyl, 1-decenyl, 3-decenyl, 1,3-butadienyl, 1-4, pentadienyl, 1,3-hexadienyl and 1,4-hexadienyl. An alkenyl group may be optionally substituted by one or more optional substituents as herein defined.

As used herein the term "alkynyl" denotes groups formed from straight chain or branched hydrocarbon residues containing at least one carbon-carbon triple bond including ethynically mono-, di- or poly-unsaturated alkyl groups as previously defined. Unless the number of carbon atoms is specified the term preferably refers to $C_{2-20}$ alkynyl (e.g. $C_{2-10}$ or $C_{2-6}$). Examples include ethynyl, 1-propynyl, 2-propynyl, and butynyl isomers, and pentynyl isomers. An alkynyl group may be optionally substituted by one or more optional substituents as herein defined.

Terms written as "[group]oxy" refer to a particular group when linked by oxygen, for example, the terms "alkoxy", "alkenoxy", "alkynoxy", "aryloxy" and "acyloxy" respectively denote alkyl, alkenyl, alkynyl, aryl and acyl groups as hereinbefore defined when linked by an oxygen atom. Terms written as "[group]thio" refer to a particular group when linked by sulfur, for example, the terms "alkylthio", "alkenylthio", alkynylthio" and "arylthio" respectively denote alkyl, alkenyl, alkynyl, aryl groups as hereinbefore defined when linked by a sulfur atom. Similarly, a term written as "[groupA]groupB" is intended to refer to a groupA when linked by a divalent form of groupB, for example, "hydroxyalkyl" is a hydroxy group when linked by an alkylene group.

The term "halogen" ("halo") denotes fluorine, chlorine, bromine or iodine (fluoro, chloro, bromo or iodo).

The term "aryl" (or "carboaryl)", or the abbreviated form "ar" used in compound words such as "aralkyl", denotes any of mono-, bi- or polcyclic, (including conjugated and fused) hydrocarbon ring systems containing an aromatic residue. Examples of aryl include phenyl, biphenyl, terphenyl, quaterphenyl, naphthyl, tetrahydronaphthyl (tetralinyl), anthracenyl, dihydroanthracenyl, benzanthracenyl, dibenzanthracenyl, phenanthrenyl, fluorenyl, pyrenyl, idenyl, isoindenyl, indanyl, azulenyl and chrysenyl. Particular examples of aryl include phenyl and naphthyl. An aryl group may be optionally substituted by one or more optional substituents as herein defined.

The term "carbocyclyl" includes any of non-aromatic monocyclic, bicyclic and polycyclic, (including fused, bridged or conjugated) hydrocarbon residues, e.g. $C_{3-20}$ (such as $C_{3-10}$, $C_{3-8}$ or $C_{5-6}$). The rings may be saturated, for example cycloalkyl, or may possess one or more double bonds (cycloalkenyl) and/or one or more triple bonds (cycloalkynyl). Examples of particular carbocyclyl are monocyclic 5-6-membered or bicyclic 9-10 membered ring systems. Suitable examples include cyclopropyl, cyclobutyl, cyclopentyl, cyclohexyl, cycloheptyl, cyclooctyl, cyclononyl, cyclodecyl, cyclopentenyl, cyclohexenyl, cyclooctenyl, cyclopentadienyl, cyclohexadienyl, cyclooctatetraenyl and decalinyl. A carbocyclyl group may be optionally substituted by one or more optional substituents as herein defined. In particular, a monocarbocyclyl group may be substituted by a bridging group to form a bicyclic bridged group.

The term "carbocyclyl" includes any of non-aromatic monocyclic, bicyclic and polycyclic, (including fused, bridged or conjugated) hydrocarbon residues, e.g. $C_{3-20}$ (such as $C_{3-10}$, $C_{3-8}$ or $C_{5-6}$). The rings may be saturated, for example cycloalkyl, or may possess one or more double bonds (cycloalkenyl) and/or one or more triple bonds (cycloalkynyl). Examples of carbocyclyl include monocyclic 5-6-membered or bicyclic 9-membered ring systems. Suitable examples include cyclopropyl, cyclobutyl, cyclopentyl, cyclohexyl, cycloheptyl, cyclooctyl, cyclononyl, cyclodecyl, cyclopentenyl, cyclohexenyl, cyclooctenyl, cyclopentadienyl, cyclohexadienyl, cyclooctatetraenyl and decalinyl. A carbocyclyl group may be optionally substituted by one or more optional substituents as herein defined. A monocarbocyclyl group may be substituted by a bridging group to form a bicyclic bridged group.

The term "heterocyclyl" when used alone or in compound words includes any of monocyclic, bicyclic or polycyclic, (including fuse, bridged or conjugated) hydrocarbon residues, such as $C_{3-20}$ (e.g. $C_{3-10}$ or $C_{3-8}$) wherein one or more carbon atoms are independently replaced by a heteroatom so as to provide a group containing a non-aromatic heteroatom containing ring. Suitable heteroatoms include, O, N, S, P and Se, particularly O, N and S. Where two or more carbon atoms are replaced, this may be by two or more of the same heteroatom or by different heteroatoms. The heterocyclyl group may be saturated or partially unsaturated, e.g. possess one or more double bonds. Particularly preferred heterocyclyl are monocyclic 5-6- and bicyclic 9-10-membered heterocyclyl. Examples of heterocyclyl groups may include azridinyl, oxiranyl, thiiranyl, azetidinyl, oxetanyl, thietanyl, 2H-pyrrolyl, pyrrolidinyl, 1-, 2- and 3-pyrrolinyl, piperidyl, piperazinyl, morpholinyl, indolinyl, imidazolidinyl, imidazolinyl, pyrazolidinyl, thiomorpholinyl, dioxanyl, tetrahydrofuranyl, tetrahydropyranyl, tetrahydropyrrolyl, tetrahydrothiophenyl (tetramethylene sulfide), pyrazolinyl, dioxalanyl, thiazolidinyl, isoxazolidinyl, dihydropyranyl, oxazinyl, thiazinyl, thiomorpholinyl, oxathianyl, dithianyl, trioxanyl, thiadiazinyl, dithiazinyl, trithianyl, azepinyl, oxepinyl, thiepinyl, indenyl, indanyl, 3H-indolyl, isoindolinyl, 4H-quinolazinyl, chromenyl, chromanyl, isochromanyl, benzoxazinyl (2H-1,3, 2H-1,4-, 1H-2,3-, 4H-3,1-4H-1,4) pyranyl and dihydropyranyl. A heterocyclyl group may be optionally substituted by one or more optional substituents as defined herein.

The term "heteroaryl" includes any of monocyclic, bicyclic, polycyclic, fused, bridged or conjugated hydrocarbon residues, wherein one or more carbon atoms are replaced by a heteroatom so as to provide a residue having at least one aromatic heteroatom-containing ring. Exemplary heteroaryl have 3-20 ring atoms, e.g. 3-10. Particularly preferred heteroaryl are 5-6 monocyclic and 9-10 membered bicyclic ring systems. Suitable heteroatoms include, O, N, S, P and Se, particularly O, N and S. Where two or more carbon atoms are replaced, this may be by two or more of the same heteroatom or by different heteroatoms. Suitable examples of heteroaryl groups may include pyridyl, pyrrolyl, thienyl, imidazolyl, furanyl, benzothienyl, isobenzothienyl, benzofuranyl, isobenzofuranyl, indolyl, isoindolyl, pyrazolyl, pyrazinyl, pyrimidinyl, pyridazinyl, indolizinyl, quinolyl, isoquinolyl, phthalazinyl, 1,5-naphthyridinyl, quinozalinyl, quinazolinyl, quinolinyl, oxazolyl, thiazolyl, isothiazolyl, isoxazolyl, triazolyl, oxadialzolyl, oxatriazolyl, triazinyl, tetrazolyl and furazanyl. A heteroaryl group may be optionally substituted by one or more optional substituents as defined herein.

The term "acyl" either alone or in compound words denotes a group containing the moiety C=O. In some embodiments acyl does not include a carboxylic acid, ester or amide. Acyl includes C(O)—Z, wherein Z is hydrogen or an alkyl, aryl, heteroaryl, carbocyclyl, heterocyclyl, arylalkyl, heteroarylalkyl, carbocyclylalkyl, or heterocyclylalkyl residue. Examples of acyl include formyl, straight chain or branched alkanoyl (e.g. $C_{1-20}$) such as, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl and icosanoyl; cycloalkylcarbonyl such as cyclopropylcarbonyl cyclobutylcarbonyl, cyclopentylcarbonyl and cyclohexylcarbonyl; aroyl such as benzoyl, toluoyl and naphthoyl; aralkanoyl such as phenylalkanoyl (e.g. phenylacetyl, phenylpropanoyl, phenylbutanoyl, phenylisobutylyl, phenylpentanoyl and phenylhexanoyl) and naphthylalkanoyl (e.g. naphthylacetyl, naphthylpropanoyl and naphthylbutanoyl]; aralkenoyl such as phenylalkenoyl (e.g. phenylpropenoyl, phenylbutenoyl, phenylmethacryloyl, phenylpentenoyl and phenylhexenoyl and naphthylalkenoyl (e.g. naphthylpropenoyl, naphthylbutenoyl and naphthylpentenoyl); aryloxyalkanoyl such as phenoxyacetyl and phenoxypropionyl; arylthiocarbamoyl such as phenylthiocarbamoyl; arylglyoxyloyl such as phenylglyoxyloyl and naphthylglyoxyloyl; arylsulfonyl such as phenylsulfonyl and napthylsulfonyl; heterocycliccarbonyl; heterocyclicalkanoyl such as thienylacetyl, thienylpropanoyl, thienylbutanoyl, thienylpentanoyl, thienylhexanoyl, thiazolylacetyl, thiadiazolylacetyl and tetrazolylacetyl; heterocyclicalkenoyl such as heterocyclicpropenoyl, heterocyclicbutenoyl, heterocyclicpentenoyl and heterocyclichexenoyl; and heterocyclicglyoxyloyl such as thiazolyglyoxyloyl and thienylglyoxyloyl. The R and Z residues may be optionally substituted as described herein.

In this specification "optionally substituted" is taken to mean that a group may be unsubstituted or further substituted or fused (so as to form a condensed bi- or polycyclic group) with one, two, three or more of organic and inorganic groups, including those selected from: alkyl, alkenyl, alkynyl, carbocyclyl, aryl, heterocyclyl, heteroaryl, acyl, aralkyl, alkylaryl, alkylheterocyclyl, alkylheteroaryl, alkylcarbocyclyl, halo, haloalkyl, haloalkenyl, haloalkynyl, haloaryl, halocarbocyclyl, haloheterocyclyl, haloheteroaryl, haloacyl, haloaryalkyl, hydroxy, hydroxyalkyl, hydroxyalkenyl, hydroxyalkynyl, hydroxycarbocyclyl, hydroxyaryl, hydroxyheterocyclyl, hydroxyheteroaryl, hydroxyacyl, hydroxyaralkyl, alkoxyalkyl, alkoxyalkenyl, alkoxyalkynyl, alkoxycarbocyclyl, alkoxyaryl, alkoxyheterocyclyl, alkoxyheteroaryl, alkoxyacyl, alkoxyaralkyl, alkoxy, alkenyloxy, alkynyloxy, aryloxy, carbocyclyloxy, aralkyloxy, heteroaryloxy, heterocyclyloxy, acyloxy, haloalkoxy, haloalkenyloxy, haloalkynyloxy, haloaryloxy, halocarbocyclyloxy, haloaralkyloxy, haloheteroaryloxy, haloheterocyclyloxy, haloacyloxy, nitro, nitroalkyl, nitroalkenyl, nitroalkynyl, nitroaryl, nitroheterocyclyl, nitroheteroaryl, nitrocarbocyclyl, nitroacyl, nitroaralkyl, amino ($NH_2$), alkylamino, dialkylamino, alkenylamino, alkynylamino, arylamino, diarylamino, aralkylamino, diaralkylamino, acylamino, diacylamino, heterocyclamino, heteroarylamino, carboxy, carboxyester, amido, alkylsulphonyloxy, arylsulphenyloxy, alkylsulphenyl, arylsulphenyl, thio, alkylthio, alkenylthio, alkynylthio, arylthio, aralkylthio, carbocyclylthio, heterocyclylthio, heteroarylthio, acylthio, sulfoxide, sulfonyl, sulfonamido, aminoalkyl, aminoalkenyl, aminoalkynyl, aminocarbocyclyl, aminoaryl, aminoheterocyclyl, aminoheteroaryl, aminoacyl, aminoaralkyl, thioalkyl, thioalkenyl, thioalkynyl, thiocarbocyclyl, thioaryl, thioheterocyclyl, thioheteroaryl, thioacyl, thioaralkyl, carboxyalkyl, carboxyalkenyl, carboxyalkynyl, carboxycarbocyclyl, carboxyaryl, carboxyheterocyclyl, carboxyheteroaryl, carboxyacyl, carboxyaralkyl, carboxyesteralkyl, carboxyesteralkenyl, carboxyesteralkynyl, carboxyestercarbocyclyl, carboxyesteraryl, carboxyesterheterocyclyl, carboxyesterheteroaryl, carboxyesteracyl, carboxyesteraralkyl, amidoalkyl, amidoalkenyl, amidoalkynyl, amidocarbocyclyl, amidoaryl, amidoheterocyclyl, amidoheteroaryl, amidoacyl, amidoaralkyl, formylalkyl, formylalkenyl, formylalkynyl, formylcarbocyclyl, formylaryl, formylheterocyclyl, formylheteroaryl, formylacyl, formylaralkyl, acylalkyl, acylalkenyl, acylalkynyl, acylcarbocyclyl, acylaryl, acylheterocyclyl, acylheteroaryl, acylacyl, acylaralkyl, sulfoxidealkyl, sulfoxidealkenyl, sulfoxidealkynyl, sulfoxidecarbocyclyl, sulfoxidearyl, sulfoxideheterocyclyl, sulfoxideheteroaryl, sulfoxideacyl, sulfoxidearalkyl, sulfonylalkyl, sulfonylalkenyl, sulfonylalkynyl, sulfonylcarbocyclyl, sulfonylaryl, sulfonylheterocyclyl, sulfonylheteroaryl, sulfonylacyl, sulfonylaralkyl, sulfonamidoalkyl, sulfonamidoalkenyl, sulfonamidoalkynyl, sulfonamidocarbocyclyl, sulfonamidoaryl, sulfonamidoheterocyclyl, sulfonamidoheteroaryl, sulfonamidoacyl, sulfonamidoaralkyl, nitroalkyl, nitroalkenyl, nitroalkynyl, nitrocarbocyclyl, nitroaryl, nitroheterocyclyl, nitroheteroaryl, nitroacyl, nitroaralkyl, cyano, sulfate, sulfonate, phosphonate and phosphate groups. Optional substitution may also be taken to refer to where a $CH_2$ group in a chain or ring is replaced by a carbonyl group (C=O) or a thiocarbonyl group (C=S), where 2 adjacent or non-adjacent carbon atoms (e.g. 1,2- or 1,3) are substituted by one end each of a —O—$(CH_2)_s$—O— or —NRX—$(CH_2)_s$—NRX— group, wherein s is 1 or 2 and each $R^x$ is independently H or $C_{1-6}$alkyl, and where 2 adjacent or non-adjacent atoms, independently selected from C and N, are substituted by one end each of a $C_{1-5}$alkylene or $C_{2-5}$alkenylene group (so as to form a bridged group).

Exemplary optional substituents include those selected from: alkyl, (e.g. $C_{1-6}$alkyl such as methyl, ethyl, propyl, butyl), cycloalkyl (e.g. $C_{3-6}$cycloalkyl, such as cyclopropyl, cyclobutyl, cyclopentyl or cyclohexyl), hydroxyalkyl (e.g. hydroxy$C_{1-6}$alkyl, such as hydroxymethyl, hydroxyethyl, hydroxypropyl), alkoxyalkyl (e.g. $C_{1-6}$alkoxy$C_{1-6}$alkyl, such as methoxymethyl, methoxyethyl, methoxypropyl, ethoxymethyl, ethoxyethyl, ethoxypropyl), alkoxy (e.g. $C_{1-6}$alkoxy, such as methoxy, ethoxy, propoxy, butoxy), alkoxyalkoxy (e.g. $C_{1-6}$alkoxy$C_{1-6}$alkoxy, such as methoxymethoxy, methoxyethoxy, methoxypropoxy, ethoxymethoxy, ethoxyethoxy, ethoxypropoxy, propoxymethoxy, propoxyethoxy, propoxypropoxy) cycloalkoxy (e.g. cyclopropoxy, cyclobutoxy, cyclopentoxyl, cyclohexyloxy), halo, haloalkyl(e.g. halo$C_{1-6}$alkyl, such as chloromethyl, difluoromethyl, trifluoromethyl, trichloromethyl, tribromomethyl), haloalkoxy (e.g. halo$C_{1-6}$alkoxy), hydroxy, thio (—SH), sulfonyl, sulfonamide, phenyl (which itself may be further substituted e.g., by one or more $C_{1-6}$alkyl, halo, hydroxy, hydroxy$C_{1-6}$alkyl, $C_{1-6}$alkoxy, $C_{1-6}$alkoxy$C_{1-6}$alkyl, $C_{1-6}$alkoxy$C_{1-6}$alkoxy, halo$C_{1-6}$alkyl, halo$C_{1-6}$alkoxy, cyano, nitro, OC(O)$C_{1-6}$alkyl, $NH_2$, NHC$_{1-6}$alkyl, NHC(O)$C_{1-6}$alkyl and NC$_{1-6}$alkylC$_{1-6}$alkyl), benzyl (wherein benzyl itself may be further substituted e.g., by one or more of $C_{1-6}$alkyl, halo, hydroxy, hydroxy$C_{1-6}$alkyl, $C_{1-6}$alkoxy, $C_{1-6}$alkoxy$C_{1-6}$alkyl, $C_{1-6}$alkoxy$C_{1-6}$alkoxy, halo$C_{1-6}$alkyl, halo$C_{1-6}$alkoxy, cyano, nitro, OC(O)$C_{1-6}$alkyl, $NH_2$, NHC$_{1-6}$alkyl, NHC(O)$C_{1-6}$alkyl and NC$_{1-6}$alkylC$_{1-6}$alkyl), phenoxy (wherein phenyl itself may be further substituted e.g., by one or more of $C_{1-6}$alkyl, halo, hydroxy, hydroxy$C_{1-6}$alkyl, $C_{1-6}$alkoxy, $C_{1-6}$alkoxy$C_{1-6}$alkyl, $C_{1-6}$alkoxy$C_{1-6}$alkoxy, halo$C_{1-6}$alkyl, halo$C_{1-6}$alkoxy, cyano, nitro, OC(O)$C_{1-6}$alkyl, $NH_2$, NH$C_{1-6}$ alkyl, NHC(O)$C_{1-6}$alkyl and N$C_{1-6}$alkyl$C_{1-6}$alkyl), benzyloxy (wherein benzyl itself may be further substituted e.g., by one or more of $C_{1-6}$alkyl, halo, hydroxy, hydroxy$C_{1-6}$ alkyl, $C_{1-6}$alkoxy, $C_{1-6}$alkoxy$C_{1-6}$alkyl, $C_{1-6}$alkoxy$C_{1-6}$alkoxy, halo$_{1-6}$alkyl, halo$C_{1-6}$alkoxy, cyano, nitro, OC(O)$C_{1-6}$alkyl, $NH_2$, NHC$_{1-6}$alkyl, NHC(O)$C_{1-6}$alkyl and N$C_{1-6}$alkyl$C_{1-6}$alkyl), $NH_2$, alkylamino (e.g. —NH$C_{1-6}$alkyl, such as methylamino, ethylamino, propylamino etc), dialkylamino (e.g. —NH($C_{1-6}$alkyl)$_2$, such as dimethylamino, diethylamino, dipropylamino), acylamino (e.g. —NHC(O)$C_{1-6}$alkyl, such as —NHC(O)$CH_3$), phenylamino (i.e. —NHphenyl, wherein phenyl itself may be further substituted e.g., by one or more of $C_{1-6}$alkyl, halo, hydroxy, hydroxy$C_{1-6}$alkyl, hydroxy$C_{1-6}$alkoxy $C_{1-6}$alkoxy, $C_{1-6}$alkoxy$C_{1-6}$alkyl, $C_{1-6}$alkoxy$C_{1-6}$alkoxy, halo$C_{1-6}$alkyl, halo$C_{1-6}$alkoxy, cyano, nitro, OC(O)$C_{1-6}$alkyl, $NH_2$, NHC$_{1-6}$ alkyl, NHC(O)$C_{1-6}$alkyl and N$C_{1-6}$alkyl$C_{1-6}$alkyl), nitro, cyano, formyl, —C(O)-alkyl (e.g. —C(O)$C_{1-6}$alkyl, such as acetyl), O—C(O)-alkyl (e.g. —OC(O)$C_{1-6}$alkyl, such as acetyloxy), benzoyl (wherein benzyl itself may be further substituted e.g., by one or more of $C_{1-6}$alkyl, halo, hydroxy, hydroxy$C_{1-6}$alkyl, $C_{1-6}$alkoxy, $C_{1-6}$alkoxy$C_{1-6}$alkyl, $C_{1-6}$alkoxy$C_{1-6}$alkoxy, halo$C_{1-6}$alkyl, halo$C_{1-6}$alkoxy, cyano, nitro, OC(O)$C_{1-6}$alkyl, $NH_2$, NH$C_{1-6}$alkyl, NHC(O)$C_{1-6}$alkyl and N$C_{1-6}$alkyl$C_{1-6}$alkyl), benzoyloxy (wherein benzyl itself may be further substituted e.g., by one or more of $C_{1-6}$alkyl, halo, hydroxy, hydroxy$C_{1-6}$alkyl, $C_{1-6}$alkoxy, $C_{1-6}$alkoxy$C_{1-6}$alkyl, $C_{1-6}$alkoxy$C_{1-6}$alkoxy, halo$C_{1-6}$alkyl, halo$C_{1-6}$alkoxy, cyano, nitro, OC(O)$C_{1-6}$alkyl, $NH_2$, NH$C_{1-6}$ alkyl, NHC(O)$C_{1-6}$alkyl and N$C_{1-6}$alkyl$C_{1-6}$alkyl), $CO_2H$, $CO_2$alkyl (e.g. $CO_2C_{1-6}$alkyl such as methyl ester, ethyl ester, propyl ester, butyl ester), $CO_2$phenyl (wherein phenyl itself may be further substituted e.g., by one or more of $C_{1-6}$alkyl, halo, hydroxy, hydroxy$C_{1-6}$alkyl, $C_{1-6}$alkoxy, $C_{1-6}$alkoxy$C_{1-6}$alkyl, $C_{1-6}$alkoxy$C_{1-6}$alkoxy, halo$C_{1-6}$alkyl, halo$C_{1-6}$alkoxy, cyano, nitro, OC(O)$C_{1-6}$alkyl, $NH_2$, NH$C_{1-6}$ alkyl, NHC(O)$C_{1-6}$alkyl and N$C_{1-6}$alkyl$C_{1-6}$alkyl), $CO_2$benzyl (wherein benzyl itself may be further substituted e.g., by one or more of $C_{1-6}$alkyl, halo, hydroxy, hydroxy$C_{1-6}$ alkyl, $C_{1-6}$alkoxy, $C_{1-6}$alkoxy$C_{1-6}$alkyl, $C_{1-6}$alkoxy$C_{1-6}$alkoxy, halo$C_{1-6}$alkyl, halo$C_{1-6}$alkoxy, cyano, nitro, OC(O)$C_{1-6}$alkyl, $NH_2$, NH$C_{1-6}$alkyl, NHC(O)$C_{1-6}$alkyl and N$C_{1-6}$alkyl$C_{1-6}$alkyl), $CONH_2$, C(O)NHphenyl (wherein phenyl itself may be further substituted e.g., by one or more of $C_{1-6}$alkyl, halo, hydroxy, hydroxy$C_{1-6}$alkyl, $C_{1-6}$alkoxy, $C_{1-6}$alkoxy$C_{1-6}$alkyl, $C_{1-6}$alkoxy$C_{1-6}$alkoxy, halo$C_{1-6}$alkyl, halo$C_{1-6}$alkoxy, cyano, nitro, OC(O)$C_{1-6}$alkyl, $NH_2$, NH$C_{1-6}$alkyl, NHC(O)$C_{1-6}$alkyl and N$C_{1-6}$alkyl$C_{1-6}$alkyl), C(O)NHbenzyl (wherein benzyl itself may be further substituted e.g., by one or more of $C_{1-6}$alkyl, halo, hydroxy, hydroxy$C_{1-6}$alkyl, $C_{1-6}$alkoxy, $C_{1-6}$alkoxy$C_{1-6}$alkyl, $C_{1-6}$alkoxy$C_{1-6}$alkoxy, halo$C_{1-6}$alkyl, halo$C_{1-6}$alkoxy, cyano, nitro, OC(O)$C_{1-6}$alkyl, $NH_2$, NH$C_{1-6}$alkyl, NHC(O)$C_{1-6}$alkyl and N$C_{1-6}$alkyl$C_{1-6}$alkyl), C(O)NHalkyl (e.g. C(O)NH$C_{1-6}$ alkyl such as methyl amide, ethyl amide, propyl amide, butyl amide) C(O)Ndialkyl (e.g. C(O)N($C_{1-6}$alkyl)$_2$) aminoalkyl (e.g., HN$C_{1-6}$alkyl-, $C_{1-6}$alkylHN-$C_{1-6}$ alkyl- and ($C_{1-6}$alkyl)$_2$N—$C_{1-6}$alkyl-), thioalkyl (e.g., HS$C_{1-6}$alkyl-), carboxyalkyl (e.g., $HO_2$CC$_{1-6}$alkyl-), carboxyesteralkyl (e.g., $C_{1-6}$alkylO$_2$CC$_{1-6}$alkyl-), amidoalkyl (e.g., $H_2$N(O)CC$_{1-6}$alkyl-, H($C_{1-6}$alkyl)N(O)CC$_{1-6}$alkyl-), formylalkyl (e.g., OHC$C_{1-6}$alkyl-), acylalkyl (e.g., $C_{1-6}$alkyl (O)CC$_{1-6}$alkyl-), nitroalkyl (e.g., $O_2$N$C_{1-6}$alkyl-), replacement of $CH_2$ with C=O, replacement of $CH_2$ with C=S, substitution of 2 adjacent or non-adjacent carbon atoms (e.g. 1,2 or 1,3) by one end each of a —O—$(CH_2)_s$—O— or —NR'—$(CH_2)_S$—NR'— group, wherein s is 1 or 2 and each R' is independently H or $C_{1-6}$alkyl, and substitution of 2 adjacent or non-adjacent atoms, independently selected from C and N, by a $C_{2-5}$alkylene or $C_{2-5}$alkenylene group.

The term "sulfoxide", either alone or in a compound word, refers to a group —S(O)R wherein R is selected from hydrogen, alkyl, alkenyl, alkynyl, aryl, heteroaryl, heterocyclyl, carbocyclyl, and aralkyl. Examples of R include hydrogen, $C_{1-20}$alkyl, phenyl and benzyl.

The term "sulfonyl", either alone or in a compound word, refers to a group $S(O)_2$—R, wherein R is selected from hydrogen, alkyl, alkenyl, alkynyl, aryl, heteroaryl, heterocyclyl, carbocyclyl, acyl, and aralkyl. Examples of R include hydrogen, $C_{1-20}$alkyl, phenyl and benzyl.

The term "sulfonamide", or "sulfonamyl" of "sulfonamido", either alone or in a compound word, refers to a group $S(O)_2$NRR wherein each R is independently selected from hydrogen, alkyl, alkenyl, alkynyl, aryl, heteroaryl, heterocyclyl, carbocyclyl, acyl, and aralkyl. Examples of R include hydrogen, $C_{1-20}$alkyl, phenyl and benzyl. In an embodiment at least one R is hydrogen. In another form, both R are hydrogen.

The term "sulfamate", either alone or in a compound word, refers to a group —OS(O)$_2$NRR wherein each R is independently selected from hydrogen, alkyl, aryl, heteroaryl, heterocyclyl, carbocyclyl, acyl, and aralkyl. Examples of R include hydrogen, $C_{1-20}$alkyl, phenyl and benzyl. In an embodiment at least one R is hydrogen. In another form, both R are hydrogen.

The term "sulfamide", either alone or in a compound word, refers to a group —NRS(O)$_2$NRR wherein each R is independently selected from hydrogen, alkyl, aryl, heteroaryl, heterocyclyl, carbocyclyl, acyl, and aralkyl. Examples of R include hydrogen, $C_{1-20}$alkyl, phenyl and benzyl. In an embodiment at least one R is hydrogen. In another form, both R are hydrogen.

A "sulfate" group refers to a group —OS(O)$_2$OR wherein each R is independently selected from hydrogen, alkyl, alkenyl, alkynyl, aryl, heteroaryl, heterocyclyl, carbocyclyl, acyl, and aralkyl. Examples of R include hydrogen, $C_{1-20}$alkyl, phenyl and benzyl.

The term "sulfonate" refers to a group $SO_3$R wherein each R is independently selected from hydrogen, alkyl, alkenyl, alkynyl, aryl, heteroaryl, heterocyclyl, carbocyclyl, acyl, and aralkyl. Examples of R include hydrogen, $C_{1-20}$alkyl, phenyl and benzyl.

The term "thio" is intended to include groups of the formula "—SR" wherein R can be hydrogen (thiol), alkyl, alkenyl, alkynyl, aryl, carbocyclyl, heteroaryl, heterocyclyl, aralkyl, and acyl. Examples of R include hydrogen, $C_{1-20}$alkyl, phenyl and benzyl.

The term, "amino" is used here in its broadest sense as understood in the art and includes groups of the formula —NR$_A$R$_B$ wherein R$_A$ and R$_B$ may be independently selected from hydrogen, hydroxy alkyl, alkoxyalkyl, aryl, heteroaryl, carbocyclyl, heterocyclyl, arylalkyl, heteroarylalkyl, carbocyclylalkyl, heterocyclylalkyl, acyl and amido, each of which may be optionally substituted as described herein. R$_A$ and R$_B$, together with the nitrogen to which they are attached, may also form a monocyclic, or fused polycyclic ring system e.g. a 3-10-membered ring, particularly, 5-6 and 9-10-membered systems. Examples of "amino" include —$NH_2$, —NHalkyl (e.g. —NH$C_{1-20}$alkyl), —NHalkoxyalkyl, —NHaryl (e.g. —NHphenyl), —NHaralkyl (e.g. —NHbenzyl), —NHacyl (e.g. —NHC(O)$C_{1-20}$alkyl, —NHC(O)phenyl), -NHamido, (e.g. NHC(O)NHC$_{1-6}$alkyl, NHC(O)NH phenyl), -Ndialkyl (wherein each alkyl, for example C$_{1-20}$, may be the same or different) and 5 or 6 membered rings, optionally containing one or more same or different heteroatoms (e.g. O, N and S). Reference to groups written as "[group]amino" is intended to reflect the nature of the R$_A$ and R$_B$ groups. For example, "alkylamino" refers to —NR$_A$R$_B$ where one of R$_A$ or R$_B$ is alkyl. "Dialkylamino" refers to —NR$_A$R$_B$ where R$_A$ and R$_B$ are each (independently) an alkyl group.

The term "amido" is used here in its broadest sense as understood in the art and includes groups having the formula C(O)NR$_A$R$_B$, wherein R$_A$ and R$_B$ are as defined as above. Examples of amido include C(O)NH$_2$, C(O)NHalkyl (e.g. C$_{1-20}$alkyl), C(O)NHaryl (e.g. C(O)NHphenyl), C(O)NHaralkyl (e.g. C(O)NHbenzyl), C(O)NHacyl (e.g. C(O)NHC(O)C$_{1-20}$alkyl, C(O)NHC(O)phenyl), C(O)Nalkylalkyl (wherein each alkyl, for example C$_{1-20}$, may be the same or different) and 5 or 6 membered rings, optionally containing one or more same or different heteroatoms (e.g. O, N and S).

The term "carboxy ester" is used here in its broadest sense as understood in the art and includes groups having the formula —CO$_2$R, wherein R may be selected from groups including alkyl, alkenyl, alkynyl, aryl, carbocyclyl, heteroaryl, heterocyclyl, arylalkyl, heteroarylalkyl, carbocyclylalkyl, heterocyclylalkyl, aralkenyl, heteroarylalkenyl, carbocyclylalkenyl, heterocyclylalkenyl, aralkynyl, heteroarylalkynyl, carbocyclylalkynyl, heterocyclylalkynyl, and acyl, each of which may be optionally substituted. Some examples of carboxy ester include —CO$_2$C$_{1-20}$alkyl, —CO$_2$aryl (e.g. —CO$_2$phenyl), —CO$_2$arC$_{1-20}$alkyl (e.g. —CO$_2$ benzyl).

The term "phosphonate" refers to a group —P(O)(OR$_2$) wherein R is independently selected from hydrogen, alkyl, aryl, heteroaryl, heterocyclyl, carbocyclyl, acyl, and aralkyl. Examples of R include hydrogen, C$_{1-20}$alkyl, phenyl and benzyl.

The term "phosphate" refers to a group —OP(O)(OR)$_2$ wherein R is independently selected from hydrogen, alkyl, aryl, heteroaryl, heterocyclyl, carbocyclyl, acyl, and aralkyl. Examples of R include hydrogen, C$_{1-20}$alkyl, phenyl and benzyl.

Carboxyclic isosteres are groups which can exhibit the same or similar properties as a carboxylic group. Some examples of carboxylic acid isosteres include: —SO$_3$H, —SO$_2$NHR, —PO$_2$R$_2$, —CN, —PO$_2$R$_2$, —OH, —OR, —SH, —SR, —NHCOR, —NR$_2$, —CONR$_2$, —CONH(O)R, —CONHNHSO$_2$R, —COHNSO$_2$R and —CONR—CN, where R is selected from H, alkyl (such as C$_{1-6}$ alkyl), phenyl and benzyl. Other carboxylic acid isosteres include carbocyclic and heterocyclic groups such as:

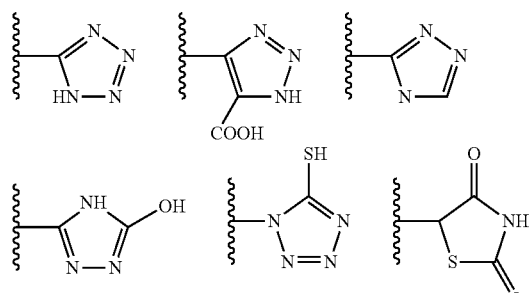

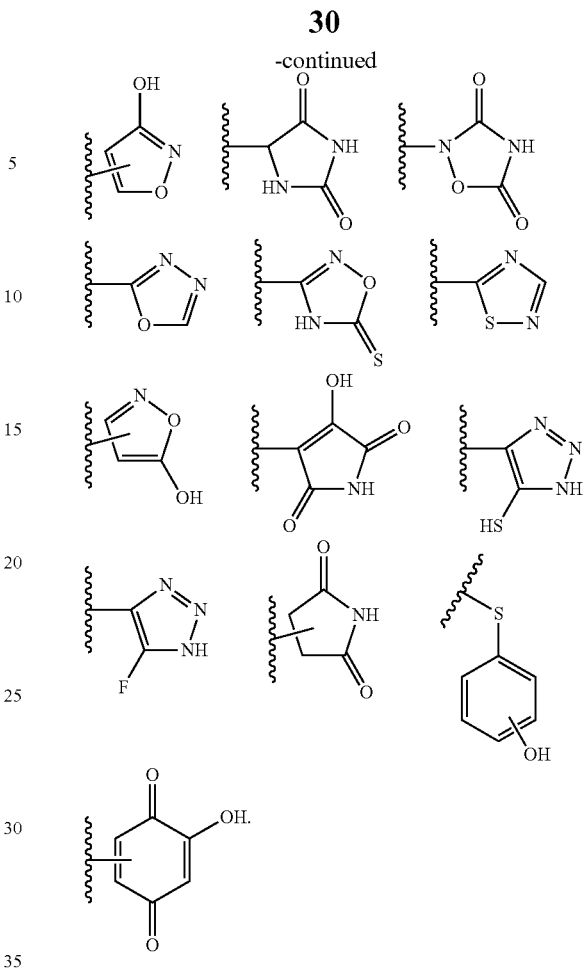

As used herein, reference to IRAP inhibitor or inhibitor of IRAP also includes a pharmaceutically acceptable salt, solvate, polymorph or prodrug thereof.

The term 'pharmaceutically-acceptable salts' refers to those salts which, within the scope of sound medical judgement, are suitable for use in contact with the tissues of humans and animals without undue toxicity, irritation, allergic response and the like, and are commensurate with a reasonable benefit/risk ratio. Pharmaceutically acceptable salts are well known in the art. S. M. Berge et al. describe pharmaceutically acceptable salts in detail in J. Pharmaceutical Sciences, 1977, 66:1-19. The salts include relatively non-toxic, inorganic and organic acid salts of any small molecule inhibitors, as appropriate.

Examples of such inorganic acids are hydrochloric, hydrobromic, hydroiodic, nitric, carbonic, sulfuric, and phosphoric acid. Appropriate organic acids may be selected from aliphatic, cycloaliphatic, aromatic, heterocyclic carboxylic and sulfonic classes of organic acids, examples of which are formic, acetic, propionic, succinic, glycolic, gluconic, lactic, malic, tartaric, citric, ascorbic, glucoronic, fumaric, maleic, pyruvic, alkyl sulfonic, arylsulfonic, aspartic, glutamic, benzoic, anthranilic, mesylic, salicylic, p-hydroxybenzoic, phenylacetic, mandelic, ambonic, pamoic, pantothenic, sulfanilic, cyclohexylaminosulfonic, stearic, algenic, β-hydroxybutyric, galactaric, and galacturonic acids. Suitable pharmaceutically acceptable base addition salts of the compounds of the present invention include metallic salts made from lithium, sodium, potassium, magnesium, calcium, aluminium, and zinc, and organic salts made from organic bases such as choline, diethanolamine, morpholine.

Alternatively, organic salts made from N,N'-dibenzylethylenediamine, chloroprocaine, choline, diethanolamine, ethylenediamine, meglumine (N methylglucamine), procaine, ammonium salts, quaternary salts such as tetramethylammonium salt, amino acid addition salts such as salts with glycine and arginine.

For example, alkali metal salts (K, Na) and alkaline earth metal salts (Ca, Mg) may be used if deemed appropriate for the structure, but again any pharmaceutically acceptable, non-toxic salt may be used where appropriate. The Na- and Ca-salts are preferred.

Pharmaceutically acceptable solvates, including hydrates, of such compounds and such salts are also intended to be included within the scope of this invention.

In the case of small molecule inhibitors that are solids, it will be understood by those skilled in the art that the compounds, agents and salts may exist in different crystalline or polymorphic forms, all of which are intended to be within the scope of the present invention and specified formulae.

The term 'polymorph' includes any crystalline form of compounds of any compound described herein, such as anhydrous forms, hydrous forms, solvate forms and mixed solvate forms.

An antibody inhibitor of IRAP can be produced via techniques known in the art to generate an antibody against IRAP and then those antibodies can be screened for IRAP inhibitory activity using assays as described herein. For example, monoclonal antibodies can be prepared as follows. Immunization of mice or other appropriate host animal by an IRAP of fragment thereof. Immunization with IRAP of fragment thereof and/or adjuvant may be by multi-point injection usually subcutaneous injection or intraperitoneal injection. IRAP of fragment thereof may be conjugated to a carrier, such as serum albumin, or soybean trypsin on inhibitor, an antigen to enhance immunogenicity in the host. The preferred animal system for generating hybridomas is the murine system. Immunization protocols and techniques for isolation of immunized splenocytes for fusion are well known in the art. Fusion cell partners (e.g., murine myeloma cell lines SP2/0, NS0, NS1, rat myeloma Y3, rabbit myeloma 240E 1, human K6H6), fusion and screening procedures are also well known in the art (Galfre et al., 1977; Gefter et al., 1977; Galfre et al., 1979; Dangl et al., 1982; Spieker-Polet et al., 1995).

The phrase 'therapeutically effective amount' generally refers to an amount of one or more inhibitors, or, if a small molecule inhibitor, a pharmaceutically acceptable salt, polymorph or prodrug thereof of the present invention that (i) treats the particular disease, condition, or disorder, (ii) attenuates, ameliorates, or eliminates one or more symptoms of the particular disease, condition, or disorder, or (iii) delays the onset of one or more symptoms of the particular disease, condition, or disorder described herein.

"Fibrosis", "Fibrotic disease" or "Fibro proliferative disease" means the formation of excess fibrous connective tissue in a reparative process upon injury. Scarring is a result of continuous fibrosis that obliterates the affected organs or tissues architecture. As a result of abnormal reparative processes, which do not clear the formed scar tissue, fibrosis progresses further. Fibrosis can be found in various tissues, including the heart, the lungs, the liver, the skin, blood vessels and the kidneys. Examples of fibrosis are described herein and include pulmonary fibrosis, liver cirrhosis, systemic sclerosis, progressive kidney disease and cardiac fibrosis associated with various cardiovascular diseases.

An individual may be identified as having fibrosis by determining if a subject has organ dysfunction, scarring, alteration of normal extracellular matrix balance, increase in collagen deposition, increased collagen volume fraction, differentiation of fibroblasts to myofibroblasts, reduction in the level of matrix metalloproteinases and increase in the level of tissue Inhibitors of matrix metalloproteinases, increased levels of either N-terminal or C-terminal propeptide of type I procollagen (PINP or PICP) and decreased levels of C-terminal telopeptide of Type I Collagen (CTP or CITP), increased collagen deposition and impaired cardiac function measured by various noninvasive imaging techniques, impaired renal function measured by increased proteinurea and albuminurea, decreased glomerular filtration rate, doubling of plasma creatinine levels.

Preferably the fibrotic disease is associated upregulation of IRAP expression and/or activity. IRAP expression or activity can be measured by any assay described herein.

Organ fibrosis related to tissue injury includes fibrosis associated with cardiovascular disease and fibrosis that has occurred following an organ transplant, such as a kidney or liver transplant.

According to a preferred embodiment of the invention, the pulmonary fibrosis is idiopathic pulmonary fibrosis, sarcoidosis, cystic fibrosis, familial pulmonary fibrosis, silicosis, asbestosis, coal worker's pneumoconiosis, carbon pneumoconiosis, hypersensitivity pneumonitides, pulmonary fibrosis caused by inhalation of inorganic dust, pulmonary fibrosis caused by an infectious agent, pulmonary fibrosis caused by inhalation of noxious gases, aerosols, chemical dusts, fumes or vapours, drug-induced interstitial lung disease, or pulmonary hypertension.

According to a preferred embodiment of the invention, the liver fibrosis is resulting from a chronic liver disease, hepatitis B virus infection, hepatitis C virus infection, hepatitis D virus infection, schistosomiasis, alcoholic liver disease or non-alcoholic steatohepatitis, non-alcoholic fatty liver disease, obesity, diabetes, protein malnutrition, coronary artery disease, auto-immune hepatitis, cystic fibrosis, alpha-1-antitrypsin deficiency, primary biliary cirrhosis, drug reaction and exposure to toxins.

According to a preferred embodiment of the invention, the skin fibrosis is scarring, hypertrophic scarring, keloid scarring, dermal fibrotic disorder, psoriasis or scleroderma. Said scarring may derived from a burn, a trauma, a surgical injury, a radiation or an ulcer. Said ulcer can be a diabetic foot ulcer, a venous leg ulcer or a pressure ulcer.

As used herein, "preventing" or "prevention" is intended to refer to at least the reduction of likelihood of the risk of (or susceptibility to) acquiring a disease or disorder (i.e., causing at least one of the clinical symptoms of the disease not to develop in a patient that may be exposed to or predisposed to the disease but does not yet experience or display symptoms of the disease). Biological and physiological parameters for identifying such patients are provided herein and are also well known by physicians. For example, prevention of age-induced cardiac fibrosis, or cardiac or renal fibrosis associated with hypertensive heart disease, hypertensive cardiomyopathy or heart failure, or nephropathy with or without associated diabetes, may be characterised by an absence of interstitial collagen deposition, or an absence of an increase in interstitial collagen deposition if collagen deposition is already detectable in a subject.

The terms "treatment" or "treating" of a subject includes the application or administration of a compound of the invention to a subject (or application or administration of a compound of the invention to a cell or tissue from a subject) with the purpose of delaying, slowing, stabilizing, curing, healing, alleviating, relieving, altering, remedying, less worsening, ameliorating, improving, or affecting the disease or condition, the symptom of the disease or condition, or the risk of (or susceptibility to) the disease or condition. The term "treating" refers to any indication of success in the treatment or amelioration of an injury, pathology or condition, including any objective or subjective parameter such as abatement; remission; lessening of the rate of worsening; lessening severity of the disease; stabilization, diminishing of symptoms or making the injury, pathology or condition more tolerable to the subject; slowing in the rate of degeneration or decline; making the final point of degeneration less debilitating; or improving a subject's physical or mental well-being.

The existence of, improvement in, treatment of or prevention of a fibrotic disease may be by any clinically or biochemically relevant method of the subject or a biopsy therefrom. For example, a parameter measured may be the presence of fibrosis, the content of collagen, fibronectin, or another extracellular matrix protein, the phosphatidic acid level or choline level, the proliferation rate of the cells or any extracellular matrix components in the cells or transdifferentiation of the cells to myofibroblasts. For example, inhibition of kidney fibrosis can be detected by preventing a further loss of kidney function as measured by albuminurea or proteinurea, increased serum creatinine, a reduction in active fibrosis as measured by reduced levels of collagen fragments in urine samples, and by a reduction in the presence of myofibroblasts on kidney biopsy tissue. Further, for example, in lung fibrosis, a positive response to therapy would be to prevent a further decline in lung function as measured by spirometry, body plethysmography, and lung diffusion capacity. In addition, blood levels of collagen fragments would also be reduced.

Reversing fibrosis as described herein includes inhibiting synthesis and/or enhancing degradation of collagen. A clinically or biochemically observable consequence of a reversal of fibrosis is a reduction in fibrotic tissue formed as a response to ageing or tissue injury. Reversing fibrosis also may include a clinically or biochemically observable reduction in any characteristic or symptom of fibrosis as described herein at a time after treatment has commenced compared to a time prior to treatment commencing.

The term "antagonizing" used herein is intended to mean "decreasing" or "reducing". A sufficient period of time can be during one week, or between 1 week to 1 month, or between 1 to 2 months, or 2 months or more. For chronic condition, the compound of the present invention can be advantageously administered for life time period.

The term "pulmonary fibrosis" or "lung fibrosis" means the formation or development of excess fibrous connective tissue (fibrosis) in the lung thereby resulting in the development of scarred (fibrotic) tissue. More precisely, pulmonary fibrosis is a chronic disease that causes swelling and scarring of the alveoli and interstitial tissues of the lungs. The scar tissue replaces healthy tissue and causes inflammation. This chronic inflammation is, in turn, the prelude to fibrosis. This damage to the lung tissue causes stiffness of the lungs which subsequently makes breathing more and more difficult.

The term "liver fibrosis" means the formation or development of excess fibrous connective tissue (fibrosis) in the liver thereby resulting in the development of scarred (fibrotic) tissue. The scarred tissue replaces healthy tissue by the process of fibrosis and leads to subsequent cirrhosis of the liver.

The term "skin fibrosis" or "dermal fibrosis" means the excessive proliferation of epithelial cells or fibrous connective tissue (fibrosis) thereby resulting in the development of scarred (fibrotic) tissue. The scarred tissue replaces healthy tissue by the process of fibrosis and may be the prelude of systemic scleroderma. Skin fibrosis is intended to cover the fibrosis of any skin tissue and epithelial cells including, without limitation, blood vessels and veins, internal cavity of an organ or a gland such as ducts of submandibular, gallbladder, thyroid follicles, sweat gland ducts, ovaries, kidney; epithelial cells of gingival, tongue, palate, nose, larynx, oesophagus, stomach, intestine, rectum, anus and vagina; derma, scar, skin and scalp. The compounds of the present invention may be active for promoting healing of wound and one or more of the following activities:

improving collagen organization and/or reducing wound cellularity in said wound;
reducing collagen overproduction by fibroblast and epithelial cells in said wound;
reducing epithelial mesenchymal transition in said wound;
reducing fibroblast migration and activation in said wound;
reducing and/or inhibiting dermal thickening in said wound;
reducing and/or inhibiting recruitment of inflammatory cells to said wound.

The term "cardiac fibrosis" or "heart fibrosis" means an abnormal thickening of the heart valves due to inappropriate proliferation of cardiac fibroblasts but more commonly refers to the proliferation of fibroblasts in the cardiac muscle. Fibrocyte cells normally secrete collagen, and function to provide structural support for the heart. When overactivated this process causes thickening and fibrosis of the valves and heart muscle itself, with white tissue building up primarily on the tricuspid or mitral valve, but also occurring on the pulmonary or aortic valve. The thickening and loss of flexibility eventually may lead to valvular dysfunction and right-sided or left-sided heart failure. In general, prophylactic and therapeutic uses comprise the administration of a compound as described herein to a subject, preferably a human patient in need thereof.

"Idiopathic pulmonary fibrosis (IPF)" is a specific manifestation of idiopathic interstitial pneumonia (IIP), a type of interstitial lung disease. Interstitial lung disease, also known as diffuse parenchymal lung disease (DPLD), refers to a group of lung diseases affecting the interstitium. Microscopically, lung tissue from IPF patients shows a characteristic set of histological features known as usual interstitial pneumonia (UIP). UIP is therefore the pathologic presentation of IPF.

Exemplary forms of fibrosis include, but are not limited to, cardiac fibrosis, liver fibrosis, kidney fibrosis, lung fibrosis, vascular fibrosis, dermal scarring and keloids, and Alzheimer's disease. In still further embodiments, cardiac fibrosis is associated with hypertension, hypertensive heart disease (HHD), hypertensive cardiomyopathy (HCM), myocardial infarction (MI), and restenosis or as a result of impaired renal function resulting from renal fibrosis.

Preferably, the fibrosis is kidney fibrosis. The kidney fibrosis may include, but not be limited to, diabetic nephropathy, vesicoureteral reflux, tubulointerstitial renal fibrosis, glomerulonephritis or glomerular nephritis (GN), focal segmental glomerulosclerosis, membranous glomerulonephritis, or mesangiocapillary GN. The liver fibrosis may include, but not be limited to, cirrhosis, and associated conditions such as chronic viral hepatitis, non-alcoholic fatty liver disease (NAFLD), alcoholic steatohepatitis (ASH), non-alcoholic steatohepatitis (NASH), primary biliary cirrhosis (PBC), biliary cirrhosis, autoimmune hepatitis). Lung fibrosis may include idiopathic pulmonary fibrosis (IPF) or cryptogenic fibrosing alveolitis, chronic fibrosing interstitial pneumonia, interstitial lung disease (ILD), and diffuse parenchymal lung disease (DPLD)). Cardiac fibrosis, congestive heart failure, cardiomyopathy, post-myocardial infarction defects in heart function; peripheral vascular disease; rheumatoid arthritis; glaucoma; age-related macular degeneration (wet AMD and dry AMD); emphysema, chronic obstructive pulmonary disease (COPD); multiple sclerosis; and chronic asthma may also be prevented, treated, or ameliorated with compositions, methods or uses as described herein.

As a result of any method or use as described herein, inhibition of IRAP may improve heart function and decrease infarct area following ischemic-reperfusion (I/R) injury.

In a preferred form, the fibrotic disease is cardiac, renal, liver or interstitial fibrosis.

Scleroderma (systemic sclerosis), a chronic systemic autoimmune disease characterised by hardening (sclero) of the skin (derma) and internal organs (in severe cases). Clinically, patient stratification and drug efficacy can be measured through biopsy/visualization of reduced skin lesions and other objective measures assessed over 24 and 48 weeks. As such, diabetic nephropathy, IgA nephropathy or scleroderma are also fibrotic conditions for treatment and/or prevention.

In the cardiovascular system a progressive age-related deposition of collagen in the vascular wall and in the cardiac interstitial and perivascular space, or collagen deposition related to cardiovascular or renal disease, leads to reduction of myocardial and arterial compliance.

The frequency of administration may be once daily, or 2 or 3 time daily. The treatment period may be for the duration of the detectable disease.

Typically, a therapeutically effective dosage is formulated to contain a concentration (by weight) of at least about 0.1% up to about 50% or more, and all combinations and sub-combinations of ranges therein. The compositions can be formulated to contain one or more compounds according to Formula I, or a pharmaceutically acceptable salt, polymorph or prodrug thereof in a concentration of from about 0.1 to less than about 50%, for example, about 49, 48, 47, 46, 45, 44, 43, 42, 41 or 40%, with concentrations of from greater than about 0.1%, for example, about 0.2, 0.3, 0.4 or 0.5%, to less than about 40%, for example, about 39, 38, 37, 36, 35, 34, 33, 32, 31 or 30%. Exemplary compositions may contain from about 0.5% to less than about 30%, for example, about 29, 28, 27, 26, 25, 25, 24, 23, 22, 21 or 20%, with concentrations of from greater than about 0.5%, for example, about 0.6, 0.7, 0.8, 0.9 or 1%, to less than about 20%, for example, about 19, 18, 17, 16, 15, 14, 13, 12, 11 or 10%. The compositions can contain from greater than about 1% for example, about 2%, to less than about 10%, for example about 9 or 8%, including concentrations of greater than about 2%, for example, about 3 or 4%, to less than about 8%, for example, about 7 or 6%. The active agent can, for example, be present in a concentration of about 5%. In all cases, amounts may be adjusted to compensate for differences in amounts of active ingredients actually delivered to the treated cells or tissue.

Although the invention finds application in humans, the invention is also useful for therapeutic veterinary purposes. The invention is useful for domestic or farm animals such as cattle, sheep, horses and poultry; for companion animals such as cats and dogs; and for zoo animals.

Pharmaceutical compositions may be formulated for any appropriate route of administration including, for example, topical (for example, transdermal or ocular), oral, buccal, nasal, vaginal, rectal or parenteral administration. The term parenteral as used herein includes subcutaneous, intradermal, intravascular (for example, intravenous), intramuscular, spinal, intracranial, intrathecal, intraocular, periocular, intraorbital, intrasynovial and intraperitoneal injection, as well as any similar injection or infusion technique. In certain embodiments, compositions in a form suitable for oral use or parenteral use are preferred. Suitable oral forms include, for example, tablets, troches, lozenges, aqueous or oily suspensions, dispersible powders or granules, emulsions, hard or soft capsules, or syrups or elixirs. Within yet other embodiments, compositions provided herein may be formulated as a lyophilizate.

The various dosage units are each preferably provided as a discrete dosage tablet, capsules, lozenge, dragee, gum, or other type of solid formulation. Capsules may encapsulate a powder, liquid, or gel. The solid formulation may be swallowed, or may be of a suckable or chewable type (either frangible or gum-like). The present invention contemplates dosage unit retaining devices other than blister packs; for example, packages such as bottles, tubes, canisters, packets. The dosage units may further include conventional excipients well-known in pharmaceutical formulation practice, such as binding agents, gellants, fillers, tableting lubricants, disintegrants, surfactants, and colorants; and for suckable or chewable formulations.

Compositions intended for oral use may further comprise one or more components such as sweetening agents, flavouring agents, colouring agents and/or preserving agents in order to provide appealing and palatable preparations. Tablets contain the active ingredient in admixture with physiologically acceptable excipients that are suitable for the manufacture of tablets. Such excipients include, for example, inert diluents such as calcium carbonate, sodium carbonate, lactose, calcium phosphate or sodium phosphate, granulating and disintegrating agents such as corn starch or alginic acid, binding agents such as starch, gelatine or acacia, and lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatine capsules wherein the active ingredient is mixed with an inert solid diluent such as calcium carbonate, calcium phosphate or kaolin, or as soft gelatine capsules wherein the active ingredient is mixed with water or an oil medium such as peanut oil, liquid paraffin or olive oil.

Aqueous suspensions contain the active ingredient(s) in admixture with excipients suitable for the manufacture of aqueous suspensions. Such excipients include suspending agents such as sodium carboxymethylcellulose, methylcellulose, hydropropylmethylcellulose, sodium alginate, polyvinylpyrrolidone, gum tragacanth and gum acacia, and dispersing or wetting agents such as naturally-occurring phosphatides (for example, lecithin), condensation products of an alkylene oxide with fatty acids such as polyoxyethylene stearate, condensation products of ethylene oxide with long chain aliphatic alcohols such as heptadecaethyleneoxycetanol, condensation products of ethylene oxide with partial esters derived from fatty acids and a hexitol such as polyoxyethylene sorbitol mono-oleate, or condensation products of ethylene oxide with partial esters derived from fatty acids and hexitol anhydrides such as polyethylene sorbitan monooleate. Aqueous suspensions may also comprise one or more preservatives, for example ethyl, or n-propyl p-hydroxybenzoate, one or more colouring agents, one or more flavouring agents, and one or more sweetening agents, such as sucrose or saccharin.

Oily suspensions may be formulated by suspending the active ingredients in a vegetable oil such as arachis oil, olive oil, sesame oil or coconut oil, or in a mineral oil such as liquid paraffin. The oily suspensions may contain a thickening agent such as beeswax, hard paraffin or cetyl alcohol. Sweetening agents such as those set forth above, and/or flavouring agents may be added to provide palatable oral preparations. Such suspensions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, such as sweetening, flavouring and colouring agents, may also be present.

Pharmaceutical compositions may also be in the form of oil-in-water emulsions. The oily phase may be a vegetable oil such as olive oil or arachis oil, a mineral oil such as liquid paraffin, or a mixture thereof. Suitable emulsifying agents include naturally-occurring gums such as gum acacia or gum tragacanth, naturally-occurring phosphatides such as soy bean lecithin, and esters or partial esters derived from fatty acids and hexitol, anhydrides such as sorbitan monoleate, and condensation products of partial esters derived from fatty acids and hexitol with ethylene oxide such as polyoxyethylene sorbitan monoleate. An emulsion may also comprise one or more sweetening and/or flavouring agents.

Syrups and elixirs may be formulated with sweetening agents, such as glycerol, propylene glycol, sorbitol or sucrose. Such formulations may also comprise one or more demulcents, preservatives, flavouring agents and/or colouring agents.

Compounds may be formulated for local or topical administration, such as for topical application to the skin. Formulations for topical administration typically comprise a topical vehicle combined with active agent(s), with or without additional optional components.

For any of the fibrotic diseases described herein, when the compound of the present invention is topically administered to a human, the therapeutically effective amount of a compound corresponds to preferably between about 0.01 to about 10% (w/w), or between about 0.1 to 10% (w/w), or between about 1.0 to about 10% (w/w), between about 0.1 to about 5% (w/w), or between about 1.0 to about 5% (w/w). In any of fibrotic diseases described herein, when the compound of the present invention is orally administered to a subject, the therapeutically effective amount of a compound corresponds preferably between about 1 to about 50 mg/kg, or between about 1 to 35 mg/kg. or between about 1 to 25 mg/kg, or between about 1 to about 10 mg/kg, between about 5 to about 25 mg/kg, or between about 10 to about 20 mg/kg.

'Prodrug' means a compound which is convertible in vivo by metabolic means (e.g. by hydrolysis, reduction or oxidation) to a compound of the present invention. For example an ester prodrug of a compound of the present invention containing a hydroxyl group may be convertible by hydrolysis in vivo to the parent molecule. Where esters can be formed, suitable esters are, for example, acetates, citrates, lactates, tartrates, malonates, oxalates, salicylates, propionates, succinates, fumarates, maleates, methylene-bis-β-hydroxynaphthoates, gestisates, isethionates, di-p-toluoyl-tartrates, methanesulphonates, ethanesulphonates, benzenesulphonates, p-toluenesulphonates, cyclohexylsulphamates and quinates.

Prodrugs prepared through common variations to the structure of one or more compounds according to Formula I, II or III, or a pharmaceutically acceptable salt, polymorph or prodrug thereof will be well-known to a person skilled in the art and are included herein. For example, the types of prodrugs described in Zawilska, J. B. et al. Pharmacological Reports, 2013, 65, 1-14 are encompassed in this application where they are relevant to relevant compound's structure and route of administration.

Suitable topical vehicles and additional components are well known in the art, and it will be apparent that the choice of a vehicle will depend on the particular physical form and mode of delivery. Topical vehicles include organic solvents such as alcohols (for example, ethanol, iso-propyl alcohol or glycerine), glycols such as butylene, isoprene or propylene glycol, aliphatic alcohols such as lanolin, mixtures of water and organic solvents and mixtures of organic solvents such as alcohol and glycerine, lipid-based materials such as fatty acids, acylglycerols including oils such as mineral oil, and fats of natural or synthetic origin, phosphoglycerides, sphingolipids and waxes, protein-based materials such as collagen and gelatine, silicone-based materials (both nonvolatile and volatile), and hydrocarbon-based materials such as microsponges and polymer matrices.

A composition may further include one or more components adapted to improve the stability or effectiveness of the applied formulation, such as stabilizing agents, suspending agents, emulsifying agents, viscosity adjusters, gelling agents, preservatives, antioxidants, skin penetration enhancers, moisturizers and sustained release materials.

Examples of such components are described in Martindale—The Extra Pharmacopoeia (Pharmaceutical Press, London 1993) and Martin (ed.), Remington's Pharmaceutical Sciences. Formulations may comprise microcapsules, such as hydroxymethylcellulose or gelatine-microcapsules, liposomes, albumin microspheres, microemulsions, nanoparticles or nanocapsules.

A topical formulation may be prepared in a variety of physical forms including, for example, solids, pastes, creams, foams, lotions, gels, powders, aqueous liquids, emulsions, sprays and skin patches. The physical appearance and viscosity of such forms can be governed by the presence and amount of emulsifier(s) and viscosity adjuster(s) present in the formulation. Solids are generally firm and non-pourable and commonly are formulated as bars or sticks, or in particulate form. Solids can be opaque or transparent, and optionally can contain solvents, emulsifiers, moisturizers, emollients, fragrances, dyes/colorants, preservatives and other active ingredients that increase or enhance the efficacy of the final product. Creams and lotions are often similar to one another, differing mainly in their viscosity. Both lotions and creams may be opaque, translucent or clear and often contain emulsifiers, solvents, and viscosity adjusting agents, as well as moisturizers, emollients, fragrances, dyes/colorants, preservatives and other active ingredients that increase or enhance the efficacy of the final product. Gels can be prepared with a range of viscosities, from thick or high viscosity to thin or low viscosity. These formulations, like those of lotions and creams, may also contain solvents, emulsifiers, moisturizers, emollients, fragrances, dyes/colorants, preservatives and other active ingredients that increase or enhance the efficacy of the final product. Liquids are thinner than creams, lotions, or gels, and often do not contain emulsifiers. Liquid topical products often contain solvents, emulsifiers, moisturizers, emollients, fragrances, dyes/colorants, preservatives and other active ingredients that increase or enhance the efficacy of the final product.

Emulsifiers for use in topical formulations include, but are not limited to, ionic emulsifiers, cetearyl alcohol, non-ionic emulsifiers like polyoxyethylene oleyl ether, PEG-stearate, ceteareth-12, ceteareth-20, ceteareth-30, ceteareth alcohol, PEG-100 stearate and glyceryl stearate. Suitable viscosity adjusting agents include, but are not limited to, protective colloids or nonionic gums such as hydroxyethylcellulose, xanthan gum, magnesium aluminum silicate, silica, microcrystalline wax, beeswax, paraffin, and cetyl palmitate. A gel composition may be formed by the addition of a gelling agent such as chitosan, methyl cellulose, ethyl cellulose, polyvinyl alcohol, polyquaterniums, hydroxyethylceilulose, hydroxypropylcellulose, hydroxypropylmethylcellulose, carbomer or ammoniated glycyrrhizinate. Suitable surfactants include, but are not limited to, nonionic, amphoteric, ionic and anionic surfactants. For example, one or more of dimethicone copolyol, polysorbate 20, polysorbate 40, polysorbate 60, polysorbate 80, lauramide DEA, cocamide DEA, and cocamide MEA, oleyl betaine, cocamidopropyl phosphatidyl PG-dimonium chloride, and ammonium laureth sulfate may be used within topical formulations.

Preservatives include, but are not limited to, antimicrobials such as methylparaben, propylparaben, sorbic acid, benzoic acid, and formaldehyde, as well as physical stabilizers and antioxidants such as vitamin E, sodium ascorbate/ascorbic acid and propyl gallate. Suitable moisturizers include, but are not limited to, lactic acid and other hydroxy acids and their salts, glycerine, propylene glycol, and butylene glycol. Suitable emollients include lanolin alcohol, lanolin, lanolin derivatives, cholesterol, petrolatum, isostearyl neopentanoate and mineral oils. Suitable fragrances and colours include, but are not limited to, FD&C Red No. 40 and FD&C Yellow No. 5. Other suitable additional ingredients that may be included in a topical formulation include, but are not limited to, abrasives, absorbents, anticaking agents, antifoaming agents, antistatic agents, astringents (such as witch hazel), alcohol and herbal extracts such as chamomile extract, binders/excipients, buffering agents, chelating agents, film forming agents, conditioning agents, propellants, opacifying agents, pH adjusters and protectants.

Typical modes of delivery for topical compositions include application using the fingers, application using a physical applicator such as a cloth, tissue, swab, stick or brush, spraying including mist, aerosol or foam spraying, dropper application, sprinkling, soaking, and rinsing. Controlled release vehicles can also be used, and compositions may be formulated for transdermal administration (for example, as a transdermal patch).

A pharmaceutical composition may be formulated as inhaled formulations, including sprays, mists, or aerosols. This may be particularly preferred for treatment of pulmonary fibrosis. For inhalation formulations, the composition or combination provided herein may be delivered via any inhalation methods known to a person skilled in the art.

Such inhalation methods and devices include, but are not limited to, metered dose inhalers with propellants such as CFC or HFA or propellants that are physiologically and environmentally acceptable. Other suitable devices are breath operated inhalers, multidose dry powder inhalers and aerosol nebulizers. Aerosol formulations for use in the subject method typically include propellants, surfactants and co-solvents and may be filled into conventional aerosol containers that are closed by a suitable metering valve.

Inhalant compositions may comprise liquid or powdered compositions containing the active ingredient that are suitable for nebulization and intrabronchial use, or aerosol compositions administered via an aerosol unit dispensing metered doses. Suitable liquid compositions comprise the active ingredient in an aqueous, pharmaceutically acceptable inhalant solvent such as isotonic saline or bacteriostatic water. The solutions are administered by means of a pump or squeeze-actuated nebulized spray dispenser, or by any other conventional means for causing or enabling the requisite dosage amount of the liquid composition to be inhaled into the patient's lungs. Suitable formulations, wherein the carrier is a liquid, for administration, as for example, a nasal spray or as nasal drops, include aqueous or oily solutions of the active ingredient.

Pharmaceutical compositions may also be prepared in the form of suppositories such as for rectal administration. Such compositions can be prepared by mixing the drug with a suitable non-irritating excipient that is solid at ordinary temperatures but liquid at the rectal temperature and will therefore melt in the rectum to release the drug. Suitable excipients include, for example, cocoa butter and polyethylene glycols.

Pharmaceutical compositions may be formulated as sustained release formulations such as a capsule that creates a slow release of modulator following administration. Such formulations may generally be prepared using well-known technology and administered by, for example, oral, rectal or subcutaneous implantation, or by implantation at the desired target site. Carriers for use within such formulations are biocompatible, and may also be biodegradable. Preferably, the formulation provides a relatively constant level of modulator release. The amount of modulator contained within a sustained release formulation depends upon, for example, the site of implantation, the rate and expected duration of release and the nature of the condition to be treated or prevented.

In another embodiment there is provided a kit or article of manufacture including one or more inhibitors of IRAP as described herein, or a pharmaceutically acceptable salt, polymorph or prodrug thereof and/or pharmaceutical composition as described above.

In other embodiments there is provided a kit for use in a therapeutic or prophylactic application mentioned above, the kit including:
  a container holding a therapeutic composition in the form of one or more inhibitors of IRAP as described herein, or a pharmaceutically acceptable salt, polymorph or prodrug thereof or pharmaceutical composition;
  a label or package insert with instructions for use.

In certain embodiments the kit may contain one or more further active principles or ingredients for treatment of a fibrotic disease.

The kit or "article of manufacture" may comprise a container and a label or package insert on or associated with the container. Suitable containers include, for example, bottles, vials, syringes, blister pack, etc. The containers may be formed from a variety of materials such as glass or plastic. The container holds a therapeutic composition which is effective for treating the condition and may have a sterile access port (for example the container may be an intravenous solution bag or a vial having a stopper pierceable by a hypodermic injection needle). The label or package insert indicates that the therapeutic composition is used for treating the condition of choice. In one embodiment, the label or package insert includes instructions for use and indicates that the therapeutic or prophylactic composition can be used to treat a fibrotic disease described herein.

The kit may comprise (a) a therapeutic or prophylactic composition; and (b) a second container with a second active principle or ingredient contained therein. The kit in this embodiment of the invention may further comprise a package insert indicating the composition and other active principle can be used to treat a disorder or prevent a complication stemming from a fibrotic disease described herein. Alternatively, or additionally, the kit may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain embodiments the therapeutic composition may be provided in the form of a device, disposable or reusable, including a receptacle for holding the therapeutic, prophylactic or pharmaceutical composition. In one embodiment, the device is a syringe. The device may hold 1-2 mL of the therapeutic composition. The therapeutic or prophylactic composition may be provided in the device in a state that is ready for use or in a state requiring mixing or addition of further components.

It will be understood, that the specific dose level for any particular patient will depend upon a variety of factors including the activity of the specific compound employed, the age, body weight, general health, sex, diet, time of administration, route of administration, and rate of excretion, drug combination (i.e. other drugs being used to treat the patient), and the severity of the particular disorder undergoing therapy.

It will be understood that the invention disclosed and defined in this specification extends to all alternative combinations of two or more of the individual features mentioned or evident from the text or drawings. All of these different combinations constitute various alternative aspects of the invention.

It will be understood that these examples are intended to demonstrate these and other aspects of the invention and although the examples describe certain embodiments of the invention, it will be understood that the examples do not limit these embodiments to these things. Various changes can be made and equivalents can be substituted and modifications made without departing from the aspects and/or principles of the invention mentioned above. All such changes, equivalents and modifications are intended to be within the scope of the claims set forth herein.

EXAMPLES

Generation of the IRAP Knockout Mice Global IRAP deficient (IRAP$^{-/-}$) mice were generated by Ozgene Pty Ltd, (Perth, Australia) as previously described (Albiston, 2009). Offspring were genotyped by PCR using the oligonucleotides GATAAGATAGTAGGGGAGA (SEQ ID NO: 7), CAATAGAGGTACAGTCACCA (SEQ ID NO: 8) and GGAGAATAAGGGCTGTGAGAGA (SEQ ID NO: 9) (Genetic accession NT_039643) with resultant wildtype allele PCR product of 384 bp and knockout allele of 1041 bp. C57BL/6J mice were used as wild-type (WT) controls. Young mice aged between 4-6 months old and aged mice of 18-22 months old of both strains weighing between 35-50 g were obtained from Monash Animal Research Laboratories (ARL). Mice were fed a normal diet ad libitum and housed in the Pharmacology Animal House, Monash University in standard mouse cages (approximately 4 mice per cage) at 21±1-5° C., with a 12 hour light/dark room. All treatments and experimental procedures were approved by the Monash University Animal Ethics Committee (Ethics #SOBSB/PHAR/2010/23).

Drug Treatment and Surgical Procedures

There are 8 different sets of in vivo experiments in this study:

A) Phenotypic characterisation of the heart and blood vessels in global IRAP knockout mice and their WT controls treated for 4 weeks with Angiotensin (Ang) II (800 ng/kg/min; s.c.) where mouse hearts and blood vessels were compared to tissue obtained from young WT and IRAP$^{-/-}$ mice treated with saline.

B) Prevention of Ang II-induced changes in the cardiovascular system following IRAP inhibitor treatment. In the prevention model, WT mice were treated with Ang II (800 ng/kg/min; s.c.)± the IRAP inhibitor (HFI-419; 500 ng/kg/min for 28 days) or HFI-vehicle (1 DMSO:3 HBC).

C) Phenotypic characterisation of the aged heart, kidney and blood vessels in the global IRAP knockout mice where aged WT and IRAP$^{-/-}$ mouse hearts, kidneys and blood vessels were compared to tissue obtained from young WT and IRAP$^{-/-}$ mice.

D) Reversal of the age-induced changes in the cardiovascular system following IRAP inhibitor treatment. In the reversal model, aged WT mice were treated with either saline, IRAP inhibitor (HFI-419 at 500 ng/kg/min; compound 1 at 500 ng/kg/min; compound 2 at 50 ng/kg/min) or HFI-vehicle (1 DMSO: 3 HBC) for 4 weeks.

E) Prevention of ischemic-reperfusion injury in isolated hearts taken from aged global IRAP knockout mice and aged IRAP inhibitor (HFI-419 at 500 ng/kg/min; s.c.) treated WT mice compared to age-matched vehicle-treated (1 DMSO:3 HBC; s.c.) WT controls.

F) Phenotypic characterization of cardiac function using echocardiography in the aged global IRAP knockout mice compared to aged and young WT mice.

G) Phenotypic characterization of liver steatosis in IRAP knockout mice in a high fat diet (HFD) model.

H) Reversal of the salt-induced fibrosis in the liver following IRAP inhibitor treatment.

All mice which underwent surgery were anaesthetized with Isoflurane (Isorrane) (5% induction and 2.5% maintenance) and an incision made in the midscapular region through which osmotic minipumps (Alzet model 2004, Alza Corp) were inserted for subcutaneous drug administration. The incision area was sutured with 6/0 DY silk (Dynek Pty Ltd) and antibiotic powder applied (Cicatrin, Pfizer) followed by intramuscular injection of the analgesic Cartrophen (0.1 ml of a 1.5 mg/ml stock solution; Biopharm Australia). Systolic blood pressure (SBP) was measured fortnightly using non-invasive tail-cuff plethysmography apparatus (MC4000 Blood Pressure Analysis System, Hatteras Instrument Inc) before drug treatment (week 0), at week 2 of treatment and end of treatment (week 4). At the end of drug treatment, body weight of mice was recorded. Mice were anaesthetized using Isoflurane inhalation and killed by cervical dislocation. Organs (heart, aorta, kidneys, brain, blood and tibia) were collected, with heart and aorta being dissected appropriately as described below. All organs were then snap frozen in liquid nitrogen, and stored at −80° C. if they were not used for vascular reactivity studies conducted on the day mice were killed.

The following procedures were conducted on organs harvested from the above experimental groups:

Cardiac Fibrosis Analysis

To measure collagen deposition, frozen sections of heart, kidney or aorta (all 5 µm thickness) were air dried for 10 minutes and were brought through 3 times xylene (2 minutes each), and 3 times absolute alcohol washes before being rinsed in tap $H_2O$ for seconds. Staining with an optimal concentration of picrosirius red (in this instance 0.05% picrosirius red diluted in saturated picric acid) was performed and left for an hour. Sections were then rinsed in water and differentiated in 0.01M HCl for 2 minutes, followed by dehydration via 3 times absolute alcohol washes. Then, slides were brought through 3 times xylene washes before being cover slipped according to standard histological techniques using DPX as the mounting medium. Images were taken under ×20 magnification, using bright field (Olympus, BX51) and circularized polarized light microscopy (DM IRB, Leica) while percentage of positive interstitial collagen staining per total field of view was quantified using ImageJ 1.46 software (Java, NIH), and averaged out from a total of eight views as the final percentage collagen content in a particular animal.

Gross Cardiac Hypertrophy Analysis

Ventricular weight (VW) was compared to the body weight (BW) as a ratio of VW:BW (mg/g), as well as comparison of VW to tibial length (TL) in as a ratio of VW:TL (mg/mm) respectively. The hearts that were embedded in OCT and frozen were transversely sectioned in a cryostat at 5 µm thickness, and stained with Hematoxylin and Eosin (Amber Scientific) for morphological examination of cell structure. The average of 100 cardiomyocytes per heart section was performed under 60× magnification and analyzed using Image J.

Immunohistochemical Localization of Fibrotic and Inflammatory Markers

Immunostaining was performed on either 5 µm thick transverse frozen heart sections or µm thick frozen thoracic aortic. These sections were air dried and fixed in ice-cold acetone for approximately 15 minutes before washing with 0.01M PBS buffer (3×10 minutes). Sections were then incubated with 10% goat serum in 0.01M PBS for 30 minutes to reduce non-specific binding. If the primary antibody is raised in goat, this pre-blocked medium is substituted with 5% BSA in PBS and Triton-X. Next, blocking buffers were removed and the primary antibody to respective markers were applied overnight at room temperature based on the following dilution and origin of the antibodies: IRAP (1:500, in-house), α-SMA (1:500, Abcam), Vimentin (1:500, Santa Cruz), P-IκBα (1:200, Cell Signalling), F4/80 macrophage (1:100, Serotec), MCP-1 (1:100, Santa Cruz), VWF (1:500, abcam). After 4 series of washes in ice-cold PBS on second day, appropriate secondary antibodies were incubated with mainly Alexa 488 (Invitrogen or Abcam), Alexa 594 (Invitrogen) and Fluorescein FI-5000 (Vector) being used. With primary antibodies raised in mouse, another immunofluorescence technique was performed using the mouse on mouse (M.O.M) kit (Vector) on heart sections based on the following dilution and origin of the antibodies: TGF-β (1:50, Santa Cruz), ICAM-1 (1:100, Santa Cruz). All immunofluorescent sections were viewed under ×20 magnification on an Olympus, BX51 microscope and images analyzed using Image J.

Histochemical Localization of Cardiac and Vascular Superoxide

Dihydroethidium (DHE) was used to localize superoxide in situ. 5 µm heart sections or µm thoracic aortic sections were incubated with 2 µM DHE for 45 minutes at 37° C. Adjacent section was pre-incubated with PEG-SOD (1000 U/mL) for 30 minutes prior to the 45 minutes incubation with DHE to confirm specificity of the fluorescent signal for superoxide. Fluorescence of the product 2-hydroxyethidium was imaged using inverted confocal microscope (Nikon, C1) under excitation emission spectrum of 568 nm and 585 nm respectively. Laser settings were identical for each image acquired and integrated density of the fluorescence was quantified using ImageJ.

Determination of Tissue Protein Expression by Western Blot Analysis

Total proteins from homogenized ventricles were extracted using 1.5× Laemmli buffer containing 25% Glycerol, 7.5% SDS, 250 mM Tris-HCl at pH 6.8, and 0.001 g bromophenol blue. Homogenized samples were sonicated followed by heating at 37° C. for 20 minutes and centrifuged at 13,000 rpm for 30 minutes at 4° C. RCDC assay was performed and the protein content was quantified using ProteinQuant-Lowry software (SoftMax Pro) at 750 nm. Finally, samples were stored at −20° C. Western blot was performed firstly with samples (10 or 25 µg/µl/sample) being electrophoresed, transferred, and probed with primary antibody TGF-β (25 kDA, 1:2000, Santa Cruz), MMP-2 (72 kDA, 1:2000, Millipore), MMP-8 (65 kDA, 1:2000, Santa Cruz), MMP-9 (84 kDA, 1:1000, Chemicon), MMP-13 (54 kDA, 1:100, Abcam), ICAM-1 (85-110 kDA, 1:200, Santa Cruz), GAPDH (36 kDA, 1:20000, Abcam). The secondary antibodies were HRP-conjugated goat anti-mouse IgG (1:10000, Jackson ImmunoResearch) or anti-rabbit IgG (1:10000, DAKO), followed by development with ECL reagent. Membranes were exposed to CLxPosure film (Pierce, Rockford, Ill.). Immunoreactive bands were then quantified using chemiDoc XRS imager and Quantity One software (BioRad). Individual bands were quantified using bands intensity per area and were then normalized to the intensity per area of the housekeeping gene GAPDH.

Quantification of Cytokine Expression Profile by Bioplex Multiplex System

The levels of cytokines in the heart ventricles and apex were detected by using the Bio-Plex multiplex assay (Biorad). Tissues were snap-frozen and homogenized with a Bio-Plex cell lysis kit (Biorad) according to the manufacturer's instructions. Briefly, tissues were washed once with 300 µl of wash buffer and homogenized in lysing solutions using Tissue Lyser (Qiagen). Samples were left on ice for 30 min and centrifuged at 6,000×g for 20 min at 4° C. Supernatant was collected and protein content was determined using Biorad protein assay (Biorad). 500 µg/ml of protein were used to detect the levels of cytokines. A panel of Bio-Plex Pro™ Mouse Cytokine Standard 23-Plex, Group I (IL-1α, IL-1β, IL-2, IL-3, IL-4, IL-5, IL-6, IL-9, IL-10, IL-12(p40), IL-12(p70), IL-13, IL-17A, Eotaxin, G-CSF, GM-CSF, IFN-γ, KC, MCP-1, MIP-1α, MIP-1β, RANTES, TNFα) was used, containing 23 different antibodies covalently coupled to the beads. 50 µl of sample (500 µg/ml) or known standard (200-900 µg/ml) was added to wells of a 96-well plate which was pre-coated with the diluted coupled beads specific for each antibody and incubated at RT with shaking at 300 RPM for 30 min in the dark. After washing away any unbound substances, biotinylated detection antibodies were added to create a sandwich complex and the plate was incubated for 30 min with shaking at 300 RPM in the dark at RT. Following three washes, the final detection complex was formed with the addition of streptavidin-phycoerythrin conjugate and incubated for 10 min in the dark at RT with shaking at 300 RPM. Following 3 washes with 100 µl wash buffer, beads were resuspended in 125 µl of assay buffer. The samples were read using Bio-Plex MAGPIX Multiplex Reader (Bio-Plex Suspension System). Data were calculated by the Bio-Plex Manager software.

Determination of Gelatinases Activity by Gel Zymography

Homogenized heart apex in 0.25% Triton X-100 dissolved in 10 mM $CaCl_2$) and centrifuged at 6000 rpm for 30 minutes at 2° C. Pellet undergoes heat extraction in 0.1M $CaCl_2$) at 60° C. for 4 minutes, followed by chilling in ice and centrifuged at 20000 rpm for 30 minutes at 4° C. Supernatant was sieved using concentrator (company) and stored at −20° C. MMP zymography was performed by firstly with samples (25 µg/µl/sample) being electrophoresed. Gels were then washed twice with 0.25% Triton X-100 for 15 minutes each, then left for overnight incubation in incubation buffer at 37° C. Gels were stained with 0.1 Coomasie blue for an hour followed by destain with 7% acetic acid the next day. Optical density of bands was then quantified using chemiDoc XRS imager and Quantity One software (BioRad).

Determination of Cardiac Function by Langendorff Isolated Heart Preparation Mice were injected with heparin (500 IU) 20 min before death by cervical dislocation. The heart was rapidly excised and immersed in ice-cold physiological saline solution (PSS). Under a dissecting microscope, the heart and aortic arch were cleared of loose tissue, the pulmonary vein perforated to permit free perfusion of the heart and the heart was mounted on a Langendorff apparatus (ML870B2, ADInstruments, Bella Vista, NSW, Australia) via a 20 gauge needle. The heart was continuously perfused with pre-warmed PSS containing (mM): NaCl 118; KCl 4.7; $NaHCO_3$ 25; glucose 11; $KH_2PO_4$ 1.2; $MgSO_4$ 1.2; $CaCl_2$) 1.2 mM and gassed with $O_2$ 95% and $CO_2$ 5% (carbogen) at 37° C. Prior to use, the PSS was filtered through a 0.22 µm cellulose acetate filter (Millipore). The heart perfusion chamber was surrounded by thermostatically controlled water jacket system that maintained the temperature at 37° C. A fine, 200 µm cannula was present in the PSS line for drug delivery (1:10 drug dilution and with a time lag of 1 min to the heart). A Millar pressure cathether (Millar instruments Inc.) was introduced into the left ventricle via a puncture at the junction of the left atrium and ventricle, and connected to a Power lab system (ADInstruments). Perfusion pressure was maintained at 80 mmHg and the preparation was left to equilibrate for 20-30 min. Left ventricular developed pressure (LVDP); end diastolic pressure (EDP), heart rate (HR), left ventricular contractility (+dP/dt) and left ventricular relaxation (−dP/dt) and coronary flow were recorded continuously.

Determination of Ischemic-Reperfusion Injury in the Isolated Langendorff Heart Preparation Ischemia was induced by halting perfusion of the heart for 40 min. This was followed by 60 min of reperfusion. Left ventricular developed pressure (LVDP), end diastolic pressure (EDP) and contractility (±dP/dt) were recorded during the 60 min. The heart was removed from the Langendorff apparatus and stopped in diastole by placing in high potassium (100 mM) PSS for 3 min. It was then glued to a mounting block (via the atria), supported by agar blocks and 1 mm thick slices were cut (Integraslice 7550MM (Campden Instruments, UK). The slices were placed in 2,3,5-triphenyltetrahydrozolium (TTZ 10 mg/ml) and incubated at 37° C. for 15 min. The slices were stored in 4% paraformaldehyde in phosphate-buffered saline and photographed within 24 hr. Infarct area was determined using ImageJ software (Centre for Information Technology, NIH, Bethesda, Mass., USA). Infarct area was calculated as:

$$\text{Infarct area (\%)} = (\text{total infarct area} \times 100)/(\text{total slice area} - \text{luminal area}).$$

Determination of Cardiac Function by Echocardiography

Echocardiography was performed on young (3 month old) and aged (~22 month old) WT and aged (~22 month old) global IRAP deficient mice under light sedation (1% isoflurane in oxygen). Echocardiography was performed using a 18 to 38 MHz linear-array transducer with a digital ultrasound system (Vevo 2100 Imaging System, VisualSonics, Toronto, Canada). Standard parasternal long- and short-axis views were obtained during each echocardiographic examination with conventional echocardiographic measurements performed offline by a blinded observer. VisualSonics, Toronto, Canada).

Human Cardiac Fibroblast Cell Culture Studies

Commercially available human cardiac fibroblasts (HCF, Catalog #6300, Sciencell, CA, USA) were grown in T75 flask maintained in an incubator at 37° C., 5% $CO_2$ Complete media composition: M199 media (#11150-059, life technologies)+10% FBS (#10437-028, life technologies)+1% Fibroblast Growth Supplement-2 (#2382, ScienCell)+1% penicillin/streptomycin 10,000 U/ml antibiotics (#15140-122, Life Technologies). Fresh complete media was replenished every alternate day until culture reached 70% confluence in which media is replenished daily until it reached approximately 90% confluence in order to passage/subculture. To subculture, media was discarded and culture was rinsed with warm PBS. After which, culture was detached using warm 0.05% Trypsin+ EDTA with gentle swirling of flask to make sure cells were not adherent to surface of flask. Trypsin was then neutralized with complete media and suspension was then transferred into a new falcon tube and centrifuged at 1000 rpm for 5 minutes. Supernatant was discarded and pellet of cells were resuspended with 5 ml of complete media, followed by cell counting. For subculturing/passaging, 1 million HCFs are placed into a T75 flask. For Picrosirius Red (PSR) staining or immunofluorescence experiments, 100 k cells were loaded per well in a 24 well plate lined with round coverslips. For western blot analysis experiments, 100 k cells were loaded per well in a 12 well plate. Passage 3-6 cells had been used for experiments with the pro-fibrotic agent Angiotensin II (Ang II; $10^{-8}$M $10^{-7}$M $10^{-6}$M) added in complete media at the time when cells were being passaged and plated. All duration of treatment was approximately 72 hours. Once treatment is done, media was collected and cells were treated differently depending on the type of experiments as follow:

A) Picrosirius Red (PSR) Staining

Cells were initially grown on coverslips, washed with warm PBS once and fixed in ice-cold methanol overnight at −20° C. The next day, methanol was discarded and cells were washed once with cold PBS and incubated with 0.1% PSR solution for 1 hour at room temperature. After this, the dye was removed and cells were washed 3 times with 0.1% acetic acid, followed by dehydration with 3 changes of 100% ethanol (5 minutes each) and 3 times with xylene (10 minutes each). Coverslips were removed and mounted on slides using DPX mounting medium.

B) Immunofluorescence:

Cells were grown on coverslips, washed with warm PBS once and fixed in ice-cold acetone for 5 minutes at −20° C. Once acetone was discarded, cells were rinsed in PBS, 3×10 minutes at room temperature. Cells were then blocked with 10% goat serum for 30 minutes at room temperature, followed by overnight incubation with primary antibody (1:500 dilution) at 4° C. The next day, primary antibody was removed and cells were rinsed with PBS 3×10 minutes at room temperature. Cells were then incubated with secondary antibody (1:500 dilution) for 2 hours at room temperature. Cells were then again rinsed with PBS 3×10 minutes at room temperature. Coverslips were removed from 24 well plate and mounted on slides using Vectashield mounting medium with DAPI, left to dry prior to imaging under confocal microscope.

C) Western Blot Analysis:

i. Protein Extraction:

Once treatment is complete, cells were washed with warm PBS and detached using Accutase (A6964, Sigma), with 5 minutes incubation at 37° C. Cells were then collected and centrifuged at 7000 rpm for 5 minutes at 4° C. During this time, 1×RIPA lysis buffer cocktail was prepared fresh. After centrifugation, supernatant was discarded. Cell pellet was then lysed in 20 ul of 1×RIPA lysis buffer cocktail and kept on ice for 30 minutes. After that, the cell lysate was centrifuged at 13200 rpm for 10 min at 4° C. to pellet nuclei and any insoluble cell debris. The supernatant (~20 ul) was transferred to a new tube and protein concentrations were measured using Biorad Lowry protein assay. Protein quantification of respective markers were performed via standard western blot analysis.

ii. Western Blotting:

10% gels (15 wells) were made up using TGX Stain-Free FastCast Acrylamide starter kit, 10% (#161-0183, Biorad). Samples were prepared by diluting 3 parts sample with 1 part of 4× sample buffer, ie. add 10 ul of extracted protein samples (half of total extracted proteins) into 3.3 ul of 4×Laemli sample buffer (#161-0747, Biorad). Keep samples on ice at all times up till this step. Boil samples at 95° C. for 5 minutes. Load all samples onto the wells gel, along with a protein ladder. Make up 1× Running buffer from 10× buffer (#161-0732, Biorad). Top up tank and run samples at 200V for ~40 mins-1 hour. Terminate gel electrophoresis once the desired protein bands have been separated appropriately. Prepare sandwich stacks and membrane (pre-soak membrane in methanol for ~10s), then soak them all in 1× Trans-Blot Turbo Transfer buffer (#170-4272). Lay a stack of wetted stack on bottom of cassette (bottom ion reservoir stack), followed by wetted membrane, then the gel and lastly with another wetted transfer stack at the top (top ion reservoir stack). Roll the assembled sandwich with blot roller to expel trapped air bubbles. Close and lock cassette lid and insert cassette in the Transfer-Blot Turbo transfer system and begin transfer. Once transfer is completed, wash membranes briefly in TBS-T (0.1% Tween-20 in 1×TBS). Block membranes in blocking buffer (TBS-T/5% skim milk; 5 g/100 ml) for at least 1 hour at room temperature on a mechanical shaker. Replace and incubate the membrane overnight with primary antibody at 4° C. Next day, wash membrane 3×15 minutes in TBS-T. Incubate secondary antibody in 5% skim milk for 1 hour at room temperature on shaker. Wash 3×15 minutes in TBS-T. Incubate membrane with ECL substrate for 5 minutes. Image the membrane with a digital imager ChemiDoc MP imaging system. Bands were analyzed using Image Lab software. Marker of interest such as α-smooth muscle actin (α-SMA) and collagen type I were quantified against housekeeping gene GAPDH. All protein expressions were assessed as a relative ratio to the control group.

Liver Fibrosis—Experimental Design

Animals

Male C57BL/6J wild type (WT) mice aged approximately 4 to 6 months weighing 30-40 grams were obtained from Monash Animal Research Laboratory. Animals were housed in the Animal House in the Department of Pharmacology, Monash University, in standard cages where they were initially maintained on a normal diet. The housing was maintained at roughly 21° C.±5° C. with mice exposed to a 12 hour light/dark cycle, and access to food and water ad libitum. Experimental procedures undertaken were approved and certified by the School of Biomedical Sciences (SOBS) Animal Ethics Committee of Monash University (2013/118).

Experimental Model

A high-salt diet (5% salt) model is a clinically relevant and disease-reversal model which can replicate the high salt intake by humans which is currently a growing problem in the developed countries. High salt intake induces changes in the cardiovascular system and induces remodelling and fibrosis in the heart and liver.

WT mice were placed on a normal rodent diet (ND; 0.5% NaCl) which acted as control or a high salt diet (HSD; 5% NaCl) for a period of 4 weeks. After 4 weeks mice on the HSD were randomised to receive either Vehicle (DMSO/30% HBC solution) or IRAP inhibitor (HF419; 0.72 mg/kg/d) with both vehicle and IRAP inhibitor administered via s.c. osmotic mini-pump. Mice continued to be fed a HSD whilst receiving these treatments. At the end of the 8 week treatment period mice were weighed before being killed by overdose of isoflurane inhalation. The liver was removed and sectioned with half of the liver placed in 10% formalin and the rest frozen in liquid nitrogen before being stored in −80° C. freezer for future use.

Assessment of Liver Fibrosis

Formalin fixed, paraffin embedded livers were sectioned at thickness of 4 μm and were stained with Masson's trichrome according to standard procedures for analysis of liver fibrosis. Initially sections were deparaffinised and rehydrated through 100% alcohol, 95% alcohol and 75% alcohol washes then washed in distilled water. Sections were re-fixed in Bouin's solution for 1 hour at 56° C. to improve staining quality then rinsed in running tap water for 5-10 minutes to remove yellow colour. Following this, sections were stained in Weigert's iron hematoxylin working solution for 10 minutes. Rinsed in running warm tap water for 10 minutes. Washed in distilled water. Stained in Biebrich scarlet-acid fuchsin solution for 10-15 minutes. Washed in distilled water. Differentiated in phosphomolybdic-phosphotungstic acid solution for 10-15 minutes or until collagen was no longer red. Sections were transferred directly (without rinse) to aniline blue solution and stained for 5-10 minutes. Rinsed briefly in distilled water and differentiated in 1% acetic acid solution for 2-5 minutes. Washed in distilled water. Dehydrated very quickly through 95% ethyl alcohol, absolute ethyl alcohol and clear in xylene. Mounted with DPX mounting medium.

Quantification of liver fibrosis was performed using images captured with the Aperio scanner (Monash Histology Platform, Monash University), with ×5 magnification. Each liver section had 5 different fields of view photographed at this magnification. Percentage of interstitial and perivascular collagen was analysed and quantified using ImageJ 1.48 software (Java, NIH), and the percentage from 5 random fields of view were averaged for final percentage of collagen for that particular animal. All analysis of collagen expression was conducted in a blinded fashion.

Statistical Analysis

Results were expressed as mean±standard error of mean (SEM). All statistical plots and analysis were performed using the Prism program (GraphPad Software Inc. San Diego, Calif., USA). All statistical comparison (cardiac hypertrophy, collagen deposition, all IHC quantifications and western blot analysis) between aged WT and IRAP KO mice in aged models or comparison between vehicle-treated aged WT and HFI-419 treated aged WT in the reversal model was conducted using T-test. For all data sets comparing between young and aged WT or IRAP$^{-/-}$ as well as data in the endothelial vasodilator function were compared using 2-way analysis of variance (ANOVA) followed by post-hoc Bonferroni corrections as appropriate. In the Langendorff isolated heart perfusion experiment, equality of standard deviations and Gaussion distribution, using the Kolmogorov/Smirnov method, were tested. One- and two-way ANOVA with post hoc Bonferonni testing was performed on basal recordings of LVDP, EDP, HR, ±dP/dt, while the LVDP and EDP post ischaemia-reperfusion were assessed using 2-way ANOVA.

Compounds

| Number | Structure |
| --- | --- |
| HFI-419 | (structure) |
| Compound 1 | (structure) |
| Compound 2 | (structure) |

HFI-419, compound 1 and Compound 2 were synthesised according to WO2009065169, AU 2015901676 and Andersson et al J. Med. Chem., (2010) 53, 8059 respectively. The synthesis of some of the compounds are listed below and their inhibitory activity described in PGT/AU2016/050332.

General Information

All reagents and solvents were used as received. Proton nuclear magnetic resonance ($^1$H n.m.r.) spectra were recorded at 300 MHz with a Bruker Advance DPX-300 or at 400 MHz using a Bruker Ultrashield-Advance III NMR spectrometer. The $^1$H n.m.r. spectra refer to solutions in deuterated solvents as indicated. The residual solvent peaks have been used as an internal reference, with each resonance assigned according to the following convention: chemical shift (δ) measured in parts per million (ppm) relative to the residual solvent peak. High Resolution Mass Spectrometry analyses were collected on a Bruker Apex II Fourier Transform Ion Cyclotron Resonance Mass Spectrometer fitted with an electrospray ion source (ESI). Low Resolution Mass Spectrometry analyses were performed using a Micromass Platform II single quadrupole mass spectrometer equipped with an atmospheric pressure (ESI/APCI) ion source.

Liquid Chromatography Mass Spectra (LCMS) were measured on a Shimadzu 2020 LCMS system incorporating a photodiode array detector (214 nm unless otherwise stated) coupled directly into an electrospray ionisation source and a single quadrupole mass analyser. Standard RP-HPLC was carried out at room temperature employing a Phenomenex Luna C8 (100×2.0 mm I.D.) column eluting with a gradient of 0-64% CH3CN in 0.05% aqueous trifluoroacetic acid over 10 min at a flow rate of 0.2 ml/min unless stated otherwise. Mass spectra were obtained in positive mode with a scan range of 200-2000 m/z. Analytical HPLC was performed on a Waters 2690 HPLC system incorporating a diode array detector (254 nm), employing a Phenomenex column (Luna C8(2), 100×4.5 mm ID) eluting with a gradient of 16-80% acetonitrile in 0.1% aqueous trifluoroacetic acid, over 10 minutes at a flow rate of 1 ml/min. Analytical thin layer chromatography (t.l.c.) was performed on Merck aluminium sheets coated in silica gel 60 F254 and visualization accomplished with a UV lamp. Column chromatography was carried out using silica gel 60 (Merck). Purity of compounds (≥95%) was established by either reverse phase HPLC or 1H n.m.r.

General Method

Piperidine (cat.) was added to a solution of malononitrile (1.1 eq.) and aldehyde (1 eq.) in EtOH (3-5 mL) and stirred at ambient temperature for 15 min. Ethyl acetoacetate (1.1 eq.) was added and the mixture stirred at ambient temperature for 4 hrs. The volume of solvent was reduced and the resulting precipitate was collected and washed with cold EtOH to give the title compound. If required, the compound was recrystallised from hot EtOH or triturated with DCM.

4-(2-Amino-3-cyano-5-(ethoxycarbonyl)-6-methyl-4H-pyran-4-yl)benzoicacid

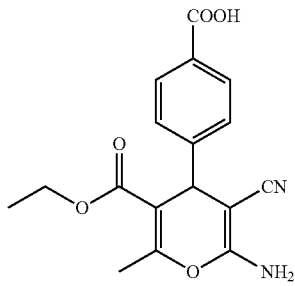 [SMILES: CCOC(=O)C1=C(C)OC(N)=C(C#N)C1c1ccc(C(=O)O)cc1]

Following the general method, 4-carboxybenzaldehyde (1.0 g, 6.6 mmol), malononitrile (0.48 g, 7.3 mmol), ethyl acetoacetate (0.95 g, 7.3 mmol), piperidine (8 drops), and ethanol (20 mL), gave the title compound as a white solid (1.7 g, 78%). 1H NMR (300 MHz, MeCOH) δ 7.96 (d, J=7.2 Hz, 2H), 7.29 (d, J=7.2 Hz, 2H), 4.46 (s, 1H), 4.02 (q, J=6.9 Hz, 2H), 2.39 (s, 3H), 1.08 (t, J=6.7 Hz, 3H). MS (ESI) m/z: 329.4 (M+H)+(65%).

3-(2-Amino-3-cyano-5-(ethoxycarbonyl)-6-methyl-4H-pyran-4-yl)benzoicacid

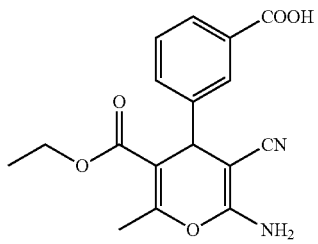 [SMILES: CCOC(=O)C1=C(C)OC(N)=C(C#N)C1c1cccc(C(=O)O)c1]

Following the general method, 3-carboxybenzaldehyde (100 mg, 0.66 mmol), malononitrile (48 mg, 0.73 mmol), ethyl acetoacetate (95 mg, 0.73 mmol), piperidine (drops), and ethanol (3 mL), gave the title compound after recystallistation from EtOH as a white solid (41 mg, 19%). 1H NMR (600 MHz, MeOD) δ 7.89 (d, J=7.2 Hz, 1H), 7.86 (s, 1H), 7.45-7.41 (m, 2H), 4.46 (s, 1H), 4.07-3.98 (m, 2H), 2.39 (s, 3H), 1.09 (t, J=7.1 Hz, 3H). MS (ESI) m/z: 329.4 (M+H)+ (80%).

Ethyl 4-(4-acetoxy-3-methylphenyl)-6-amino-5-cyano-2-methyl-4H-pyran-3-carboxylate

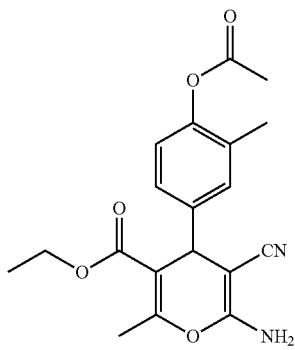 [SMILES: CCOC(=O)C1=C(C)OC(N)=C(C#N)C1c1ccc(OC(C)=O)c(C)c1]

Following the general method, 4-formyl-2-methylphenyl acetate (100 mg, 0.56 mmol), malononitrile (41 mg, 0.67 mmol), ethyl acetoacetate (80 mg, 0.67 mmol), piperidine (3 drops), and ethanol (5 mL), gave the title compound as a white solid (87 mg, 44%). 1H NMR (300 MHz, CDCl$_3$) δ 7.04-6.99 (m, 2H), 6.93 (d, J=7.9 Hz, 1H), 4.46 (bs, 2H), 4.41 (s, 1H), 4.15-3.95 (m, 2H), 2.37 (s, 3H), 2.29 (s, 3H), 2.14 (s, 3H), 1.12 (t, J=7.1 Hz, 3H). MS (ESI) m/z: 357.3 (M+H)+(50%); 713.6 (2M+H)+(100%).

Ethyl 4-(4-acetoxy-3,5-dimethylphenyl)-6-amino-5-cyano-2-methyl-4H-pyran-3-carboxylate

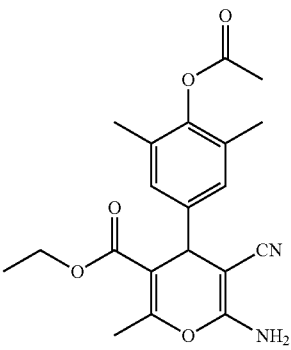 [SMILES: CCOC(=O)C1=C(C)OC(N)=C(C#N)C1c1cc(C)c(OC(C)=O)c(C)c1]

Following the general method, 4-formyl-2,6-dimethylphenyl acetate (85 mg, 0.44 mmol), malononitrile (32 mg, 0.49 mmol), ethyl acetoacetate (63 mg, 0.49 mmol), piperidine (2 drops), and ethanol (3 mL), gave the title compound as a white solid (146 mg, 90%). 1H NMR (300 MHz, CDCl$_3$) δ 6.85 (s, 2H), 4.47 (bs, 2H), 4.37 (s, 1H), 4.19-3.94 (m, 2H), 2.37 (s, 3H), 2.31 (s, 3H), 2.11 (s, 6H), 1.12 (t, J=7.0 Hz, 3H). MS (ESI) m/z: 371.4 (M+H)+(55%); 740.8 (2M+H)+(100%).

Ethyl 6-amino-5-cyano-2-methyl-4-(4-(pyridin-2-yl)phenyl)-4H-pyran-3-carboxylate

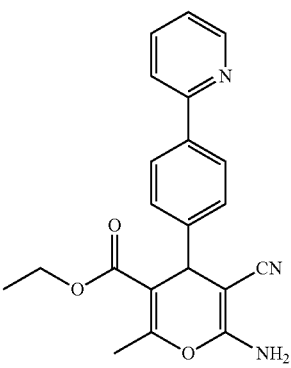 [SMILES: CCOC(=O)C1=C(C)OC(N)=C(C#N)C1c1ccc(-c2ccccn2)cc1]

Following the general method, 4-(2-pyridyl)benzaldehyde (250 mg, 1.36 mmol), malononitrile (99 mg, 1.50 mmol), ethyl acetoacetate (195 mg, 1.50 mmol), piperidine (3 drops), and ethanol (5 mL), gave the title compound as a white solid (410 mg, 83%). 1H NMR (300 MHz, CDCl$_3$) δ 8.71-8.64 (m, 1H), 7.93 (d, J=8.4 Hz, 2H), 7.79-7.67 (m, 2H), 7.31 (d, J=8.4 Hz, 2H), 7.22 (ddd, J=6.6, 4.8, 1.6 Hz, 1H), 4.52 (s, 1H), 4.47 (s, 2H), 4.03 (q, J=7.1 Hz, 2H), 2.40 (d, J=0.9 Hz, 3H), 1.11 (t, J=7.1 Hz, 3H). MS (ESI) m/z: 362.6 (M+H)+(100%).

Ethyl 6-amino-5-cyano-2-methyl-4-(quinoin-2-yl)-4H-pyran-3-carboxylate

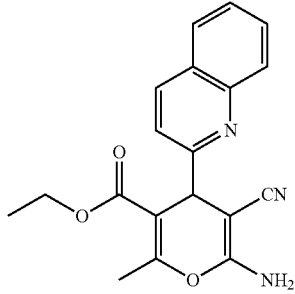 [SMILES: CCOC(=O)C1=C(C)OC(N)=C(C#N)C1c1ccc2ccccc2n1]

Following the general method, 2-quinoline carboxaldehyde (250 mg, 1.59 mmol), malononitrile (115 mg, 1.75 mmol), ethyl acetoacetate (228 mg, 1.75 mmol), piperidine (3 drops), and ethanol (5 mL), gave the title compound as a white solid after recrystallization (302 mg, 57%). 1H NMR (300 MHz, DMSO) δ 8.32 (d, J=8.5 Hz, 1H), 7.98-7.90 (m, 2H), 7.73 (ddd, J=8.5, 6.9, 1.4 Hz, 1H), 7.56 (ddd, J=8.0, 6.9, 1.2 Hz, 1H), 7.40 (d, J=8.4 Hz, 1H), 6.98 (s, 2H), 4.63 (d, J=1.0 Hz, 1H), 3.89 (qd, J=7.1, 2.7 Hz, 2H), 2.38 (d, J=0.8 Hz, 3H), 0.88 (t, J=7.1 Hz, 3H). MS (ESI) m/z: 336.4 (M+H)+(100%).

Ethyl 6-amino-5-cyano-2-methyl-4-(quinoin-3-yl)-4H-pyran-3-carboxylate

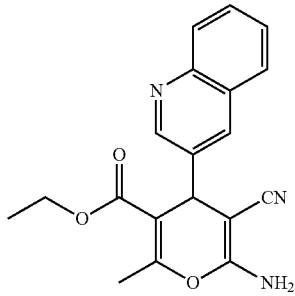 [SMILES: CCOC(=O)C1=C(C)OC(N)=C(C#N)C1c1cnc2ccccc2c1]

Following the general method, 3-quinoline carboxaldehyde (50 mg, 0.32 mmol), malononitrile (23 mg, 0.35 mmol), ethyl acetoacetate (45 mg, 0.35 mmol), piperidine (1 drop), and ethanol (3 mL), gave the title compound as a white solid (85 mg, 79%). 1H NMR (300 MHz, CDCl₃) δ 8.80 (s, 1H), 8.08 (d, J=8.4 Hz, 1H), 7.96 (s, 1H), 7.80 (d, J=8.2 Hz, 1H), 7.69 (t, J=7.6 Hz, 1H), 7.54 (t, J=7.5 Hz, 1H), 4.67 (s, 1H), 4.62 (bs, 2H), 4.03 (q, J=7.0 Hz, 2H), 2.43 (s, 3H), 1.11 (t, J=7.0 Hz, 3H). MS (ESI) m/z: 336.4 (M+H)+ (100%).

Ethyl 6-amino-5-cyano-2-methyl-4-(quinoin-4-yl)-4H-pyran-3-carboxylate

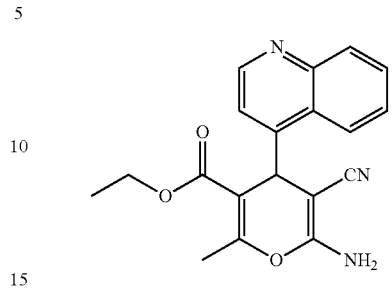

Following the general method, 4-quinoline carboxaldehyde (250 mg, 1.59 mmol), malononitrile (115 mg, 1.75 mmol), ethyl acetoacetate (228 mg, 1.75 mmol), piperidine (2 drops), and ethanol (5 mL), gave the title compound as a white solid (395 mg, 74%). 1H NMR (300 MHz, CDCl₃) δ 8.86 (d, J=4.3 Hz, 1H), 8.31 (d, J=8.5 Hz, 1H), 8.12 (d, J=8.4 Hz, 1H), 7.73 (t, J=7.5 Hz, 1H), 7.62 (t, J=7.6 Hz, 1H), 7.20 (d, J=4.4 Hz, 1H), 5.38 (s, 1H), 4.60 (bs, 2H), 3.92-3.73 (m, 2H), 2.48 (s, 3H), 0.73 (t, J=7.1 Hz, 3H). MS (ESI) m/z: 336.2 (M+H)+(100%).

4-(2-Amino-3-cyano-5-(methoxycarbonyl)-6-methyl-4H-pyran-4-yl)benzoic acid

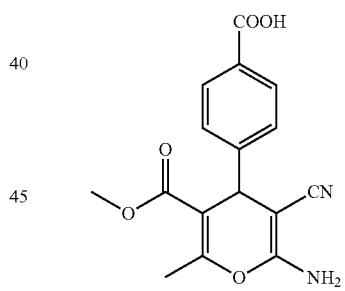

Piperidine (2 drops) was added to a suspension of 4-(2,2-dicyanovinyl)benzoic acid (200 mg, 1.01 mmol) and methyl acetoacetate (117 mg, 1.01 mmol) in EtOH (3 mL). The mixture was stirred at ambient temperature for 6 h. The resulting precipitate was collected and washed with cold EtOH to give a white solid (117 mg). Column chromatography (SiO₂, EtOAc:MeCOH, 9:1) afforded the title compound as white solid (78 mg, 25%). 1H NMR (400 MHz, MeOD) δ 7.96 (d, J=8.2 Hz, 2H), 7.29 (d, J=8.3 Hz, 2H), 4.46 (s, 1H), 3.57 (s, 3H), 2.39 (s, 3H). LCMS (ESI) m/z: 315.1 (M+H)+(100%).

4-(2-Amino-5-(benzyloxycarbonyl)-3-cyano-6-methyl-4H-pyran-4-yl)benzoicacid

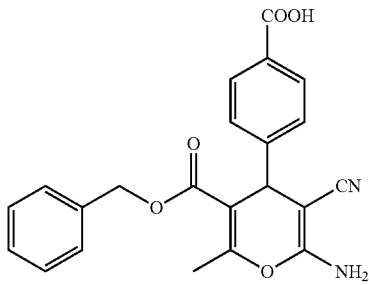 [SMILES: CC1=C(C(=O)OCc2ccccc2)C(c2ccc(C(=O)O)cc2)C(C#N)=C(N)O1]

(i) 4-(2,2-dicyanovinyl)benzoic acid

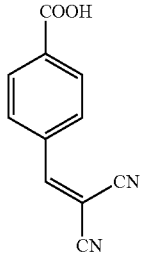

Piperidine (66 µL, 0.67 mmol) was added to a mixture of malononitrile (480 mg, 7.27 mmol) and 4-carboxybenzaldehyde (1.0 g, 6.65 mmol) in EtOH (5 mL). The suspension was heated to reflux for 18 h. After cooling the solvent was removed in vacuo and taken up in toluene. The resulting precipitate was collected and washed with toluene and cold EtOH to give the intermediate as a pale yellow solid (1.28 g, 85%). 1H NMR (400 MHz, MeOD) δ 8.29 (s, 1H), 8.17 (d, J=8.5 Hz, 2H), 8.04 (d, J=8.3 Hz, 2H).

(ii) 4-(2-amino-5-(benzyloxycarbonyl)-3-cyano-6-methyl-4H-pyran-4-yl)benzoic acid Piperidine (5 µL, 0.05 mmol) was added to a suspension of 4-(2,2-dicyanovinyl)benzoic acid (100 mg, 0.5 mmol) and benzyl acetoacetate (87 µL, 0.5 mmol) in EtOH (3 mL). The mixture was stirred at ambient temperature for 6 h. The resulting precipitate was collected and washed with cold EtOH to give a white solid (55 mg). Column chromatography (SiO2, EtOAc) afforded the title compound as beige solid (31 mg, 16%). 1H NMR (400 MHz, MeOD) δ 7.89 (d, J=8.4 Hz, 2H), 7.28-7.16 (m, 5H), 7.02 (dd, J=7.8, 1.7 Hz, 2H), 5.09 (d, J=12.3 Hz, 1H), 4.94 (d, J=12.3 Hz, 1H), 4.45 (d, J=0.9 Hz, 1H), 2.40 (d, J=1.0 Hz, 3H). 13C NMR (100 MHz, MeOD) δ 169.79, 167.03, 160.45, 159.62, 151.19, 137.07, 131.11, 130.73, 129.39, 129.22, 129.13, 128.63, 120.59, 108.00, 67.43, 58.77, 40.46, 18.71. MS (ESI) m/z: 391.4 (M+H)+(60%).

Benzyl 6-amino-5-cyano-4-(4-cyanophenyl)-2-methyl-4H-pyran-3-carboxylate

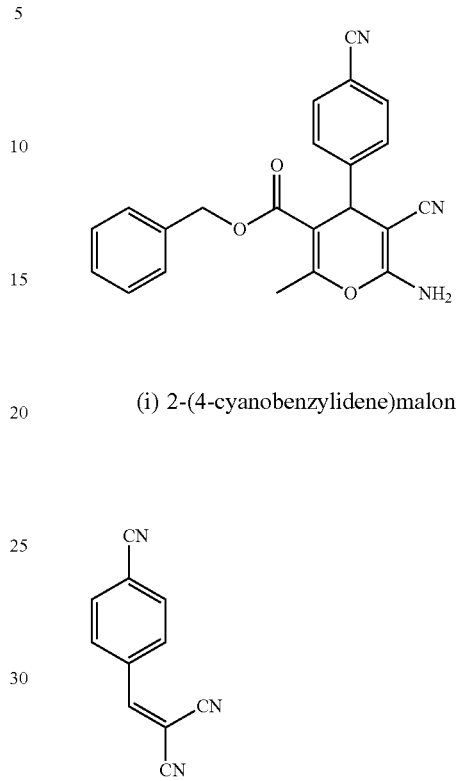

(i) 2-(4-cyanobenzylidene)malononitrile

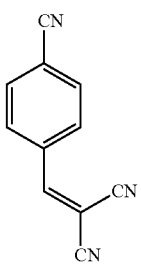 [SMILES: N#CC(C#N)=Cc1ccc(C#N)cc1]

A suspension of malononitrile (111 mg, 1.68 mmol) and 4-cyanobenzaldehyde (200 mg, 1.53 mmol) in H2O (10 mL) was stirred at 100° C. for 8 h. The resulting precipitate was collected and washed with H2O to give the title compound as a cream solid (228 mg, 83%). 1H NMR (400 MHz, MeOD) δ 8.31 (s, 1H), 8.09 (d, J=8.3 Hz, 2H), 7.93 (d, J=8.5 Hz, 2H).

(ii) Benzyl 6-amino-5-cyano-4-(4-cyanophenyl)-2-methyl-4H-pyran-3-carboxylate

Piperidine (3 µL, 0.028 mmol) was added to a suspension of the intermediate 2-(4-cyanobenzylidene)malononitrile (50 mg, 0.28 mmol) and benzyl acetoacetate (48 µL, 0.28 mmol) in EtOH (2 mL). The mixture was stirred at ambient temperature for 1 h. The resulting precipitate was collected and washed with cold EtOH to give the title compound as a white solid (77 mg, 74%). 1H NMR (400 MHz, CDCl$_3$) δ 7.51 (d, J=8.5 Hz, 2H), 7.35-7.26 (m, 3H), 7.21 (d, J=8.3 Hz, 2H), 7.06-7.01 (m, 2H), 5.08 (d, J=12.1 Hz, 1H), 4.93 (d, J=12.1 Hz, 1H), 4.54 (s, 2H), 4.49 (d, J=0.8 Hz, 1H), 2.42 (d, J=1.0 Hz, 3H). 13C NMR (100 MHz, CDCl3) δ 165.23, 158.59, 157.62, 148.97, 135.13, 132.65, 128.67, 128.62, 128.46, 128.43, 118.86, 118.35, 111.18, 106.64, 66.92, 61.27, 39.06, 18.78.

Benzyl 6-amino-5-cyano-4-(3-cyanophenyl)-2-methyl-4H-pyran-3-carboxylate

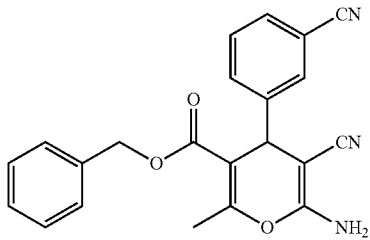 [SMILES: CC1=C(C(=O)OCc2ccccc2)C(c2cccc(C#N)c2)C(C#N)=C(N)O1]

(i) 2-(3-cyanobenzylidene)malononitrile

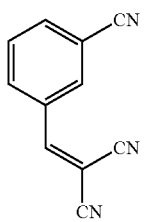

A suspension of malononitrile (111 mg, 1.68 mmol) and 3-formyl benzonitrile (200 mg, 1.53 mmol) in H2O (5 mL) was stirred at 100° C. with microwave heating for 3 min. The resulting precipitate was collected and washed with H$_2$O to give the title compound as a white solid (225 mg, 82%). 1H NMR (400 MHz, CDCl$_3$) δ 8.20 (ddd, J=8.0, 1.2, 0.6 Hz, 1H), 8.08-8.07 (m, 1H), 7.90 (dt, J=7.8, 1.3 Hz, 1H), 7.79 (s, 1H), 7.71 (t, J=7.9 Hz, 1H). MS (ESI) m/z: 178.2 (M–H)– (50%).

(ii) benzyl 6-amino-5-cyano-4-(3-cyanophenyl)-2-methyl-4H-pyran-3-carboxylate

Piperidine (3 μL, 0.028 mmol) was added to a suspension of 2-(3-cyanobenzylidene)malononitrile (50 mg, 0.28 mmol) and benzyl acetoacetate (48 μL, 0.28 mmol) in EtOH (2 mL). The mixture was stirred at ambient temperature for 1 h. The resulting precipitate was collected and washed with cold EtOH to give the title compound as a white solid (82 mg, 79%). 1H NMR (400 MHz, CDCl$_3$) δ 7.49 (dt, J=7.1, 1.6 Hz, 1H), 7.40-7.27 (m, 6H), 7.10-7.05 (m, 2H), 5.06 (d, J=12.1 Hz, 1H), 4.95 (d, J=12.1 Hz, 1H), 4.59 (bs, 2H), 4.46 (d, J=0.9 Hz, 1H), 2.42 (d, J=1.0 Hz, 3H). 13C NMR (100 MHz, CDCl$_3$) δ 165.23, 158.60, 157.70, 145.39, 135.07, 132.36, 131.31, 131.05, 129.55, 128.76, 128.68, 128.49, 118.83, 118.39, 112.84, 106.79, 67.04, 61.36, 38.70, 18.83.

4-(3-Acetyl-6-amino-5-cyano-2-methyl-4H-pyran-4-yl)benzoicacid

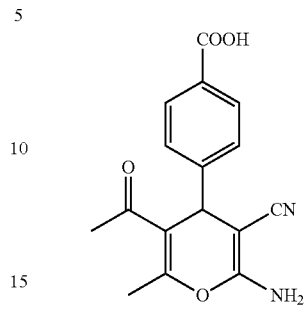

Piperidine (38 μL, 0.38 mmol) was added to a suspension of 4-(2,2-dicyanovinyl)benzoic acid (750 mg, 3.78 mmol) and acetyl acetone (379 mg, 3.78 mmol) in EtOH (5 mL). The mixture was stirred at ambient temperature for 18 h. The resulting precipitate was collected and washed with cold EtOH to give the title compound as a white solid (840 mg, 75%). $^1$H NMR (400 MHz, MeOD) δ 7.99 (d, J=8.4 Hz, 2H), 7.32 (d, J=8.3 Hz, 2H), 4.57 (d, J=0.8 Hz, 1H), 2.33 (d, J=0.9 Hz, 1H), 2.10 (s, 2H). MS (ESI) m/z: 297.3 (M–H)– (40%).

compound 1

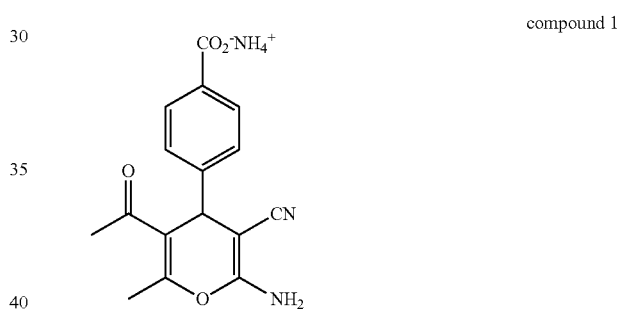

A sample of 4-(3-acetyl-6-amino-5-cyano-2-methyl-4H-pyran-4-yl)benzoic acid was dissolved in an aqueous solution of NH$_4$HCO$_3$ (2 eq.) and lyophilized to give compound 1. $^1$H NMR (400 MHz, D$_2$O) δ 7.90 (d, J=8.4 Hz, 2H), 7.38 (d, J=8.3 Hz, 2H), 4.63 (d, J=0.8 Hz, 1H), 2.32 (d, J=0.9 Hz, 3H), 2.20 (s, 3H).

3-(3-Acetyl-6-amino-5-cyano-2-methyl-4H-pyran-4-yl)benzoic acid

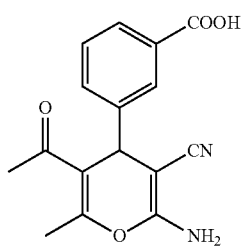 [SMILES: CC(=O)C1=C(C)OC(N)=C(C#N)C1c1cccc(C(=O)O)c1]

Piperidine (2 drops) was added to a solution of malononitrile (48 mg, 0.73 mmol) and 3-carboxybenzaldehyde (100 mg, 0.66 mmol) in acetonitrile (3 mL) and stirred at ambient temperature for 1 h. Acetyl acetone (75 μL, 0.73 mmol) was added and the mixture stirred at ambient temperature for 4 h. The volume of solvent was reduced and the resulting residue purified by column chromatography (SiO$_2$, CHCl$_3$:ACN:AcOH, 9:0.7:0.3). The product was obtained as a beige solid (13 mg, 7%). 1H NMR (400 MHz, MeOD) δ 7.92-7.90 (m, 1H), 7.86 (m, 1H), 7.47-7.44 (m, 2H), 4.57 (d, J=0.9 Hz, 1H), 2.33 (d, J=0.9 Hz, 3H), 2.10 (s, 3H).

5-Acetyl-2-amino-6-methyl-4-(quinolin-2-yl)-4H-pyran-3-carbonitrile

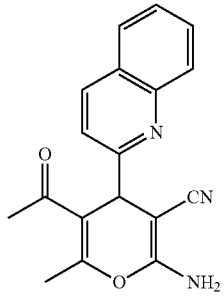 [SMILES: CC(=O)C1=C(C)OC(N)=C(C#N)C1c1ccc2ccccc2n1]

(i)$_2$-(quinolin-2-ylmethylene)malononitrile

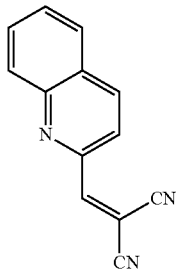 [SMILES: N#CC(C#N)=Cc1ccc2ccccc2n1]

A suspension of malononitrile (92 mg, 1.39 mmol) and 2-quinoline carboxaldehyde (200 mg, 1.27 mmol) in H2O (5 mL) were stirred at ambient temperature for 7 h. The precipitate was collected and washed with H2O to give the title compound as a green solid (240 mg, 92%). 1H NMR (400 MHz, MeOD) δ 8.48 (d, J=8.0 Hz, 1H), 8.37 (s, 1H), 8.16 (d, J=8.6 Hz, 1H), 8.00 (d, J=8.2 Hz, 1H), 7.86 (ddd, J=8.5, 6.9, 1.4 Hz, 1H), 7.80 (d, J=8.4 Hz, 1H), 7.73 (ddd, J=8.1, 6.9, 1.2 Hz, 1H).

(ii) 5-acetyl-2-amino-6-methyl-4-(quinolin-2-yl)-4H-pyran-3-carbonitrile

Piperidine (2.4 μL, 0.024 mmol) was added to a solution of 2-(quinolin-2-ylmethylene)malononitrile (50 mg, 0.24 mmol) and acetyl acetone (25 μL, 0.24 mmol) in EtOH (0.5 mL). The mixture was stirred at ambient temperature for 6 h. The resulting precipitate was collected and washed with cold EtOH to give a pale brown solid (24 mg, 33%). 1H NMR (400 MHz, MeOD) δ 8.33 (d, J=8.5 Hz, 1H), 8.03 (d, J=8.5 Hz, 1H), 7.90 (dd, J=8.2, 1.2 Hz, 1H), 7.76 (ddd, J=8.5, 6.9, 1.5 Hz, 1H), 7.59 (ddd, J=8.1, 6.9, 1.2 Hz, 1H), 7.44 (d, J=8.5 Hz, 1H), 4.83 (d, J=1.0 Hz, 1H), 2.36 (d, J=1.0 Hz, 3H), 2.16 (d, J=3.4 Hz, 3H). MS (ESI) m/z: 306.5 (M+H)+ (100%).

5-Acetyl-2-amino-4-(3-cyanophenyl)-6-methyl-4H-pyran-3-carbonitrile

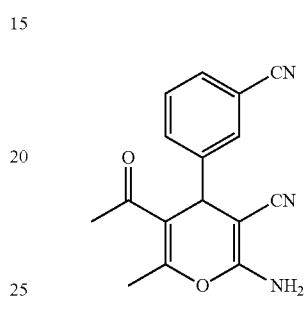

Piperidine (3 μL, 0.028 mmol) was added to a suspension of 2-(3-cyanobenzylidene)malononitrile (50 mg, 0.28 mmol) and acetyl acetone (28 mg, 0.28 mmol) in EtOH (2 mL). The mixture was stirred at ambient temperature for 1 h. The resulting precipitate was collected and washed with cold EtOH to give a white solid (64 mg). Column chromatography (SiO$_2$, EtOAc:Hexane, 1:2 followed by 100% EtOH) afforded the title compound as white solid (36 mg, 46%). 1H NMR (400 MHz, DMSO) δ 7.72 (dt, J=7.3, 1.6 Hz, 1H), 7.64 (s, 1H), 7.57 (t, J=7.5 Hz, 1H), 7.53 (dt, J=7.9, 1.6 Hz, 1H), 6.99 (bs, 2H), 4.57 (s, 1H), 2.27 (d, J=0.7 Hz, 3H), 2.09 (s, 3H). 13C NMR (100 MHz, DMSO) δ 197.93, 158.45, 156.07, 146.31, 132.25, 130.92, 130.61, 130.11, 119.53, 118.72, 114.32, 111.62, 56.88, 38.29, 30.12, 18.77.

5-Acetyl-2-amino-6-methyl-4-(4-(thiophen-2-yl)phenyl)-4H-pyran-3-carbonitrile

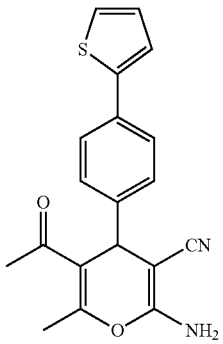 [SMILES: CC(=O)C1=C(C)OC(N)=C(C#N)C1c1ccc(-c2cccs2)cc1]

61

(i) 2-(4-(thiophen-2-yl)benzylidene)malononitrile

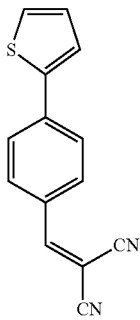 [SMILES: N#CC(C#N)=Cc1ccc(-c2cccs2)cc1]

Piperidine (2.6 µL, 0.027 mmol) was added to a solution of malononitrile (19 mg, 0.29 mmol) and 4-(2-thienyl)benzaldehyde (50 mg, 0.27 mmol) in EtOH (1.5 mL). The mixture was stirred at ambient temperature for 1 h. The resulting precipitate was collected and washed with cold EtOH to give the intermediate as a yellow solid (53 mg, 83%). 1H NMR (400 MHz, CDCl$_3$) δ 7.93 (d, J=8.4 Hz, 2H), 7.76 (d, J=8.5 Hz, 2H), 7.72 (s, 1H), 7.51 (dd, J=3.7, 1.1 Hz, 1H), 7.44 (dd, J=5.1, 1.1 Hz, 1H), 7.15 (dd, J=5.1, 3.7 Hz, 1H).

(ii) 5-acetyl-2-amino-6-methyl-4-(4-(thiophen-2-yl)phenyl)-4H-pyran-3-carbonitrile Piperidine (2.2 µL, 0.022 mmol) was added to a suspension of the intermediate 2-(4-(thiophen-2-yl)benzylidene)malononitrile (53 mg, 0.22 mmol) and acetyl acetone (23 µL, 0.22 mmol) in toluene (1 mL). The mixture was stirred at ambient temperature for 4 h. The resulting precipitate was collected and washed with toluene to give a pale yellow solid. Column chromatography (SiO$_2$, CH$_2$Cl$_2$:Et$_2$O, 95:5) afforded the title compound as a white solid (40 mg, 77%). HRMS (ESI+): Found: m/z 337.1008 (M+H)+, C$_{19}$H$_{17}$N$_2$O$_2$S requires m/z 337.1001. 1 H NMR (400 MHz, CDCl$_3$) δ 7.58 (d, J=8.3 Hz, 2H), 7.30-7.25 (m, 2H), 7.21 (d, J=8.3 Hz, 2H), 7.07 (dd, J=5.1, 3.6 Hz, 1H), 4.46 (s, 1H), 4.43 (bs, 2H), 2.32 (d, J=1.0 Hz, 3H), 2.09 (s, 3H).

5-Acetyl-2-amino-6-methyl-4-(quinoxalin-6-yl)-4H-pyran-3-carbonitrile

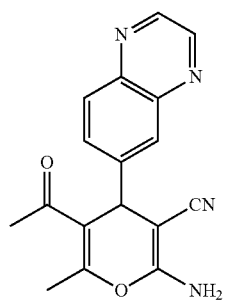 [SMILES: CC(=O)C1=C(C)OC(N)=C(C#N)C1c1ccc2nccnc2c1]

62

(i) 2-(quinoxalin-6-ylmethylene)malononitrile

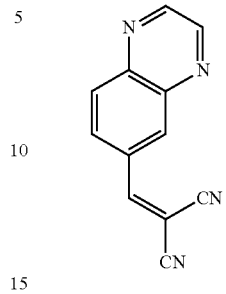

Piperidine (4.7 µL, 0.047 mmol) was added to a solution of malononitrile (34 mg, 0.52 mmol) and quinoxaline-6-carbaldehyde (75 mg, 0.47 mmol) in EtOH (1 mL). The mixture was stirred at ambient temperature for 1 h. The resulting precipitate was collected and washed with cold EtOH to give the intermediate as a light brown solid (66 mg, 68%). 1H NMR (400 MHz, CDCl$_3$) δ 8.97 (s, 2H), 8.55 (d, J=2.1 Hz, 1H), 8.37 (dd, J=8.9, 2.1 Hz, 1H), 8.27 (d, J=8.9 Hz, 1H), 8.01 (s, 1H).

(ii) 5-acetyl-2-amino-6-methyl-4-(quinoxalin-6-yl)-4H-pyran-3-carbonitrile

Piperidine (1.4 µL, 0.015 mmol) was added to a suspension of the intermediate 2-(quinoxalin-6-ylmethylene)malononitrile (30 mg, 0.145 mmol) and acetyl acetone (15 µL, 0.145 mmol) in toluene (1 mL). The mixture was stirred at ambient temperature for 4 h. The resulting precipitate was collected and washed with cold Et$_2$O to give the title compound as a beige solid (38 mg, 86%). HRMS (ESI+): Found: m/z 307.1190 (M+H)+, C$_{17}$H$_{15}$N$_4$O$_2$ requires m/z 307.1195. 1 H NMR (400 MHz, CDCl$_3$) δ 8.86-8.81 (m, 2H), 8.11 (d, J=8.7 Hz, 1H), 7.92 (d, J=2.0 Hz, 1H), 7.69 (dd, J=8.7, 2.1 Hz, 1H), 4.72 (s, 1H), 4.59 (bs, 2H), 2.36 (d, J=0.9 Hz, 3H), 2.13 (s, 3H). 13C NMR (101 MHz, CDCl$_3$) δ 197.92, 157.70, 156.10, 145.54, 145.35, 145.26, 143.25, 142.63, 130.77, 129.91, 127.65, 118.58, 114.92, 61.83, 39.73, 30.17, 19.11.

2-(3-Acetyl-6-amino-5-cyano-2-methyl-4H-pyran-4-yl)benzoicacid

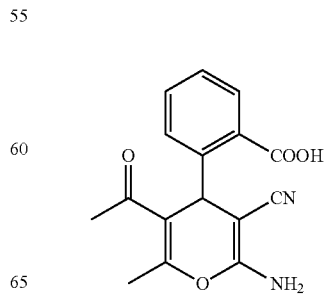

(i) 2-(2,2-dicyanovinyl)benzoic acid

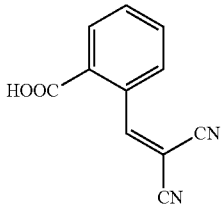 [SMILES: N#CC(C#N)=Cc1ccccc1C(=O)O]

A suspension of malononitrile (48 mg, 0.73 mmol) and 2-carboxybenzaldehyde (100 mg, 0.67 mmol) in H₂O (4 mL) was stirred at 100° C. with microwave heating for 3 min. The resulting precipitate was collected and washed with H₂O to give the title compound as a white solid (34 mg, 55%). 1H NMR (400 MHz, MeOD) δ 8.87 (s, 1H), 8.19 (dd, J=7.6, 1.2 Hz, 1H), 7.83-7.78 (m, 1H), 7.75 (td, J=7.5, 1.4 Hz, 1H), 7.70 (td, J=7.5, 1.3 Hz, 1H).

2-(3-acetyl-6-amino-5-cyano-2-methyl-4H-pyran-4-yl)benzoic acid

Piperidine (12.5 μL, 0.125 mmol) was added to a suspension of 2-(2,2-dicyanovinyl)benzoic acid (50 mg, 0.25 mmol) and acetyl acetone (25 mg, 0.25 mmol) in EtOH (3 mL). The mixture was stirred for 3 d. The solvent was removed in vacuo and the residue taken up in EtOAc and stirred for 18 h. The resulting precipitate was collected and washed with cold EtOAc to give a pale yellow solid (76 mg). Column chromatography (SiO₂, ACN:CHCl3, 2:1, followed by EtOAc:MeCOH, 95:5) gave a yellow residue (33 mg). 1H NMR (400 MHz, MeOD) δ 7.94 (dd, J=7.9, 1.2 Hz, 1H), 7.52 (td, J=7.6, 1.4 Hz, 1H), 7.31 (td, J=7.7, 1.3 Hz, 1H), 7.26 (dd, J=7.9, 1.0 Hz, 1H), 6.02 (d, J=1.0 Hz, 1H), 2.29 (d, J=1.0 Hz, 3H), 2.05 (s, 3H).

4-(2-Acetamido-5-acetyl-3-cyano-6-methyl-4H-pyran-4-yl)benzoic acid

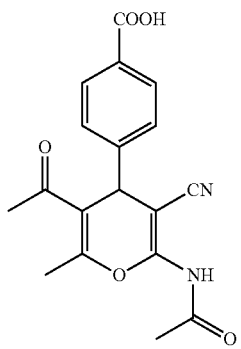 [SMILES: CC(=O)NC1=C(C#N)C(c2ccc(C(=O)O)cc2)C(C(C)=O)=C(C)O1]

A solution of 4-(3-acetyl-6-amino-5-cyano-2-methyl-4H-pyran-4-yl)benzoic acid (250 mg, 0.84 mmol) in acetic anhydride (3 mL) was heated to reflux for 3 h. The mixture was concentrated under a stream of N2 and then poured into ice cold H2O. The aqueous solution was extracted with EtOAc (3×20 mL) and the combined organic extract was washed with brine (20 mL), dried (MgSO₄), filtered and reduced in vacuo to give a yellow oil. The yellow oil was dissolved in EtOH (5 mL) and hydrazine hydrate (1.3 eq.) was added. After stirring for 30 min the suspension was reduced in vacuo and taken up in H₂O (10 mL) and extracted with EtOAc (3×10 mL). The combined organic extract was dried (MgSO₄), filtered and solvent removed in vacuo to give a yellow oil. Column chromatography (SiO₂, EtOAc:MecOH, 95:5 followed by 100% EtOH) afforded the title compound (20 mg, 7%). 1H NMR (400 MHz, MeOD) δ 8.02 (d, J=8.4 Hz, 2H), 7.41 (d, J=8.3 Hz, 2H), 4.80 (s, 1H), 2.34 (d, J=0.8 Hz, 3H), 2.15 (s, 3H), 2.08 (s, 3H). MS (ESI) m/z: 341.4 (M+H)+ (100%).

4-(2-Amino-3,5-bis(ethoxycarbonyl)-6-methyl-4H-pyran-4-yl)benzoicacid

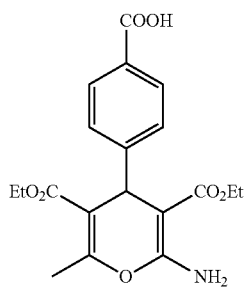 [SMILES: CCOC(=O)C1=C(C)OC(N)=C(C(=O)OCC)C1c1ccc(C(=O)O)cc1]

(i)(Z)-4-(2-cyano-3-ethoxy-3-oxoprop-1-enyl)benzoicacid

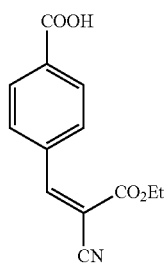

Piperidine (13 μL, 0.13 mmol) was added to a suspension of ethyl cyanoacetate (151 mg, 1.33 mmol) and 4-carboxybenzaldehyde (200 mg, 1.33 mmol) in EtOH (3 mL). The mixture was heated to reflux for 3 h. The mixture was concentrated in vacuo. Toluene was added and the resulting precipitate was collected and washed with toluene to give the intermediate as a white solid (278 mg, 85%). 1H NMR (400 MHz, MeOD) δ 8.40 (s, 1H), 8.16 (d, J=8.6 Hz, 2H), 8.10 (d, J=8.4 Hz, 2H), 4.39 (q, J=7.1 Hz, 2H), 1.39 (t, J=7.1 Hz, 3H).

(ii) 4-(2-amino-3,5-bis(ethoxycarbonyl)-6-methyl-4H-pyran-4-yl)benzoic acid

Piperidine (20 μL, 0.2 mmol) was added to a suspension of (Z)-4-(2-cyano-3-ethoxy-3-oxoprop-1-enyl)benzoic acid (50 mg, 0.2 mmol) and ethyl acetoacetate (26 mg, 0.2 mmol) in EtOH (3 mL). The mixture was stirred at ambient temperature for 2 d. Piperidine (10 μL, 0.1 mmol) was added and solution stirred for a further 1 d. The mixture was concentrated in vacuo and the residue purified by column chromatography (SiO$_2$, EtOAc:Hexane, 2:1) to give a yellow oil. Recystallisation from EtOH gave a white solid (>5 mg). 1H NMR (400 MHz, MeOD) δ 7.88 (d, J=8.4 Hz, 2H), 7.29 (d, J=8.3 Hz, 2H), 4.73 (d, J=0.7 Hz, 1H), 4.12-3.98 (m, 4H), 2.37 (d, J=0.8 Hz, 3H), 1.18 (t, J=7.1 Hz, 3H), 1.14 (t, J=7.1 Hz, 3H).MS (ESI) m/z: 372.1 (M+H)+ (100%).

(v)$_4$-(3-Acetyl-6-amino-5-(ethoxycarbonyl)-2-methyl-4H-pyran-4-yl)benzoicacid

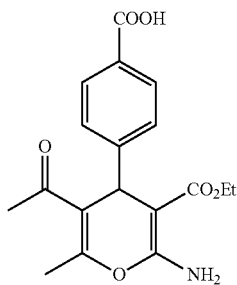 [SMILES: CCOC(=O)C1=C(N)OC(C)=C(C(C)=O)C1c1ccc(C(=O)O)cc1]

Piperidine (30 μL, 0.3 mmol) was added to a suspension of (Z)-4-(2-cyano-3-ethoxy-3-oxoprop-1-enyl)benzoic acid (50 mg, 0.2 mmol) and acetyl acetone (20 mg, 0.2 mmol) in EtOH (3 mL). The mixture was stirred at ambient temperature for 24 h. Analytical HPLC shows a 1:1 ratio of starting material to product however further reaction time leads to decomposition. Purification by column chromatography (SiO$_2$, EtOAc) afforded the title compound (2 mg, 3%). 1H NMR (400 MHz, MeOD) δ 7.90 (d, J=8.4 Hz, 2H), 7.31 (d, J=8.3 Hz, 2H), 4.79 (s, 1H), 4.13-4.02 (m, 2H), 2.32 (d, J=0.7 Hz, 3H), 2.18 (s, 3H), 1.20 (t, J=7.1 Hz, 3H).

IRAP Enzymatic Assay

Crude membranes are prepared from HEK 293T cells transfected with full length human IRAP or empty vector, then solubilized in buffer consisting of 50 mM Tris-HCl, 1% Triton X-100, pH 7.4 at 4° C. under agitation over 5 h. After solubilization, the membranes are pelleted by centrifugation at 23,100 g for 15 min at 4° C., and the supernatant is reserved as the source of IRAP activity. The enzymatic activities of IRAP are determined by the hydrolysis of the synthetic substrate Leu-MCA (Sigma-Aldrich, Missouri, USA) monitored by the release of a fluorogenic product, MCA, at excitation and emission wavelengths of 380 and 440 nm, respectively. Assays are performed in 96-well plates; each well contains between 0.2-10 μg solubilized membrane protein, a range of concentration of substrate in a final volume of 100 μL 50 mM Tris-HCl buffer (pH 7.4). Non-specific hydrolysis of the substrate is corrected by subtracting the emission from incubations with membranes transfected with empty vector. Reactions proceed at 37° C. for 30 min and IRAP inhibitory activity determined in 96-well microtiter plates with absorbance monitored on a Wallac Victor 3 spectrophotometer. The kinetic parameters ($K_m$ and V) are determined by non-linear fitting of the Michaelis-Menten equation (GraphPad Prism, GraphPad Software Inc., CA, USA); final concentrations of Leu-MCA of 15.6 μM-1 mM. Inhibitor constants (Kj) for the competitive inhibitors are calculated from the relationship $IC_{50}=K$; (1+[S]/$K_m$), where IC$_{50}$ values are determined over a range of inhibitor concentrations (10$^{-9}$ to 10$^{-4}$ M). $K_m$ values of IRAP for Leu-MCA are determined from the kinetic studies. Binding affinities of the compounds to IRAP were examined by monitoring the inhibition of the hydrolysis of Leu-MCA in the presence of increasing concentrations of the compounds (10$^{-8}$ to 10$^{-3}$ M).

In order to see whether the inhibitors such as small molecules or antibodies are selective or specific for IRAP, the inhibitory activities of inhibitors for other zinc-dependent metallopeptidases can be determined in 96-well microtiter plates with absorbance monitored on a Wallac Victor 3 spectrophotometer. Such assays are described in WO2009/065169 and include glucose-6-phosphate dehydrogenase and hexokinase activity, leukotriene A4 hydrolase assay, aminopeptidase N assay and angiotensin converting enzyme assay.

Collectively, the studies in the Examples below show that removal or inhibition of IRAP activity has dramatic effects on cardiac and vascular tissue fibrosis and have identified IRAP as a novel target in CVD.

Example 1

Studies were performed to examine the IRAP-specific effects in the heart and vasculature of the Angiotensin II-induced mouse model of fibrosis as initial proof-of-principle studies. In the genetic deletion model, male young adult WT and IRAP KO mice, aged between 4-6 months were treated with either Ang II or saline subcutaneously for a period of 4 weeks via osmotic mini pump. Blood pressure was taken fortnightly. In the pharmacological inhibition model, WT mice were treated co-treated subcutaneously with the synthetic IRAP inhibitor, HFI-419, along with Ang II-infusion for 4 weeks. The inhibitor was dissolved in Dimethyl sulfoxide (DMSO) and 2-hydroxypropyl-pi-cyclodextrin (HBC) at a ratio of 1:3.

Ang II infusion was used as a conventional model to 'stress' the cardiovascular system as this endogenous hormone contributes to the development and progression of a range of cardiovascular diseases including hypertension, heart failure, renal failure and vascular stiffening which are well known risk factors for all of the previous cardiovascular diseases mentioned herein. An advantage of this model, over a naturally ageing model, is that there is a rapid development of organ fibrosis such that the biochemical and clinical features already noted herein are manifested at a quicker rate. Such rapid changes, particularly in organ fibrosis and hypertension, facilitate the testing of genotype and pharmacological inhibition over a 4-week period that also serves the purpose to confirm the universality of our findings in different preclinical models. Thus, the Ang II infusion model leads to exacerbation of organ fibrosis and dysfunction at a faster rate than seen with ageing, and is a well-recognised model of hypertension with multiple cardiovascular pathologies.

Figure 1:
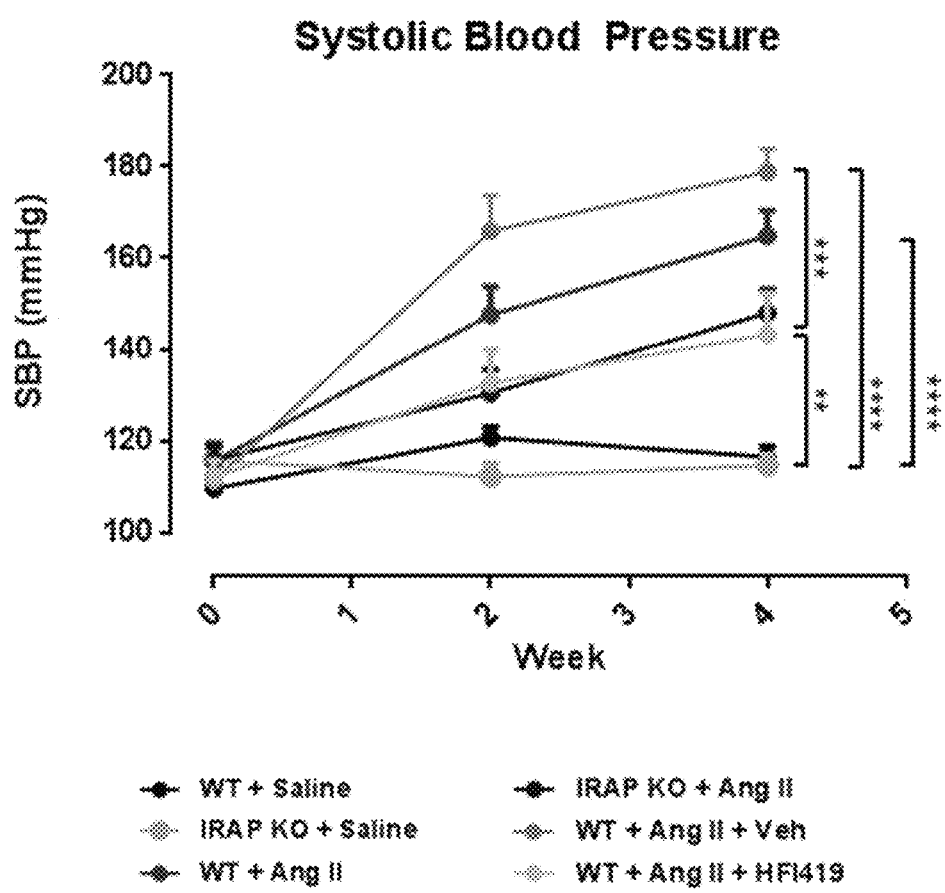
FIG. 1: IRAP deficiency and IRAP inhibition attenuate Angiotensin II-induced increase in systolic blood pressure (SBP). Mean data of systolic blood pressure of adult WT and IRAP$^{-/-}$ mice treated with saline or Ang II (800 ng/kg/min) ±vehicle/HFI 419 (n=6-9). Data expressed as mean s.e.m; P<0.01, *P<0.001, ****P<0.0001 determined by two way repeated measures analysis of variance (ANOVA).

Effect of IRAP Deficiency or IRAP Inhibitor Treatment on Blood Pressure Following Angiotensin II-Infusion IRAP deficiency or chronic IRAP inhibitor treatment with HF1419 attenuates Ang II-induced increase in blood pressure (FIG. 1). Data expressed as mean±s.e.m; P values determined by two way repeated measures analysis of variance (ANOVA).

IRAP Expression in Aorta and Heart of Angiotensin II-Infused Mice

IRAP expression is increased in aortae (FIG. 2$a$) and hearts (FIG. 2$b$) of Ang II-infused WT mice. This is shown by quantification of IRAP expression in medial and adventitial regions of 5 μm thick transverse aortic sections from adult (4-6 month old) WT and IRAP$^{-/-}$ mice treated with Ang II±vehicle/HFI-419 (n=5). Further, the data in FIG. 2$b$ was derived from quantification of IRAP in 5 µm thick transverse heart sections from adult (4-6 month old) WT and IRAP$^{-/-}$ mice treated with Ang II±vehicle/HFI-419 (n=5). Quantification of IRAP expressed as percent positive stained tissue area. Data expressed as mean±s.e.m; P values determined by two way analysis of variance (ANOVA).

Genetic Deletion and Pharmacological Inhibition of IRAP Attenuates Angiotensin II-Mediated Aortic Fibrosis and Associated Markers.

Figure 3:
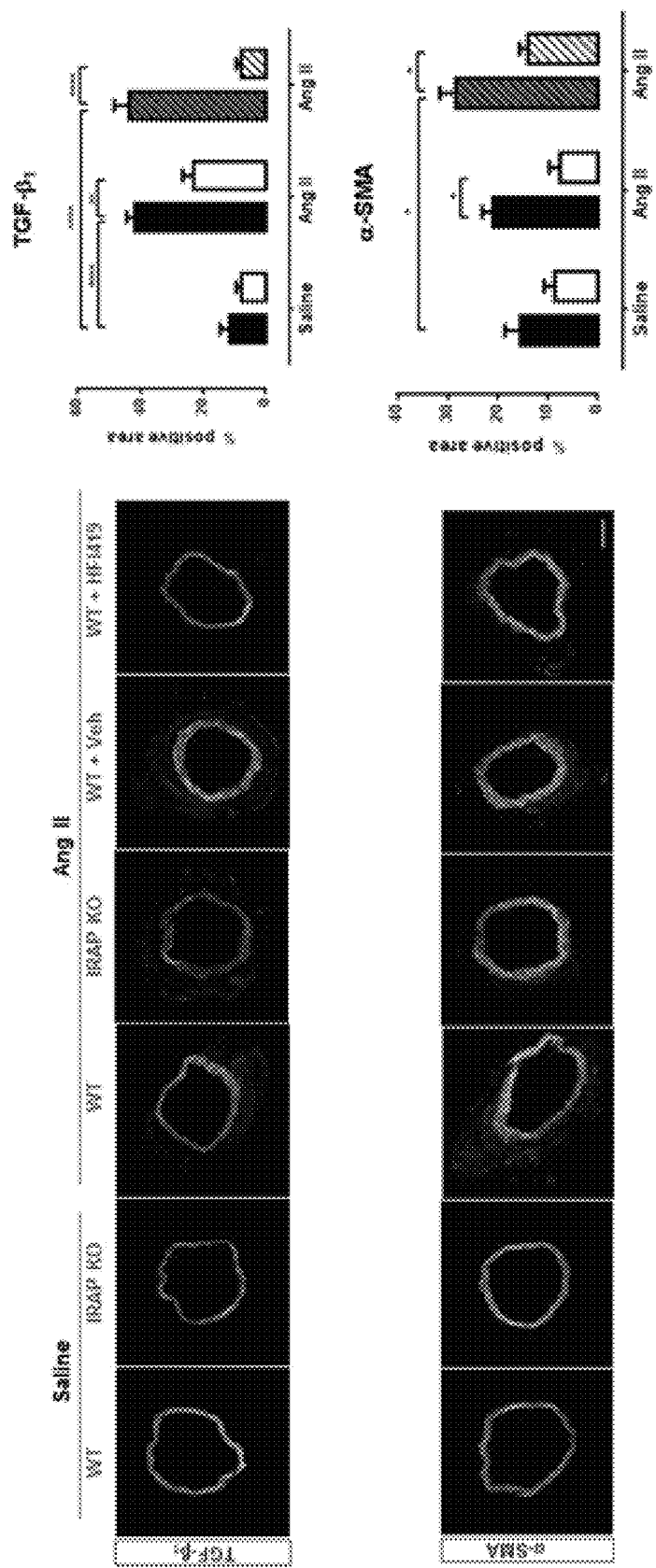
FIG. 3: Genetic deletion and pharmacological inhibition of IRAP attenuates Angiotensin II-mediated aortic fibrosis and associated markers. Representative images and quantification of positive stained immunofluorescence in thoracic aortic sections from adult (4-6 month old) WT and IRAP$^{-/-}$ mice treated with saline or Ang II±vehicle/HFI-419 showing decreased TGF-β$_1$ and α-SMA expression in red with green showing autofluorescence of elastic lamina. Collagen staining was determined using picrosirius red stain and then imaged using polarised microscopy. Data expressed as mean±s.e.m of percentage positive stained area (n=5-6). *P<0.05; P<0.01; *P<0.001, ****P<0.0001 determined by one way ANOVA with Bonferroni correction for multiple comparisons.
Figure 3:
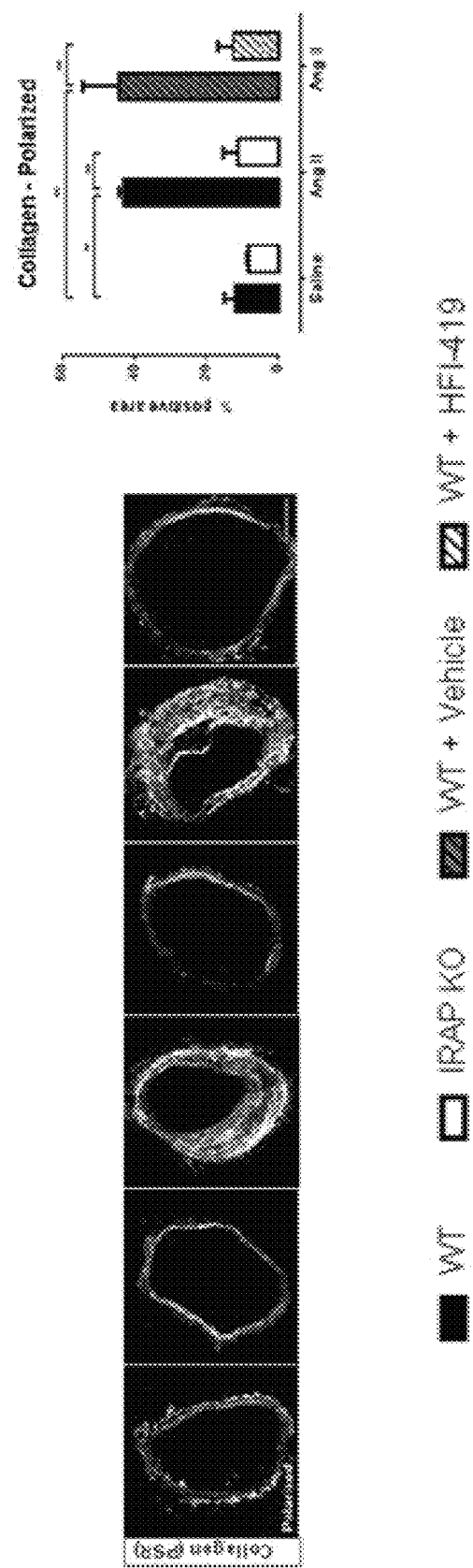

Representative images and quantification of positive stained immunofluorescence in thoracic aortic sections from adult (4-6 month old) WT and IRAP$^{-/-}$ mice treated with saline or Ang II±vehicle/HFI-419 demonstrated decreased TGF-$\beta_1$ and α-SMA expression in red with green showing autofluorescence of elastic lamina (FIG. 3). Collagen staining was determined using picrosirius red and then imaged using polarised microscopy. Data expressed as mean±s.e.m of percentage positive stained area (n=5-6). *P<0.05; P<0.01; *P<0.001, ****P<0.0001 determined by one way ANOVA with Bonferroni correction for multiple comparisons. These findings indicate that Ang II-induced vascular fibrosis and elevated profibrotic markers and that these increases were prevented in IRAP$^{-/-}$ mice or by HFI-419 treatment.

Genetic Deletion and Pharmacological Inhibition of IRAP Attenuates Angiotensin II-Mediated Inflammation in the Aorta.

Figure 4:
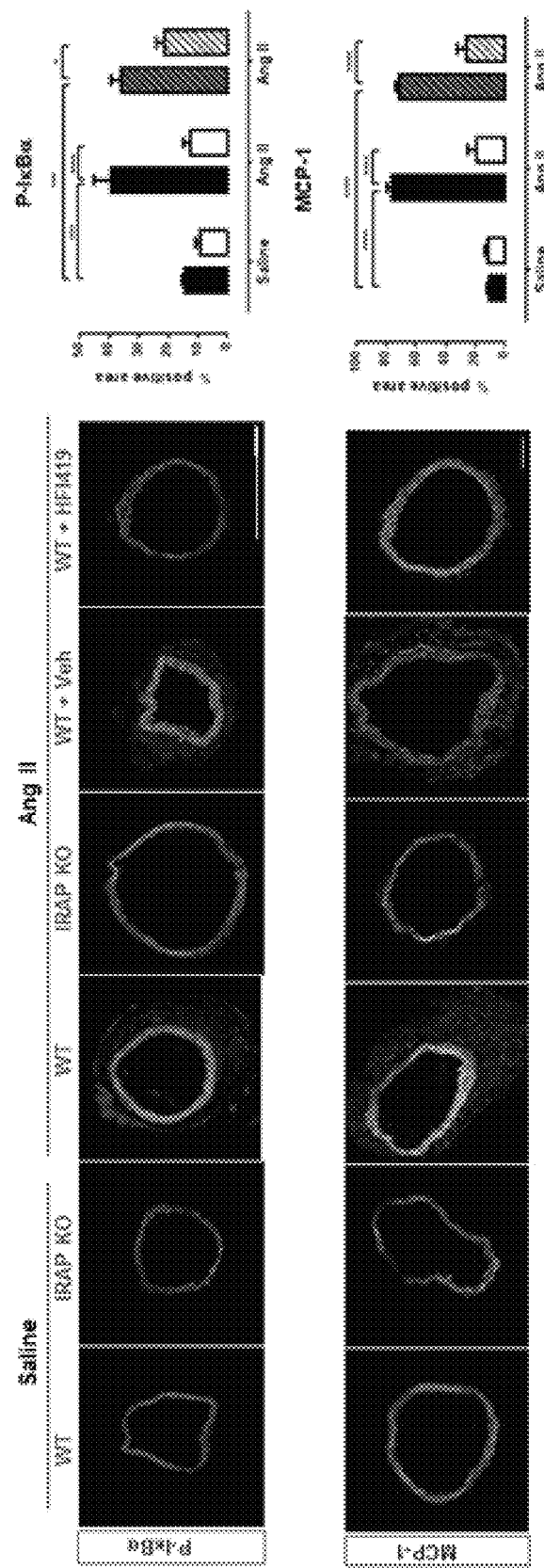
FIG. 4: Genetic deletion and pharmacological inhibition of IRAP attenuates Angiotensin II-mediated inflammation in the aorta. Representative images and quantification of positive stained immunofluorescence in thoracic aortic sections from adult (4-6 month old) WT and IRAP$^{-/-}$ mice treated with saline or Ang II±vehicle/HFI-419 showing P-IκBα (marker for NFκB activation), MCP-1, ICAM-1 and VCAM-1 (vascular cell adhesion protein-1) expression in red with green showing autofluorescence of elastic lamina. Data expressed as mean±s.e.m of percentage positive stained area (n=5-6). *P<0.05; P<0.01; *P<0.001, ****P<0.0001 determined by one way ANOVA with Bonferroni correction for multiple comparisons.
Figure 4:
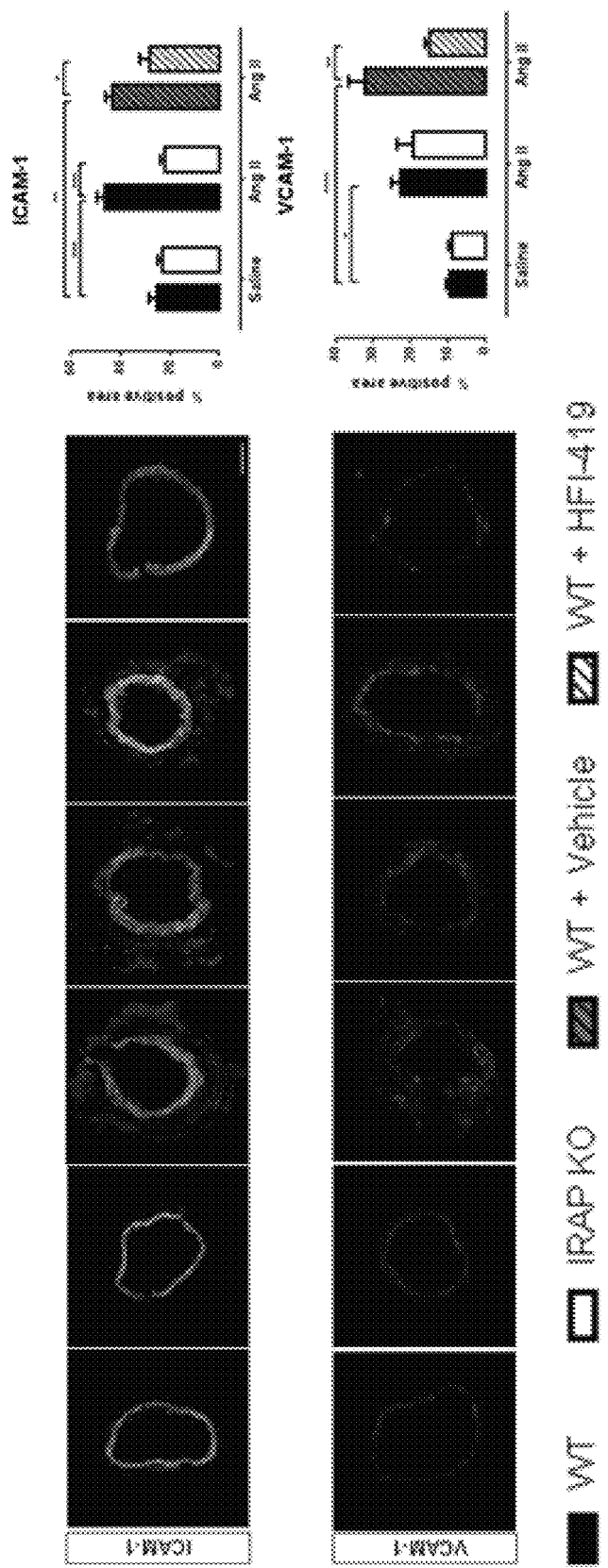

Representative images and quantification of positive stained immunofluorescence in thoracic aortic sections from adult (4-6 month old) WT and IRAP$^{-/-}$ mice treated with saline or Ang II±vehicle/HFI-419 showing reductions in P-IκBα (marker for NFκB activation), MCP-1, ICAM-1 and VCAM-1 (vascular cell adhesion protein-1) expression in red with green showing autofluorescence of elastic lamina (FIG. 4). Data expressed as mean±s.e.m of percentage positive stained area (n=5-6). *P<0.05; P<0.01; *P<0.001, ****P<0.0001 determined by one way ANOVA with Bonferroni correction for multiple comparisons.

Genetic Deletion and Pharmacological Inhibition of IRAP Attenuates Angiotensin II-Mediated Cardiac Hypertrophy and Fibrosis.

Figure 5:
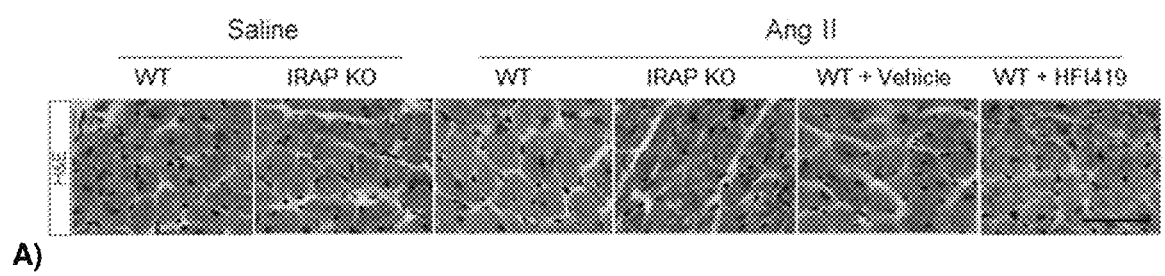
FIG. 5: Genetic deletion and pharmacological inhibition of IRAP attenuates Angiotensin II-mediated cardiac hypertrophy and fibrosis. (a) IRAP deficiency or IRAP inhibition prevented Ang II-mediated increase in cardiac hypertrophy as assessed using cardiomyocyte cross-sectional area in Haematoxylin & Eosin (H&E) stained transverse heart sections (n=6). (b) IRAP deficiency or inhibition significantly decreased interstitial collagen expression determined via brightfield microscopy of picrosirius red stained transverse heart sections (n=6). Data expressed as mean±s.e.m of percentage positive stained area (n=5-6). *P<0.05; P<0.01; *P<0.001, ****P<0.0001 determined by one way ANOVA with Bonferroni correction for multiple comparisons.
Figure 5:
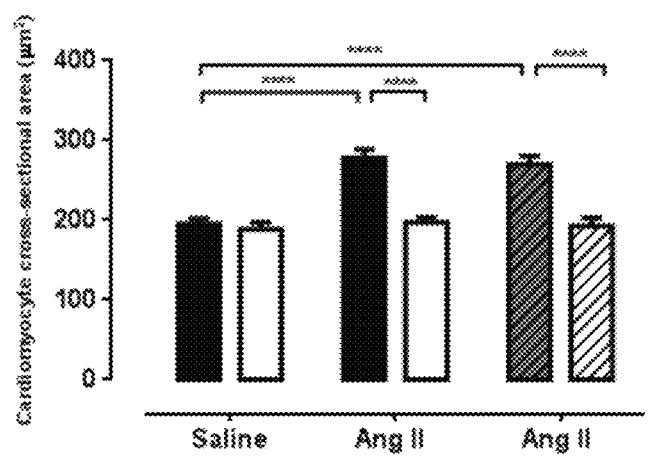
Figure 5:
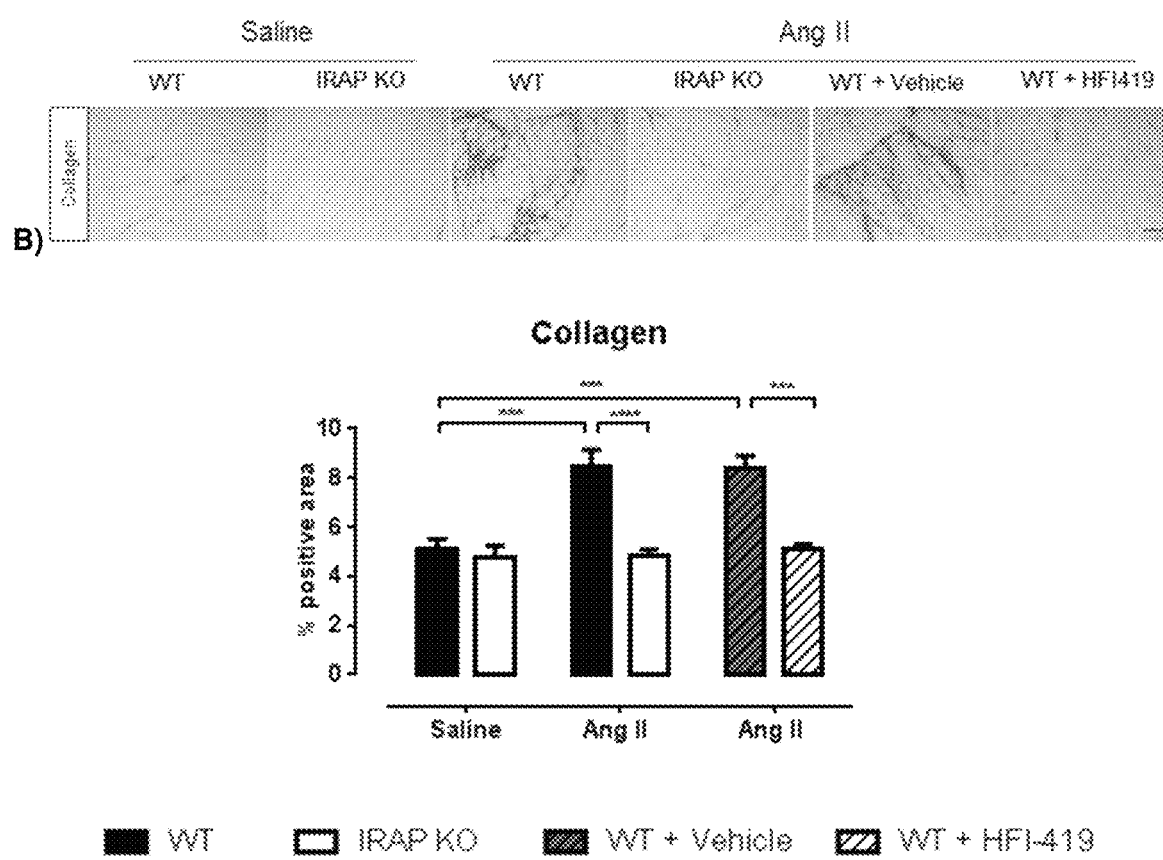

IRAP deficiency or IRAP inhibition (using HFI-419) prevented Ang II-mediated increase in cardiac hypertrophy as assessed using cardiomyocyte cross-sectional area in Haematoxylin & Eosin (H&E) stained transverse heart sections (n=6) as shown in FIG. 5a. IRAP deficiency or inhibition significantly decreased interstitial collagen expression determined via brightfield microscopy of picrosirius red stained transverse heart sections (n=6) as shown in FIG. 5b. Data expressed as mean±s.e.m of percentage positive stained area (n=5-6). *P<0.05; P<0.01; *P<0.001, ****P<0.0001 determined by one way ANOVA with Bonferroni correction for multiple comparisons.

Genetic Deletion and Pharmacological Inhibition of IRAP Prevents Angiotensin II-Induced Increase in Cardiac Fibrogenic Markers.

Figure 6:
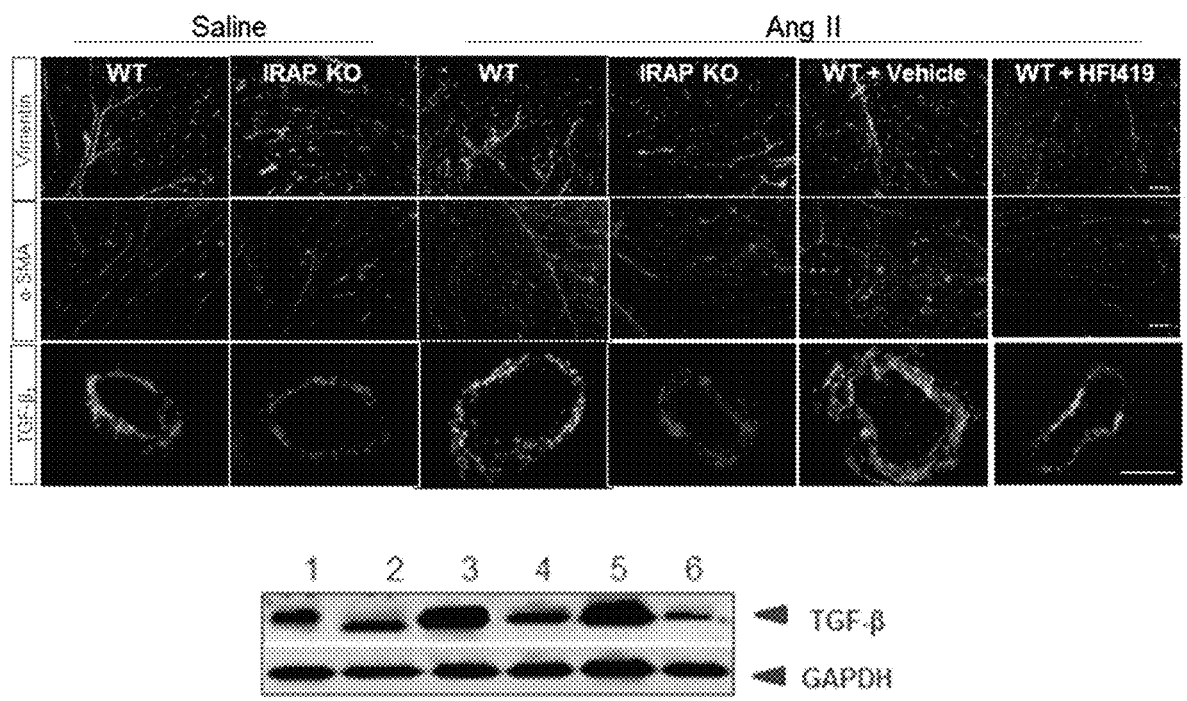
FIG. 6: Genetic deletion and pharmacological inhibition of IRAP prevents Angiotensin II-induced increase in cardiac fibrogenic markers. Representative images and quantification of positive stained immunofluorescence in transverse heart sections from adult (4-6 month old) WT and IRAP$^{-/-}$ mice treated with saline or Ang II±vehicle/HFI-419 showing no change in vimentin staining (marker for fibroblast expression), decreased α-SMA expression (marker for myofibroblast expression) and decreased perivascular expression of TGF-β$_1$ (fibrogenic cytokine) as well as decreased protein expression of TGF-β$_1$. Data expressed as mean±s.e.m of percentage positive stained area for immunofluorescence and densitometric analysis of western blots expressed as relative ratio to mean of WT control±s.e.m; (n=5-6). *P<0.05; P<0.01; *P<0.001, ****P<0.0001 determined by one way ANOVA with Bonferroni correction for multiple comparisons.
Figure 6:
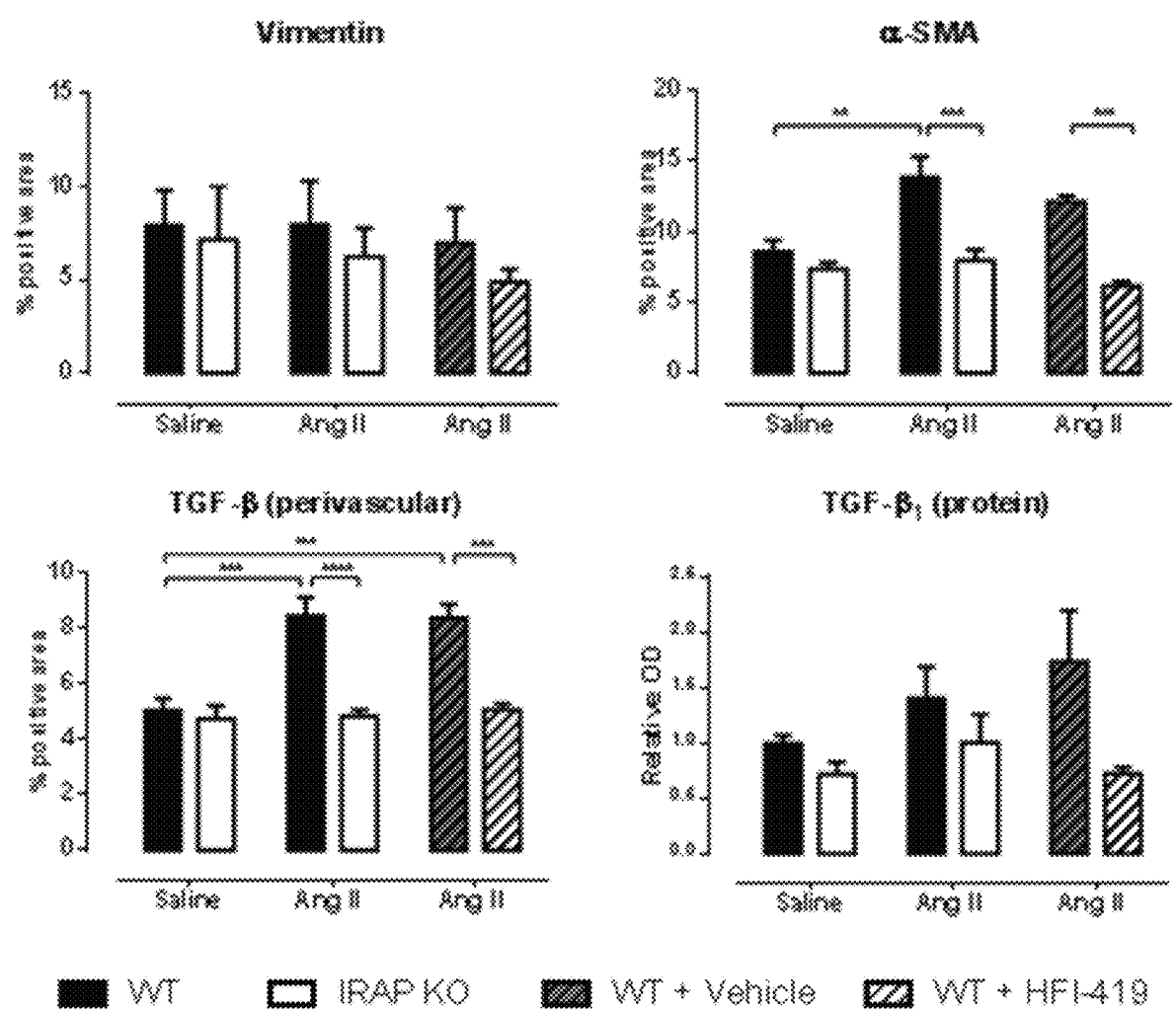

FIG. 6 shows representative images and quantification of positive stained immunofluorescence in transverse heart sections from adult (4-6 month old) WT and IRAP$^{-/-}$ mice treated with saline or Ang II±vehicle/HFI-419 showing no change in vimentin staining (marker for fibroblast expression), decreased α-SMA staining (marker for myofibroblast expression) and decreased perivascular expression of TGF-$\beta_1$ (fibrogenic cytokine) as well as decreased protein expression of TGF-$\beta_1$ (analysed via western blot). Data expressed as mean±s.e.m of percentage positive stained area for immunofluorescence and densitometric analysis of western blots expressed as relative ratio to mean of WT control±s.e.m; (n=5-6). *P<0.05; P<0.01; *P<0.001, ****P<0.0001 determined by one way ANOVA with Bonferroni correction for multiple comparisons.

Genetic Deletion or Pharmacological Inhibition of IRAP Prevents Angiotensin II-Induced Increase in Cardiac Reactive Oxygen Species (ROS) and Inflammatory Markers.

Figure 7:
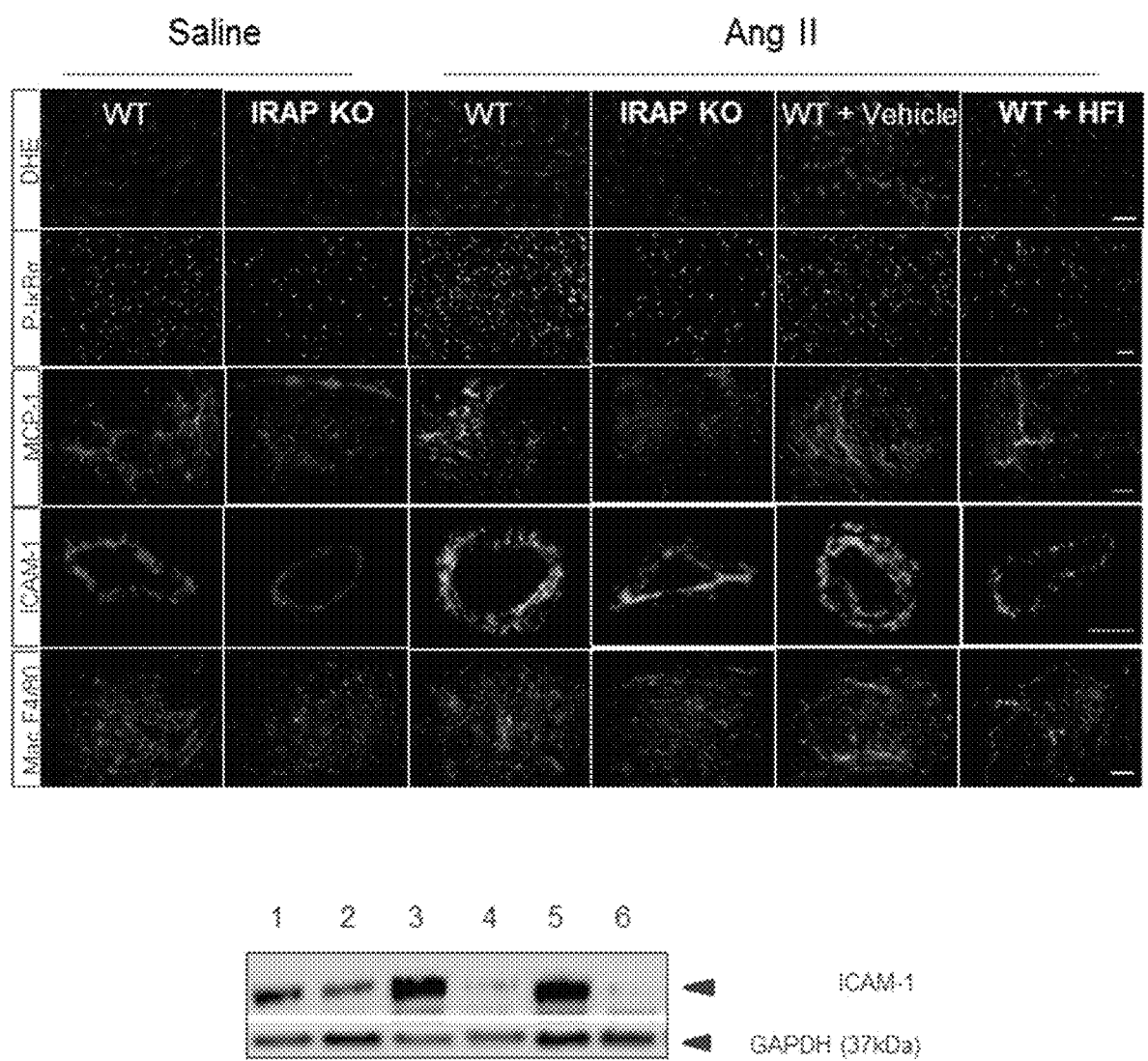
FIG. 7: Genetic deletion or pharmacological inhibition of IRAP prevents Angiotensin II-induced increase in cardiac reactive oxygen species (ROS), assessed by DHE staining, and inflammatory markers. Representative images and quantification of positive stained immunofluorescence in transverse heart sections or quantification of protein levels using western blot analysis from adult (4-6 month old) WT and IRAP$^{-/-}$ mice treated with saline or Ang II±vehicle/HFI-419 (n=5-6). IRAP deficiency or IRAP inhibition prevented Ang II-induced increase in superoxide generation, had no effect on expression of NOX-2 (NADPH isoform), decreased P-IκBα expression (marker for NFκB activation), decreased both ICAM-1 perivascular expression and total protein content as well as decreasing MCP-1 and macrophage (F4/80) expression. Data expressed as mean±s.e.m of percentage positive stained area for immunofluorescence and densitometric analysis of western blots expressed as relative ratio to mean of WT control±s.e.m; (n=5-6). *P<0.05; P<0.01; *P<0.001, ****P<0.0001 determined by one way ANOVA with Bonferroni correction for multiple comparisons.
Figure 7:
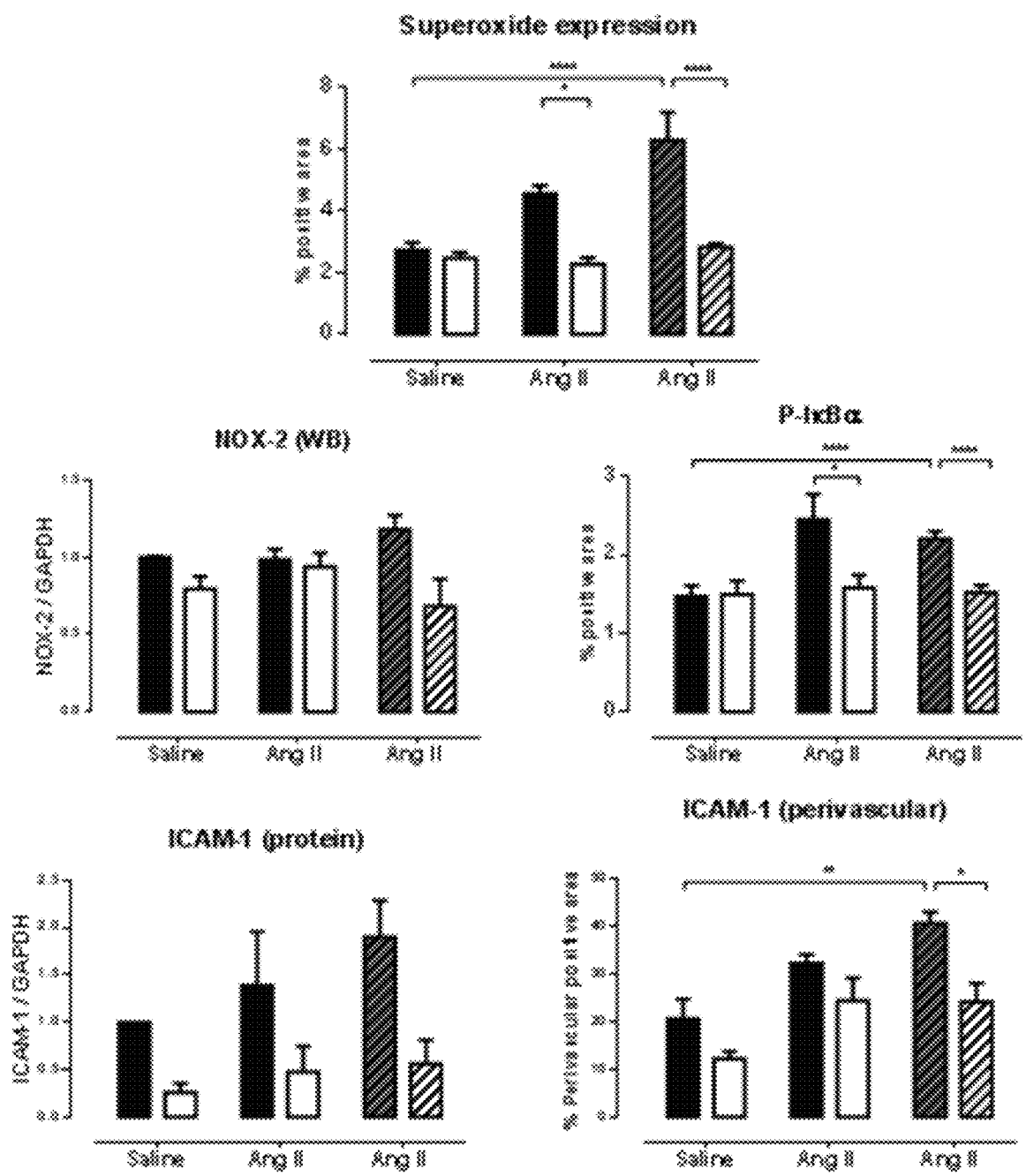
Figure 7:
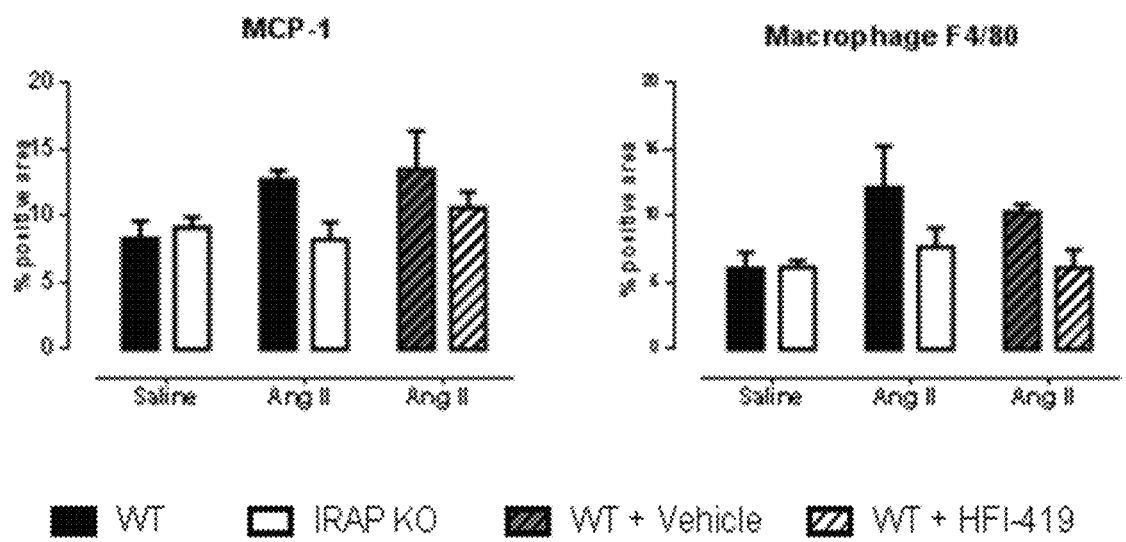

FIG. 7 shows representative images and quantification of positive stained immunofluorescence in transverse heart sections or quantification of protein levels using western blot analysis from adult (4-6 month old) WT and IRAP$^{-/-}$ mice treated with saline or Ang II±vehicle/HFI-419 (n=5-6). IRAP deficiency or IRAP inhibition prevented Ang II-induced increase in superoxide generation, had no effect on expression of the NADPH oxidase isoform, NOX-2, decreased P-IκBα expression (marker for NFκB activation), decreased both ICAM-1 expression and protein content as well as decreasing MCP-1 and macrophage expression. Data expressed as mean±s.e.m of percentage positive stained area for immunofluorescence and densitometric analysis of western blots expressed as relative ratio to mean of WT control±s.e.m; (n=5-6). *P<0.05; P<0.01; *P<0.001, ****P<0.0001 determined by one way ANOVA with Bonferroni correction for multiple comparisons.

Example 2

Following on from the proof-of-principle studies (Example 1) showing that IRAP deficiency and direct pharmacological inhibition of IRAP were effective in preventing Angiotensin II-mediated cardiac and vascular fibrosis and inflammation, this example now underlines the potential clinical effectiveness of targeting IRAP. This is demonstrated using an aged model of cardiovascular fibrosis in which global IRAP deficient mice are protected against age-induced increases in cardiac fibrosis and inflammation whilst direct IRAP inhibition completely reverses age-induced cardiac remodeling.

Global IRAP Gene Deletion Protects Against Age-Induced Cardiac Fibrosis

Figure 8:
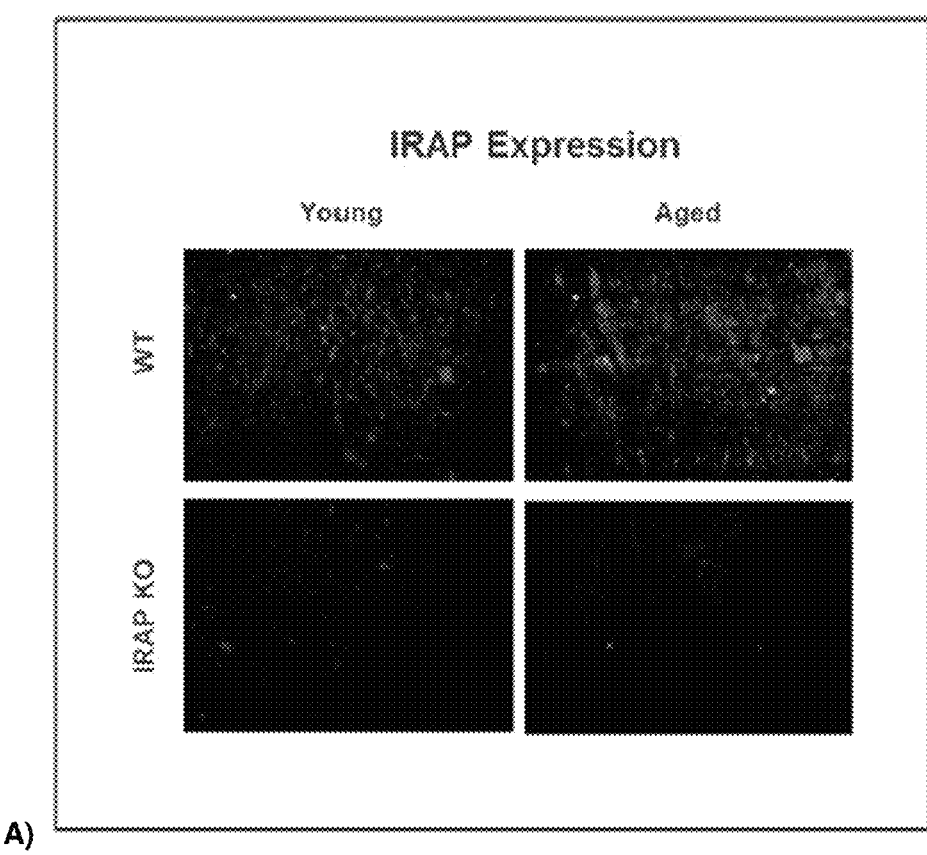
FIG. 8: IRAP expression is increased in aged hearts of ~20 month old wild-type (WT) mice and decreased after IRAP inhibitor treatment. (a) Representative images of IRAP expression (green) in transverse heart sections; (b)
Figure 8:
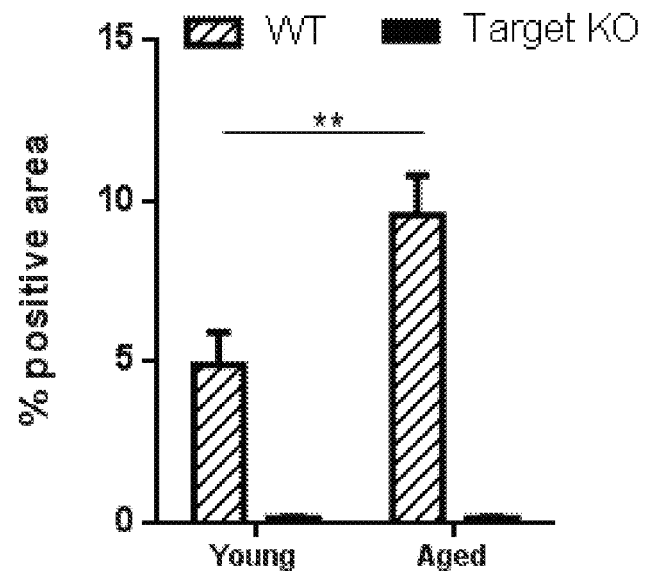
Figure 8:
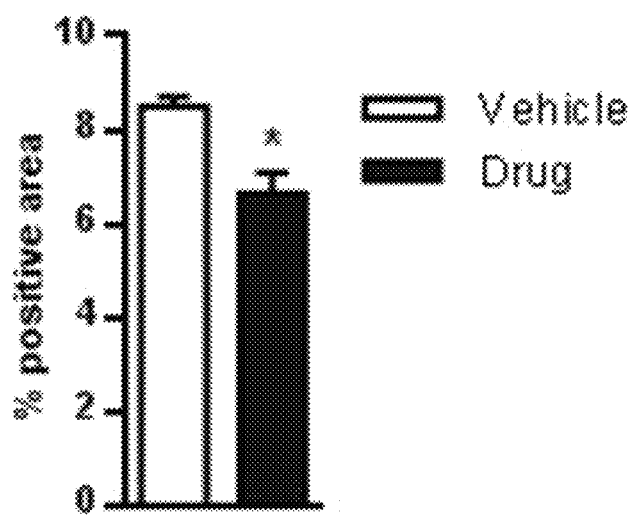

In the current study, IRAP immunofluorescence was present in both interstitial and perivascular regions of the heart and was doubled in the hearts of aged WT mice when compared to their young genotype controls (FIG. 8a,b). The veracity of this effect was confirmed by the absence of staining in hearts obtained from young adult and aged IRAP$^{-/-}$ mice (FIG. 8a). Moreover, IRAP expression was co-localized with α-smooth muscle actin (α-SMA) expression in both interstitial and perivascular regions, suggestive of it being located on VSMC as well as differentiated myofibroblasts. Cardiac fibrosis, assessed by collagen content using picrosirius red staining and quantified using both bright field and circularized polarized light microscopy, was evaluated in young and aged WT mice as well as in young and aged IRAP$^{-/-}$ mice. As expected, aging significantly increased cardiac interstitial fibrosis, by ~75% (FIG. 9a,b; FIG. 10a,b), and also increased perivascular fibrosis, in line with known elevations in ECM in aging hearts (FIG. 10c,d). Such findings highlight the importance of using animal models that follow a natural evolution of CVD. In contrast to the increase in collagen seen in hearts from our aged WT mice, aged IRAP$^{-/-}$ mice exhibited ECM deposition similar to that seen in young adult WT mice (FIG. 9a,b; FIG. 10a-d) indicative of an antifibrotic effect in the absence of IRAP, which was confirmed by a decrease in mature form of collagen α1 Type I protein level (FIG. 11).

The fibrogenic cytokine TGF-β1 is well known to promote the differentiation of fibroblast to a more synthetic type of myofibroblast. In this context, IRAP$^{-/-}$ mice exhibited significantly lower TGF-1 protein in the heart, by Western blot (FIG. 11), and more strikingly, 4-fold less perivascular expression of TGF-β1, by immunofluorescence, as compared to aged WT mice (FIG. 12a,b). While aging did not affect the degree of vimentin-positive fibroblast expression between WT and IRAP genotypes, there was increased myofibroblast expression (αSMA-positive) in hearts from aged WT mice (FIG. 12a,b). In contrast, hearts from aged IRAP$^{-/-}$ mice did not exhibit this age-dependent myofibroblast upregulation, resulting in myofibroblast expression similar to that found in hearts from young WT mice (FIG. 12a,b). These results suggest that exaggerated collagen production due to increased synthetic myofibroblast activity contributed to the increased cardiac fibrosis noted in aged WT hearts, and that this phenomenon was severely blunted in hearts from aged IRAP$^{-/-}$ mice. Consistent with this notion, using double labeling IHC, it was revealed that IRAP was co-localized with myofibroblasts, further implicating a potential role of IRAP in altering myofibroblast functional activity.

Homeostasis of ECM is maintained by the balance between collagen synthesis and collagen degradation. In the current study similar protein levels or enzymatic activity of gelatinases MMP-2 and MMP-9, and of collagenase MMP-8 in aged WT and IRAP$^{-/-}$ mice was demonstrated by Western blot and zymography, (FIG. 11) whereas there was an ~50% increase in MMP-13 protein expression in aged IRAP$^{-/-}$ mice compared to age-matched WT controls (FIG. 11c). MMP-13 is the main collagenase present in the heart thus the increased protein expression indicates greater collagen degradation in aged IRAP deficient mice. Collectively, these results indicate that IRAP deficiency is protective against age-mediated cardiac fibrosis by down-regulating collagen synthesis and up-regulating collagen degradation.

IRAP Deficiency Decreases Superoxide Production and Regulates Inflammation

Dihydroethidium (DHE) staining in the heart revealed ~40% less cardiac superoxide ($\cdot O_2^-$) production in aged IRAP$^{-/-}$ mice compared to aged WT controls (FIG. 13a). IRAP$^{-/-}$ mouse hearts also expressed less phospho-IκBα, indicative of reduced NFκB activation (FIG. 13a) and decreased inflammation as demonstrated by reduced monocyte chemoattractant protein-1 (MCP-1) expression, markedly reduced intercellular adhesion molecule 1 (ICAM-1) expression, by perivascular immunohistochemistry and Western blot analysis leading to reduced macrophage infiltration in the heart (FIG. 13). The pattern of cytokines released from the heart was also examined. There were slight increases in pro-inflammatory cytokines IL-1β, IL-17A and TNF-α in hearts of aged IRAP$^{-/-}$ mice (FIG. 14), however there were more marked increases in a number of anti-inflammatory cytokines, including IL-2, IL-4, IL-5, IL-10 and IL-12p40 (FIG. 14; Table 1) providing evidence for an anti-inflammatory phenotype in aged IRAP$^{-/-}$ mice.

TABLE 1

Cardiac cytokine protein levels. Cardiac cytokine protein levels in hearts from aged WT, aged IRAP$^{-/-}$, vehicle-treated and HFI-419-treated aged WT mice were quantified using a Bioplex cytokine assay (Bio-rad) kit with cytokine levels expressed as mean ± s.e.m in pg/ml. Cytokines are grouped based on pro-inflammatory, anti-inflammatory, colony-stimulating factor and CC chemokine ligand phenotype. Concentration of cardiac cytokines in IRAP$^{-/-}$ mice are expressed as a relative ratio to mean concentration of aged WT control; while cytokine levels in HFI-419-treated aged WT hearts are expressed as a relative ratio to mean concentration of vehicle-treated aged WT. *p<0.05, P<0.01, *P<0.0001 as determined by t-test; n = 9 in each group.

| | WT | IRAP$^{-/-}$ | Ratio of IRAP$^{-/-}$ to WT | Vehicle | HFI-419 | Ratio of HFI to Vehicle |
|---|---|---|---|---|---|---|
| Pro-inflammatory | | | | | | |
| IL-1a | 6.079 ± 0.41 | 6.764 ± 0.41 | 1.11 | 7.34 ± 0.475 | 7.61 ± 0.56 | 1.03 |
| IL-1b | 52.99 ± 6.28 | 59.32 ± 5.66 | 1.12 | 59.78 ± 7.913 | 69.83 ± 3.75 | 1.16 |
| IL-6 | 2.272 ± 0.09 | 2.548 ± 0.08 | 1.12* | 2.823 ± 0.153 | 2.766 ± 0.15 | 0.98 |
| IL-12 p70 | 20.55 ± 1.09 | 23.82 ± 1.29 | 1.16 | 26.46 ± 4.32 | 23.49 ± 1.83 | 0.88 |
| IL-17A | 6.553 ± 0.25 | 8.126 ± 0.33 | 1.24** | 8.462 ± 0.792 | 8.068 ± 0.29 | 0.95 |
| TNF-a | 185.7 ± 6.49 | 240.3 ± 5.78 | 1.18 | 239.1 ± 23.62 | 219.7 ± 9.76 | 0.92 |
| Anti-inflammatory | | | | | | |
| IL-2 | 2.971 ± 0.40 | 5.082 ± 0.82 | 1.71* | 5.227 ± 1.128 | 5.849 ± 0.78 | 1.12 |
| IL-4 | 2.422 ± 0.07 | 2.684 ± 0.86 | 1.72* | 2.782 ± 0.212 | 2.676 ± 0.06 | 1.61** |
| IL-5 | 3.378 ± 0.16 | 3.95 ± 0.18 | 1.17* | 4.052 ± 0.453 | 3.96 ± 0.14 | 0.98 |
| IL-9 | 526.7 ± 22.62 | 517.1 ± 16.63 | 0.98 | 441.9 ± 46.68 | 557.8 ± 31.03 | 1.19* |
| IL-10 | 30.43 ± 1.59 | 41.29 ± 2.16 | 1.36*** | 45.26 ± 6.033 | 40.13 ± 1.36 | 1.09 |
| IL-12 p40 | 3.903 ± 0.19 | 4.876 ± 0.21 | 1.25** | 3.742 ± 0.187 | 4.887 ± 0.28 | 1.31 |
| IL-13 | 80.14 ± 2.98 | 82.76 ± 2.24 | 1.03 | 93.62 ± 4.677 | 90.19 ± 2.93 | 0.96 |
| Colony-stimlating Factor (CSF) | | | | | | |
| G-CSF | 1.66 ± 0.05 | 1.907 ± 0.06 | 1.15 | 1.872 ± 0.258 | 1.912 ± 0.08 | 1.02 |
| GM-CSF | 34.18 ± 1.31 | 37.58 ± 1.01 | 1.1** | 38.68 ± 3.563 | 38.18 ± 1.37 | 0.99 |
| M-CSF (IL-3) | 1.402 ± 0.11 | 1.479 ± 0.06 | 1.05 | 1.528 ± 0.266 | 1.562 ± 0.11 | 1.02 |
| CC chemokine lioands (CCL) | | | | | | |
| CXCL-1 (KC) | 5.398 ± 0.34 | 5.849 ± 0.39 | 1.08 | 5.828 ± 0.542 | 6.859 ± 0.34 | 1.18 |
| CCL-3 (MIP-1a) | 1.861 ± 0.18 | 1.99 ± 0.21 | 1.07 | 2.84 ± 0.840 | 2.493 ± 0.35 | 0.88 |
| CCL-4 (MIP-1b) | 75.96 ± 9.22 | 98.8 ± 6.44 | 1.3 | 119.3 ± 10.03 | 92.74 ± 10.92 | 0.78 |
| CCL-5 (RANTES) | 2.493 ± 0.20 | 2.178 ± 0.10 | 0.87 | 2.763 ± 0.248 | 2.839 ± 0.21 | 1.03 |
| CCL-11 (Eotaxin) | 85.54 ± 12.36 | 110.5 ± 11.94 | 1.29 | 108.9 ± 27.57 | 140.3 ± 8.18 | 1.29 |

Given that aged mice lacking IRAP exhibited a cardiac phenotype of reduced ECM, inflammation and oxidative stress compared to their age-matched WT controls such that their cardiac phenotype resembled that of their young adult counterparts, the inventors were interested in whether or not pharmacological inhibition of IRAP with a small molecule IRAP inhibitor, at a time of established cardiovascular disease, would be able to reverse cardiac fibrosis. To this end, the synthetic IRAP inhibitor HFI-419 was administered for 4 weeks to ~20 month old WT mice that had established cardiac fibrosis. Indeed, HFI-419 significantly decreased IRAP expression (FIG. 8c), reversed age-induced collagen deposition to the same level seen in young adult mice (FIGS. 15 and 16) or aged IRAP$^{-/-}$ mice (FIG. 9), and also markedly reduced precursor and mature forms of collagen α1 Type I (FIG. 17); all consistent with downregulation of fibrogenic mediators such as synthetic myofibroblasts (FIG. 18) and TGF-$\beta_1$ expression (FIG. 18) following IRAP inhibition. IRAP inhibition had a slightly different effect on collagen degradation to that seen in IRAP deficient mice with a trend towards increased protein expression of the collagenase, MMP-8 whilst there was no change in MMP-2, MMP-9 or MMP-13 protein levels. However, HFI-419 treatment significantly decreased TIMP-1 protein levels, (FIG. 17), thus enabling increased activity of MMPs to provide an overall increase in collagen degradation with inhibition of IRAP.

IRAP inhibition with HFI-419 also reproduced effects on inflammatory mediators exhibited in IRAP$^{-/-}$ mice, with diminished superoxide production, NFκB activation, and reduced ICAM-1, MCP-1 and macrophage expression in aged WT mice that usually exhibited a heightened state of inflammation (FIG. 13). Moreover, pro- and anti-inflammatory cytokines were differentially regulated in HFI-419 treated WT mice (Table 1). Compared to the pro-inflammatory cytokine profile from IRAP$^{-/-}$ mice, direct IRAP inhibition did not increase any of the pro-inflammatory cytokines (FIG. 14 and Table 1) however there were marked increases in a number of anti-inflammatory cytokines, including IL-4, IL-9 and IL-12p40 (Table 1) providing evidence for an anti-inflammatory effect mediated by IRAP inhibition that mirrored the phenotype evident in aged IRAP$^{-/-}$ mice.

Structurally Distinct Classes of IRAP Inhibitors are Equally Effective in Reversing Age-Induced Cardiac Fibrosis In addition to HF1419, 2 structurally distinct chemical classes of IRAP inhibitors reverse age-induced collagen expression in the heart as shown in FIG. 19. Class 1 inhibitor is compound 1 and has the structure shown herein, whereas class 2 is compound 2 having the structure shown herein. These data show that 3 different small molecule inhibitor of IRAP have been shown to reverse collagen expression, a hallmark of fibrosis, in an age-induced model.

IRAP Inhibition and Cardiac Function

To determine if reduced extracellular matrix deposition translated to improved cardiac function two protocols have been investigated. In the first protocol, hearts were isolated from young WT, aged IRAP$^{-/-}$ mice, and aged WT mice treated with either vehicle or HFI-419 for 4 weeks and were then subjected to ischemic-reperfusion (IR) injury followed by assessment of cardiac function after IR and analysis of IR-induced infarction. At baseline there was no difference in HR, LVDP or LVEDP in aged WT (vehicle and HFI-419 treated) or aged IRAP$^{-/-}$ mice. The recovery of both LVDP and LV±dP/dt in hearts from vehicle treated aged WT mice were significantly impaired over the time course of ischemia and reperfusion compared to effect of IR injury in hearts from young WT mice (FIG. 20b,c,d), with these markers of LV function significantly reduced compared with their pre-ischemic baseline level. IRAP deficiency or chronic IRAP inhibitor treatment did not affect recovery of LVDP in the first 10 minutes of reperfusion. However, a significant improvement in latter stages of reperfusion in LVDP and LV±dP/dt was evident from 20 min of reperfusion with no significant difference between recovery of LVDP in hearts from young WT mice and those from aged IRAP$^{-/-}$ or IRAP inhibitor treated mice (FIG. 20b,c,d). The ability of IRAP deficiency or chronic IRAP inhibitor treatment to protect against IR injury was also evident when infarct area was measured; with both IRAP deficiency and IRAP inhibition resulting in ~50% reduction in infarct area compared to the aged WT control (FIG. 20a). In the second protocol echocardiography studies were used to determine whether age-induced changes in cardiac function in WT mice were reduced in aged mice that were globally deficient in IRAP. Hearts were imaged using a number of anatomical views and imaging modes via echocardiography with the baseline heart function metrics of the young and aged WT mice similar to that reported in previous echocardiography studies on mice of advanced age (Dai et al, Circulation. 2009; 119:2789-2797). However, similar to the protective effect demonstrated in isolated hearts from IRAP$^{-/-}$ mice after IR injury, aged IRAP$^{-/-}$ mice exhibit improved cardiac function with no age-induced decrease in ejection fraction (FIG. 20e) and a trend for improved left ventricular contractility (assessed via fractional area change; FAC) (FIG. 20f) when compared to age-matched WT mice (n=4-5), which correlates with the reduced fibrosis evident in the hearts from aged IRAP-/- mice and validates targeting IRAP.

IRAP Deficiency or Inhibition Did not Alter Systolic Blood Pressure, Cardiac Hypertrophy, Cardiomyocyte Hypertrophy and Medial Hypertrophy There was minimal difference between aged WT and aged IRAP$^{-/-}$ mice (FIG. 21) or HFI-419 treated aged WT mice (FIG. 16) in terms of systolic blood pressure (SBP). Cardiac hypertrophy, assessed by ventricular weight to body weight (VW:BW) ratio and ventricular weight to tibial length (VW:TL) ratio, as well as cardiomyocyte hypertrophy quantified as cross-sectional area of H&E stained cardiomyocytes, were often increased due to ageing but were not greatly influenced by IRAP deletion or pharmacological inhibition (FIGS. 21 and 16). Therefore, the striking antifibrotic and anti-inflammatory effects of HFI-419 were independent of changes in blood pressure and heart size.

The inventors have demonstrated for the first time that both IRAP deficiency and pharmacological inhibition of IRAP protected against cardiac disease. The strength of the current study was the demonstration that not only did gene deletion prevent age-induced cardiac fibrosis, but that pharmacological inhibition of IRAP completely reversed age-induced cardiac fibrosis with this latter effect being of great clinical significance. Indeed, this beneficial cardiac remodeling was associated with decreased collagen synthesis and increased collagen degradation, together with reduced cardiac and vascular inflammation. Furthermore, pharmacological inhibition of IRAP translated into functional cardiac and vascular improvement. This study shows that removal or blockade of IRAP arrests the progression of fibrosis, highlighting the inhibition of IRAP as a novel therapeutic strategy for CVD, particularly in the aging population.

Senescence is a major risk factor for CVD due to prolonged reactive cardiac remodeling, resulting in irreversible fibrosis. The increased cardiac stiffness and decreased compliance due to excessive buildup of collagen exacerbates cardiac dysfunction which may lead to CHF or impede recovery from MI, or contribute to impaired renal function. Indeed, animal senescence represents a clinically-relevant model with established cardiac fibrosis and chronic inflammation. The causes of such age-mediated cardiac fibrosis are multifactorial, with cardiac injury involving a complex interplay between profibrotic cytokines such as TGF-β and other inflammatory mediators, which then act synergistically to aggravate cardiac fibrosis. However, pharmacological treatment to reverse existing ECM and organ dysfunction is currently an unmet clinical need, since successful anti-fibrotic therapy needs to simultaneously target several key mediators. Therefore, considering the protective vascular or neuroprotective phenotypes mediated via IRAP inhibition by either Ang IV treatment or genetic ablation of IRAP, the inventors have now delineated the role of IRAP deficiency and pharmacological IRAP inhibition in aged mice, by both prevention and interventions paradigms.

In this context, our current studies have identified that the enzyme IRAP is upregulated in CVD and that inhibition of IRAP counter-regulates age-related cardiac fibrosis and dysfunction by a number of mechanisms. Collectively, the results of the current study have identified a novel therapeutic strategy in the treatment of CVD.

It is well established that aging causes cardiac dysfunction, with chronic inflammation and excessive ECM production, resulting in scarring or cardiac fibrosis. Fibrosis occurs predominantly via the upregulation of the potent pro-fibrotic cytokine TGF-β1 which promotes the differentiation of vimentin-expressing fibroblasts to αSMA-expressing myofibroblasts that leads to increased collagen production. However, aged IRAP$^{-/-}$ mice were protected against age-induced increases in interstitial collagen deposition seen in WT mice. Mechanistically, this could be explained by the fact that aged IRAP$^{-/-}$ mice exhibited a 'young adult' cardiac phenotype, with significantly less myofibroblast differentiation and TGF-β$_1$ expression compared with hearts from aged WT mice. Furthermore, fibroblast proliferation and fibrosis originates from perivascular regions and progressively extends into adjacent interstitial spaces within the heart evidenced in mice by increased perivascular expression of TGF-β$_1$ and collagen in the aged WT heart, which was abolished in the aged IRAP$^{-/-}$ mice.

The clinical relevance of IRAP as a therapeutic target was confirmed when HFI-419 was given to aged WT mice with established cardiac fibrosis, since this intervention fully reversed cardiac fibrosis by abrogating upstream fibrogenic mechanisms, such as myofibroblast differentiation and TGF-β expression, in an identical manner to genetic deletion. Moreover, IRAP was co-localized with myofibroblasts in both interstitial and perivascular region of heart, thus providing the anatomical framework for IRAP to modulate myofibroblast expression and ECM synthesis. At the same time, ECM is degraded by proteases such as MMPs. In aged mice, IRAP deletion or pharmacological inhibition increased MMP-13 and/or MMP-8 and decreased TIMP-1, suggesting that collagen degradation, together with decreased collagen synthesis, contributed to the antifibrotic phenotype of aged hearts in the absence of IRAP.

Fibrosis is often preceded by inflammation, due to infiltration of inflammatory cells during the initial phase of injury and the subsequent production of multiple cytokines. Aging also elevates ROS, which exacerbates inflammation. NFκB activation increases chemoattractants such as MCP-1 and ICAM-1, promoting inflammatory cell infiltration into the diseased heart whereby monocytes are differentiated into macrophages which also produce superoxide and TGF-β$_1$ that induce myofibroblast differentiation and aggravates cardiac fibrosis. Aged IRAP$^{-/-}$ mice exhibited an anti-inflammatory cardiac phenotype and, remarkably, treatment with HFI-419 reversed existing inflammation in the heart, with similarly reduced superoxide, phospho-IκBα, MCP-1, ICAM-1 expression, and reduced macrophage infiltration in both experimental models. These findings were generally consistent with the cardiac cytokine analysis which indicated relatively greater increases in a number of anti-inflammatory cytokines than pro-inflammatory cytokines due to IRAP deletion. More strikingly, HFI-419 elevated anti-inflammatory cytokines only. Thus, given the cross-talk between inflammatory and fibrotic pathways, it is likely that the prevailing anti-inflammatory state due to IRAP deletion or inhibition in aged hearts contributes to the normalization of cardiac fibrosis in both experimental paradigms. Importantly, the anti-inflammatory effect of HFI-419 and IRAP deletion was also noted in vascular tissue.

Given the cardiovascular protective effects for IRAP inhibition deduced from histo-morphological considerations, the inventors also examined if these beneficial effects could be translated into cardiac functional improvements. It is well established that the heart muscle can be damaged in response to ischemia-reperfusion (IR) injury, resulting in decreased LVDP following IR injury, which was evident in our aged WT mice following IR, indicating compromised contractility of the fibrotic heart. Hearts from IRAP$^{-/-}$ mice or WT mice chronically treated with HFI-419 for 4 weeks showed significant improvement in post-ischemic recovery of LVDP. The improved functional effects also correlated well with reduction in infarct area following IR injury.

In conclusion, genetic deficiency or pharmacological inhibition of IRAP virtually abolished cardiac fibrosis, with the important finding that chronic IRAP inhibitor treatment completely reversed age-induced cardiac fibrosis in ~2-year old mice. The mechanisms underlying the cardio-, reno- and vaso-protective effects of IRAP inhibition are likely to be multi-factorial. These effects include an altered balance of the ECM (decreased production and increased degradation) that favours reduced fibrosis, together with a variety of anti-inflammatory effects; all, or some, of which may result from changes in IRAP substrate levels and/or altered IRAP signalling pathways. Collectively, these findings suggest that IRAP plays a key role in the pathogenesis of cardiovascular disease and highlight the potential of pharmacological inhibition of IRAP as a novel therapeutic strategy, particularly for difficult-to-treat end-organ damage that occurs with aging and/or hypertension- or cardiovascular-related injury.

Collectively, these studies provide compelling proof-of-principle that removal or inhibition of IRAP activity has dramatic effects on cardiac, renal and vascular tissue fibrosis and have identified IRAP as a novel target in CVD.

Example 3

Approximately, 1.7 million Australians and 26 million Americans have chronic kidney disease with reduced kidney function. The final manifestation of chronic kidney disease (CKD) is renal fibrosis characterized by tubulointerstitial fibrosis & glomerulosclerosis.

The studies in this Example show that removal or inhibition of IRAP activity has dramatic effects on kidney fibrosis and have identified IRAP as a novel target in CKD.

Regulation of IRAP Expression and Fibrosis in the Kidney of Aged Mice

Similar to Example 2 above regarding cardiac fibrosis, two specific experimental paradigms were used. Hence the inventors compared the kidney phenotype between aged WT and global IRAP knockout mice (aged between 18-22 months) & young WT mice (aged 4-6 months) to determine prevention of age-related kidney fibrosis development. The inventors also compared the treatment of WT aged mice with vehicle or with a small molecule inhibitor of IRAP to determine therapeutic treatment of established fibrosis and established the effect of IRAP inhibition on reversal of age-related kidney fibrosis.

IRAP expression is increased in kidneys of aged WT mice compared to levels expressed in kidneys from young WT mice (FIG. 22a). IRAP expression tended to be decreased in kidneys of aged WT mice after 4 weeks of treatment with the inhibitor of IRAP (HFI-419). Similar to immunofluorescence studies in the heart, the specificity of the IRAP antibody was confirmed by the absence of staining in kidneys obtained from aged IRAP$^{-/-}$ mice (FIG. 22a).

IRAP deficiency and IRAP Inhibitor Treatment in Age-Induced Renal Fibrosis Kidney interstitial fibrosis, assessed by collagen content using picrosirius red staining and quantified using bright field microscopy, was evaluated in young WT, aged WT and IRAP$^{-/-}$ mice as well as in aged WT mice treated with either vehicle or HFI-419 (500 ng/kg/min; s.c.) for 4 weeks. As expected, aging significantly increased kidney interstitial fibrosis (FIG. 23a). In contrast to the increase in collagen seen in kidneys from our aged WT mice, aged IRAP$^{-/-}$ mice exhibited ECM deposition similar to that seen in young adult WT mice (FIG. 23a) indicative of an antifibrotic effect in the absence of IRAP and consistent with the antifibrotic effect seen in hearts from aged IRAP$^{-/-}$ mice (Example 2). Given that aged WT mice have significant increases in kidney fibrosis and aged mice lacking IRAP demonstrate a kidney phenotype of reduced collagen expression similar to that of their young adult counterparts, the inventors were interested in whether or not pharmacological inhibition of IRAP with a small molecule IRAP inhibitor, at a time of established cardiovascular/renal disease, would be able to reverse kidney fibrosis. To this end, the synthetic IRAP inhibitor HFI-419 was administered for 4 weeks to ~20 month old WT mice that had established kidney fibrosis. Indeed, HFI-419 displayed a significant effect to completely reverse age-induced collagen deposition to a similar level seen in young adult WT and IRAP$^{-/-}$ mice (FIG. 23a & b).

Increased fibrosis can be due to greater differentiation of fibroblasts to a more synthetic type of myofibroblast. In this context, kidneys from aged WT mice exhibited significantly more αSMA-positive myofibroblast expression than kidneys from young WT controls (FIG. 24a). In contrast, kidneys from aged IRAP$^{-/-}$ mice did not exhibit this age-dependent myofibroblast upregulation, resulting in myofibroblast expression similar to that found in kidneys from young WT mice (FIG. 24a). These results suggest that exaggerated collagen production due to increased synthetic myofibroblast activity contributed to the increased fibrosis noted in aged WT kidneys, and that this phenomenon was severely blunted in kidneys from aged IRAP$^{-/-}$ mice. IRAP inhibition with HFI-419 for 4 weeks in aged WT mice demonstrated a trend towards reduced αSMA-positive myofibroblast expression in kidneys when compared to the age-matched vehicle-treated control mice (FIG. 24b).

Example 4

To elucidate mechanisms underlying cardio-protective effect of IRAP inhibition in a clinically relevant human model, a primary cell line of human cardiac fibroblasts was studied. The studies were performed to answer the following questions: Is IRAP present in these cells and does a profibrotic stimulator increase IRAP expression? Can IRAP inhibition reduce myofibroblast expression/collagen production?

Increased IRAP Expression in Human Cardiac Fibroblasts Stimulated with Angiotensin II Representative images showing primary human cardiac fibroblasts stimulated with increasing concentrations of Ang II induced an increase in expression of IRAP (FIG. 25). There is a clear dose dependent increase in IRAP expression in the human cardiac fibroblasts.

IRAP Inhibitor Dose-Dependently Decreased α-SMA and Collagen Expression in Human Cardiac Fibroblasts Pharmacological IRAP inhibition with a small molecule, HFI-419, dose-dependently decreased myofibroblast expression (α-SMA staining) and collagen production. Representative images showing increased expression of α-SMA (red; marker for myofibroblasts) and collagen (green) when human cardiac fibroblasts (HCFs) were stimulated with Ang II (0.1 μM) (FIG. 26a). Combined Ang II and HFI-419 treatment (0.01 to 1 μM) decreased α-SMA and collagen expression. FIG. 26b is quantitative data from western blots confirming dose-dependent decrease in protein expression of α-SMA and collagen when HCFs were co-treated with Ang II+ increasing concentrations of HFI-419 (n=10-12). Data expressed as mean s.e.m; densitometric analysis of western blots expressed as relative ratio to mean of control cells±s.e.m; *P<0.05; P<0.01; *P<0.001 determined by one way ANOVA with Bonferroni correction for multiple comparisons.

Example 5

Effect of IRAP Gene Deletion on Liver Steatosis

Male IRAP knockout mice (IRAO KO: global deletion of the gene for insulin-regulated aminopeptidase), aged 6 months of age, and their wildtype counterparts, were fed either a high fat diet (HFD) or a normal diet (ND). After 4 weeks of dietary manipulation, whole body metabolism was measured in all groups of mice using the Oxymax Lab Animal Monitoring System (Columbus Instruments, OH, U.S.A.). As expected, mice fed the HFD had a decreased respiratory exchange ratio (ratio between the amount of carbon dioxide produced in metabolism and oxygen used) and increased heat production when compared to ND fed mice but there was no difference between genotypes over a 48 hr period.

After 12 weeks of dietary manipulation, mice were killed for tissue collection. Blood, brain, liver, kidneys, gonadal white adipose tissue (visceral fat), inguinal white adipose tissue (subcutaneous fat), brown adipose tissue (thermogenic fat), intestines, heart and aorta were collected. Tissue weight was different only in the inguinal white adipose tissue, with wildtype mice fed the HFD having a significantly heavier inguinal white adipose tissue deposit than all other groups.

Liver weights were not different between groups but histological examination of this tissue showed greater levels of steatosis in HFD fed mice compared to ND fed mice and the IRAP KO mice on a HFD displayed reduced steatosis compared to WT mice on a HFD (FIG. 27). This shows that HFD fed mice displayed non-alcoholic fatty liver disease (NAFLD), or early stage non-alcoholic steatohepatitis (NASH), while inhibition of IRAP in these mice prevented the excess lipid accumulation in vesicles.

Example 6

Pharmacological Inhibition of IRAP Reverses High Salt Induced Increase in Liver Fibrosis Salt is well known to be an accelerating factor for the progression of metabolic syndrome and is implicated in development of cardiovascular diseases, most likely due to its pro-oxidant properties. Recent evidence indicates that a high salt diet (HSD) can exacerbate fat and fibrosis accumulation in the liver of HFD-fed lectin like oxidized low-density lipoprotein receptor-1 (LOX-1) transgenic (Tg) and apoE knockout (KO) (TgKO) mice, a model used in studies investigating metabolic syndrome (Uetake et al, Lipids in Health and Disease (2015) 14:6). We were therefore interested in whether a HSD alone induces significant changes in liver fibrosis and would IRAP inhibitor treatment reverse these fibrotic changes. Feeding a HSD for 8 weeks to WT (C57B/6J) mice significantly increased fibrosis and number of vacuoles in the liver indicating that this model has all the hallmarks of NASH, including exacerbated fibrosis. The synthetic IRAP inhibitor HFI-419 was administered for 4 weeks to ~20 week old WT mice that had already been fed a HSD for an initial 4 weeks to initiate changes in the liver. Indeed, HFI-419 significantly reversed HSD-induced collagen deposition to the same level seen in mice fed a normal chow diet (FIG. 28) and markedly reduced indicators of steatosis in the liver (FIG. 28). These anti-fibrotic effects are in line with previous findings showing a clear ability for the synthetic IRAP inhibitor, HFI-419 to reverse established cardiac fibrosis.

---

The invention claimed is:

1. A method of treating steatosis in an individual comprising administering an inhibitor of insulin-regulated aminopeptidase (IRAP) thereby treating steatosis.

2. The method according to claim 1, wherein the steatosis is nonalcoholic fatty liver disease (NAFLD).

3. The method according to claim 1, wherein the steatosis is alcoholic steatohepatitis (ASH).

4. The method according to claim 1, wherein the steatosis is non-alcoholic steatohepatitis (NASH).

5. The method according to claim 1, wherein the inhibitor of RAP directly inhibits the enzymatic activity of IRAP.

6. The method according to claim 1, wherein the inhibitor;
(i) binds to RAP;
(ii) binds to the active site of RAP; or
(iii) competes with a substrate of RAP for binding to RAP.

7. The method according to claim 1, wherein the inhibitor of RAP exhibits a Ki value of less than 1 mM, as determined by an assay of aminopeptidase activity or substrate degradation, wherein the assay of amino peptidase activity comprises hydrolysis of the synthetic substrate L-Leucine 7-amido-4-methyl coumarin hydrochloride (Leu-MCA) monitored by release of the fluorogenic product MCA;

wherein the assay of substrate degradation is degradation of the peptide substrates CYFQNCPRG or YGGFL.

8. The method according to claim 1, wherein the inhibitor is selected from the group consisting of a small molecule, an antibody and a peptide.

9. The method according to claim 1, wherein the inhibitor has a structure according to Formula (I):

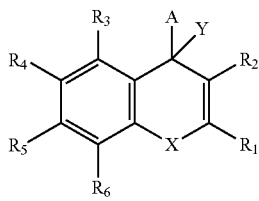

(I)

wherein

A is aryl, heteroaryl carbocyclyl or heterocyclyl, each of which may be optionally substituted, when $R^1$ is $NHCOR_8$;
or quinolinyl, isoquinolinyl, cinnolinyl, quinazolinyl, quinoxalinyl, 1,8-naphthyridyl, phthalazinyl or pteridinyl, each of which may be optionally substituted, when $R^1$ is $NR_7R_8$, $NHCOR_8$, $N(COR_8)_2$, $N(COR_7)(COR_8)$, $N=CHOR_8$ or $N=CHR_8$;

X is O, NR' or S, wherein R' is hydrogen, optionally substituted alkyl, optionally substituted alkenyl, optionally substituted alkynyl, optionally substituted aryl, optionally substituted acyl, optionally substituted heteroaryl, optionally substituted carbocyclyl or optionally substituted heterocyclyl;

$R_7$ and $R_8$ are independently selected from hydrogen, optionally substituted alkyl, optionally substituted aryl, or $R_7$ and $R_8$, together with the nitrogen atom to which they are attached form a 3-8-membered ring which may be optionally substituted;

$R^2$ is CN, $CO_2R^9$, $C(O)O(O)R^9$, $C(O)R^9$ or $C(O)NR^9R^{10}$ wherein $R^9$ and $R^{19}$ are independently selected from alkyl, alkenyl, alkynyl, aryl, heteroaryl, carbocyclyl, heterocyclyl, each of which may be optionally substituted, and hydrogen; or $R^9$ and $R^{10}$ together with the nitrogen atom to which they are attached, form a 3-8-membered ring which may be optionally substituted;

$R_3$-$R_6$ are independently selected from hydrogen, halo, nitro, cyano alkyl, alkenyl, alkynyl, aryl, heteroaryl, heterocyclyl, carbocyclyl, hydroxy, alkoxy, alkenyloxy, alkynyloxy, alkynyloxy, aryloxy, heteroaryloxy, heterocyclyloxy, amino, acyl, acyloxy, carboxy, carboxyester, methylenedioxy, amido, thio, alkylthio, alkenylthio, alkynylthio, arylthio, heteroarylthio, heterocyclylthio, carbocyclylthio, acylthio and azido, each of which may be optionally substituted where appropriate, or any two adjacent $R^3$-$R^6$, together with the atoms to which they are attached, form a 3-8-membered ring which may be optionally substituted; and Y is hydrogen or $C_{1-10}$alkyl, or a pharmaceutically acceptable salt or solvate thereof.

10. The method according to claim 9, wherein the inhibitor has the structure:

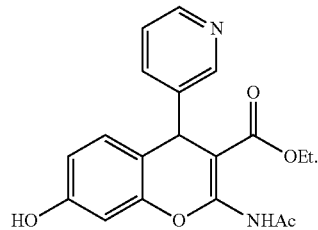 [SMILES: CCOC(=O)C1=C(NC(C)=O)Oc2cc(O)ccc2C1c1cccnc1]

11. The method according to claim 1, wherein the inhibitor is an interfering RNA.

12. The method according to claim 1, wherein the inhibitor has a structure according to Formula (II):

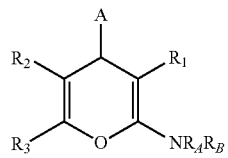

(II)

wherein

A is selected from alkyl, alkenyl, alkynyl, aryl, arylalkyl, heteroaryl, heteroarylalkyl, carbocyclyl, carbocyclylalkyl, each of which may be optionally substituted;

$R_A$ and $R_B$ are independently selected from hydrogen, alkyl and acyl;

$R_1$ is selected from CN or $CO_2R_C$;

$R_2$ is selected from $CO_2R_C$ and acyl;

$R_3$ is selected from alkyl, alkenyl, alkynyl, aryl, arylalkyl, heteroaryl, heteroarylalkyl, carbocyclyl, carbocyclylalkyl, each of which may be optionally substituted; or $R_2$ and $R_3$ together form a 5-6-membered saturated keto-carbocyclic ring:

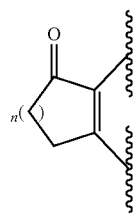

wherein n is 1 or 2;
and which ring may be optionally substituted one or more times by $C_{1-6}$alkyl; or $R_2$ and $R_3$ together form a 5-membered lactone ring (a) or a 6-membered lactone ring (b)

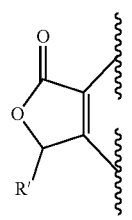

(a)

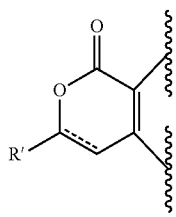

wherein ⋯ an optional double bond and R' is alkyl;
$R_C$ is selected from alkyl, alkenyl, alkynyl, aryl, arylalkyl, heteroaryl, heteroarylalkyl, carbocyclyl, carbocyclylalkyl, each of which may be optionally substituted;
or a pharmaceutically acceptable salt, solvate or prodrug thereof.

13. The method according to claim 12, wherein the inhibitor has the structure:

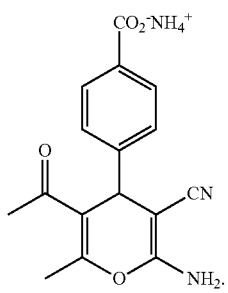

14. The method according to claim 1, wherein the inhibitor has a structure according to Formula (III):

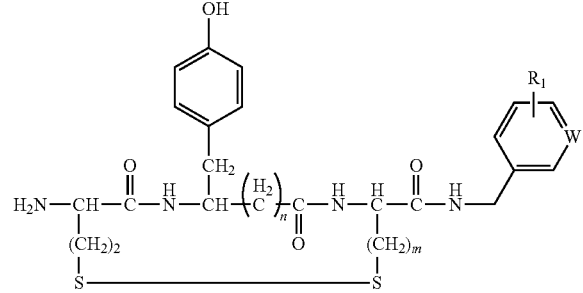

wherein
$R_1$ is H or $CH_2COOH$; and
n is 0 or 1; and
m is 1 or 2; and
W is CH or N;
or a pharmaceutically acceptable salt, solvate or prodrug thereof.

15. The method according to claim 14, wherein the inhibitor has the structure:

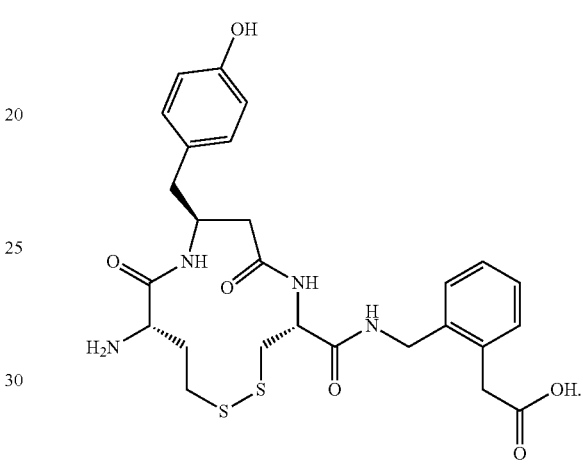

16. The method according to claim 1, wherein the inhibitor has a structure according to any one of the following sequences:

```
Val-Tyr-Ile-His-Pro-Phe,
c[Cys-Tyr-Cys]-His-Pro-Phe,
and
c[Hcy-Tyr-Hcy]-His-Pro-Phe.
```

17. A method according to claim 1, wherein the inhibitor has a structure according to:

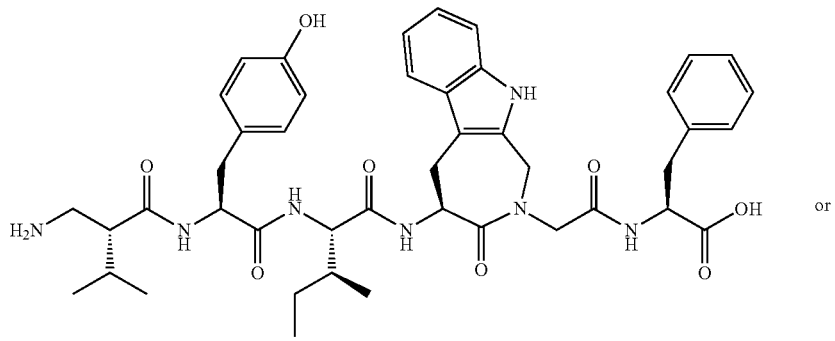

or

-continued
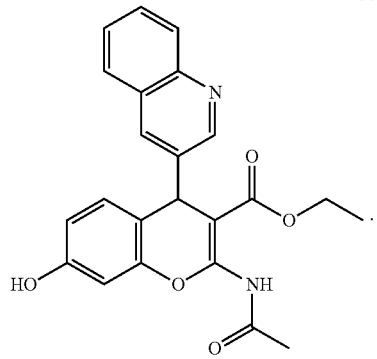
18. A method for improving heart function or decreasing infact area following ischemic-reperfusion injury in an individual, the method comprising administering an inhibitor of insulin-regulated aminopeptidase (IRAP) to the individual thereby improving heart function or decreasing infact area following ischemic-reperfusion injury.
* * * * *

UNITED STATES PATENT AND TRADEMARK OFFICE
CERTIFICATE OF CORRECTION

PATENT NO. : 11,078,488 B2  
APPLICATION NO. : 16/984996  
DATED : August 3, 2021  
INVENTOR(S) : Siew Yeen Chai et al.

Page 1 of 1

It is certified that error appears in the above-identified patent and that said Letters Patent is hereby corrected as shown below:

In the Specification

In Column 6, Line 2, delete "$CH_2OOH$" and insert --$CH_2COOH$--;
In Column 21, Line 36, delete "$CH_2OOH$" and insert --$CH_2COOH$--;
In Column 43, Line 13, delete "$H_2O$ for seconds" and insert --$H_2O$ for 30 seconds--;
In Column 50, Line 6, delete "PGT/AU2016/050332" and insert --PCT/AU2016/050332--;

In the Claims

In Claim 6, Line 61, delete "binds to RAP" and insert --binds to IRAP--;
In Claim 6, Line 62, delete "site of RAP" and insert --site of IRAP--;
In Claim 6, Line 63, delete "competes with a substrate of RAP for binding to RAP" and insert --competes with a substrate of IRAP for binding to IRAP--;
In Claim 7, Line 65, delete "RAP exhibits" and insert --IRAP exhibits--;

Signed and Sealed this  
Nineteenth Day of October, 2021

Drew Hirshfeld  
*Performing the Functions and Duties of the*  
*Under Secretary of Commerce for Intellectual Property and*  
*Director of the United States Patent and Trademark Office*